(12) United States Patent
Blattner et al.

(10) Patent No.: US 10,930,369 B1
(45) Date of Patent: *Feb. 23, 2021

(54) SYSTEMS AND METHODS FOR IDENTIFYING NUCLEOTIDE SEQUENCE MATCHES

(71) Applicant: DNASTAR, INC., Madison, WI (US)

(72) Inventors: Frederick R. Blattner, Madison, WI (US); Schuyler F. Baldwin, Madison, WI (US); Timothy J. Durfee, Madison, WI (US); Daniel A. Nash, Madison, WI (US); Kenneth C. Dullea, Madison, WI (US); Richard D. Nelson, Madison, WI (US)

(73) Assignee: DNASTAR, INC., Madison, WI (US)

( * ) Notice: Subject to any disclaimer, the term of this patent is extended or adjusted under 35 U.S.C. 154(b) by 721 days.

This patent is subject to a terminal disclaimer.

(21) Appl. No.: 14/795,783

(22) Filed: Jul. 9, 2015

Related U.S. Application Data

(63) Continuation-in-part of application No. 12/720,638, filed on Mar. 9, 2010, now Pat. No. 9,109,861.

(60) Provisional application No. 61/158,730, filed on Mar. 9, 2009.

(51) Int. Cl.
*G16B 30/00* (2019.01)

(52) U.S. Cl.
CPC .................................. *G16B 30/00* (2019.02)

(58) Field of Classification Search
None
See application file for complete search history.

(56) References Cited

U.S. PATENT DOCUMENTS 6,223,128 B1  4/2001 Allex et al.
8,209,130 B1  6/2012 Kennedy et al.

OTHER PUBLICATIONS

Bonfield et al. (Nucleic Acids Res., Dec. 25, 1995;23(24):4992-9). (Year: 1995).*
Kent et al. (Genome Res., 2001, 11:1541-1548). (Year: 2001).*
Batzoglou, S., et al., "ARACHNE: A Whole-Genome Shotgun Assembler," Genome Research, vol. 12, No. 1, pp. 177-189 (Jan. 2002).
Bonfield, J., et al., "A new DNA sequence assembly program," Nucleic Acids Research, vol. 23, No. 24, pp. 4992-4999 (Dec. 25, 1995).
Kent, W., et al., "Assembly of the Working Draft of the Human Genome with GigAssembler," Genome Research, pp. 1541-1548 (Sep. 2001).
Klein, J., et al., "LOCAS—A Low Coverage Assembly Tool for Resequencing Projects." PLOS One, vol. 6, Issue 8, a23455 (Aug. 15, 2011).
Langmead, B., et al., "Ultrafast and Memory-Efficient Alignment of Short DNA Sequences to the Human Genome," Genome Biology, vol. 10, R25-R25.10 (Mar. 4, 2009).
Li, H., et al., Fast and Accurate Short Read Alignment with Burrows-Wheeler Transform, Bioinformatics, vol. 25, No. 14, pp. 1754-1760 (May 18, 2009).
Li., R., "SOAP2: an Improved Ultrafast Tool for Short Read Alignment," Bioinformatics, vol. 25, No. 15, pp. 1966-1967 (Jun. 3, 2009 epublished).
MacCallum, I., et al., "ALLPATHS 2: Small Genomes Assembled Accurately and with High Continuity from Short Paired Reads," Genome Biology, vol. 10:R103, (Oct. 2009).
Mullikin, J., et al., The Phusion Assembler, Genome Research, vol. 13, No. 1, pp. 81-90 (Feb. 2003).
Pennisi, E., "Semiconductors Inspire New Sequencing Technologies," vol. 327, p. 1190 (Mar. 5, 2010).
Simpson, J., et al., "ABySS: A Parallel Assembler for Short Read Sequence Data," Genome Research, vol. 19, No. 6, pp. 1117-1123 (Jun. 2009).
Sutton, G., et al., "TIGR Assembler: A New Tool for Assembling Large Shotgun Sequencing Projects," Genome Science & Technology, vol. 1, No. 1, pp. 9-19 (Jan. 1, 1995).
Tritt, Andrew, et al., "An Integrated Pipeline for de Novo Assembly of Microbial Genomes," PLOS One, vol. 7, Issue 9, e42304, pp. 1-9 (Sep. 13, 2012).
Venter, J., et al., "A New Strategy for Genome Sequencing," Nature, vol. 381, pp. 364-366 (May 30, 1996).
Weber, J., et al., "Human Whole-Genome Shotgun Sequencing," Genome Research, vol. 7, pp. 401-409 (Jun. 1997).
Zerbino, D., et al., "Velvet: Algorithms for de Novo Short Read Assembly Using de Bruijn Graphs," vol. 5, pp. 821-829 (May 2008) epublished Mar. 18, 2008.
Zerbino, D., Velvet Manual—version 1.1, pp. 1-22 (Aug. 29, 2008).
Declaration of inventor, Frederick R. Blattner dated Jan. 12, 2015.
ARACHNE: A Whole-Genome Shotgun Assembler; Batzoglou et al., downloaded from genome.cship.org on Mar. 4, 2009—Published by Cold Spring Harbor Laboratory Press.
A new DNA sequence assembly program; Bonfield et al. MRC Laboratory of Molecular Biology, Hills Road, Cambridge DB2 2QH, UK; revised and accepted Nov. 15, 1995 (4992-4999 Nucleic Acids Research, 1995, vol. 23, No. 24.
LOCAS—A Low Coverage Assembly Tool for Resequencing Projects; Klein et al; PLOS One, Aug. 2011, vol. 6, Issue 8, e23455.

(Continued)

*Primary Examiner* — Pablo S Whaley
(74) *Attorney, Agent, or Firm* — Much Shelist PC; Christopher M. Cabral

(57) ABSTRACT

Systems and methods automatically identify a set of read sequences in one or more larger nucleotide sequences within a set of comparing sequences as a template. The sequences of each set are divided into smaller mer sequences and sorted to arrange the mer sequences in order, and the sets of mers originating from the read sequence set and the comparing sequence set are compared pairwise to determine matching regions between the sequences of the read sequence set and the sequences of the comparing set. The sorting of the sequence sets prior to the pairwise comparison reduces the amount of volatile memory required to assemble the read sequence set and also reduces the overall time to identify matches of the read sequence set in one or more larger nucleotide sequence databases.

16 Claims, 52 Drawing Sheets

Specification includes a Sequence Listing.

(56) References Cited

OTHER PUBLICATIONS

Software: Ultrafast and memory-efficient alignment of short DNA sequences to the human genome, Langmead, et al.; Software, Published: Mar. 4, 2009; Open Access.
Sequence analysis; SOAP2: an improved ultrafast tool for short read alignment, Li et al., Bioinformatics Applications Note; vol. 25 No. 15 2009; accepted May 24, 2009.
Method: ALLPATHS 2: small genomes assembled accurately and with high continuity from short paired reads; MacCallum et al: accepted Oct. 1, 2009; Open Access.
Resources: ABySS: A parallel assembler fro short read sequence data, Simpson et al; downloaded from genome.cship.org on Oct. 11, 2011—Published by Cold Spring Harbor Laboratory Press.
TIGR Assembler: A New Tool for Assembling Large Shotgun Sequencing Projects; Sutton et al.; Genome Sciene & Technology, vol. 1, No. 1, 1995, Mary Ann Liehert, Inc.
An Integrated Pipeline for de Novo Assembly of Microbial Genomes, Tritt et al; PLOS One, Sep. 2012, vol. 7, Issue 9, e42304.
Resource: Velvet: Algorithms for de novo short read assembly using de Bruijn graphs, Zerbino et al: Genome Research, 821-829 2008 by Cold Spring Harbor Laboratory Press; ISSN 10088-905 1/08; www.genome.org.
Sequence analysis; Fast and accurate short read alignment with Burrows-Wheeler transform, Ii et al; Bioinformatics Original Paper, vol. 25, No. 14 2009, pp. 1754-1760, accepted on May 12, 2009.
Commentary: A new strategy for genome sequencing, venter et al.; NATURE—vol. 381, May 30, 1996.
Perspective: Human Whole-Genome Shotgun Sequencing, Weber et al. Genome Research—401-409, 1997 by Cold Spring Harbor Laboratory Press ISSN 1054-9803/97.

\* cited by examiner

```
DNASTAR ALIGNMENT OUTPUT
created on: 2015-Jun-23 12:19:37
```

Query
```
Query: "cysH" "" (2886334 < 2885600) ; ; name: "cysH" ; featureType: "CDS"
Length: 735
QueryID: 428
```

DB match
```
Template: gi|41197|emb|Y07525.1| Escherichia coli cysH and cysI (parti
    al) genes for PAPS-reductase and sulfite reductase
Length: 2866
TemplateID: 11557
```

Alignment

```
Query    1     ATGTCCAAACTCGATCTAAACGCCCTGAACGAACTGCCGAAGGTAGATCGCATTCTGGCG    60
               ||||||||||||||||||||||||||||||||||||||||||||||||||||||||||||
Sbjct    769   ATGTCCAAACTCGATCTAAACGCCCTGAACGAACTGCCGAAGGTAGATCGCATTCTGGCG    828

Query    61    CTGGCGGAAACTAACGCCGAACTGGAAAAACTGGACGCTGAAGGCCGCGTAGCCTGGGCG    120
               ||||||||||||||||||||||||||||||||||||||||||||||||||||||||||||
Sbjct    829   CTGGCGGAAACTAACGCCGAACTGGAAAAACTGGACGCTGAAGGCCGCGTAGCCTGGGCG    888

Query    121   CTGGATAATCTGCCCGGTGAATATGTACTTTCTTCCAGCTTTGGCATTCAGGCGGCGGTG    180
               ||||||||||||||||||||||||||||||||||||||||||||||||||||||||||||
Sbjct    889   CTGGATAATCTGCCCGGTGAATATGTACTTTCTTCCAGCTTTGGCATTCAGGCGGCGGTG    948

Query    181   AGCCTGCATCTGGTGAATCAAATTCGCCCGGATATTCCGGTGATCCTCACCGATACGGGT    240
               ||||||||||||||||||||||||||||||||||||||||||||||||||||||||||||
Sbjct    949   AGCCTGCATCTGGTGAATCAAATTCGCCCGGATATTCCGGTGATCCTCACCGATACGGGT    1008

Query    241   TACTTGTTCCCGGAAACCTACCGCTTTATTGACGAGTTAACGGACAAACTCAAGCTCAAC    300
               ||||||||||||||||||||||||||||||||||||||||||||||||||||||||||||
Sbjct    1009  TACTTGTTCCCGGAAACCTACCGCTTTATTGACGAGTTAACGGACAAACTCAAGCTCAAC    1068

Query    301   CTGAAAGTGTACCGTGCTACCGAAAGCGCAGCCTGGCAGGAAGCACGCTACGAAAACTG    360
               ||||||||||||||||||||||||||||||||||||||||||||||||||||||||||||
Sbjct    1069  CTGAAAGTGTACCGTGCTACCGAAAGCGCAGCCTGGCAGGAAGCACGCTACGAAAACTG    1128

Query    361   TGGGAGCAGGGCGTTGAAGGCATTGAAAAGTACAATGACATCAACAAAGTCGAACCGATG    420
               ||||||||||||||||||||||||||||||||||||||||||||||||||||||||||||
Sbjct    1129  TGGGAGCAGGGCGTTGAAGGCATTGAAAAGTACAATGACATCAACAAAGTCGAACCGATG    1188

Query    421   AACCGGGCTCTGAAAGAACTGAATGCGCAAACCTGGTTTGCTGGCCTGCGCCGTGAACAA    480
               ||||||||||||||||||||||||||||||||||||||||||||||||||||||||||||
Sbjct    1189  AACCGGGCTCTGAAAGAACTGAATGCGCAAACCTGGTTTGCTGGCCTGCGCCGTGAACAA    1248

Query    481   TCCGGCAGTCGTGCCAATTTACCGGTGCTGGCAATTCAGCGTGGCGTATTTAAAGTGCTG    540
               ||||||||||||||||||||||||||||||||||||||||||||||||||||||||||||
Sbjct    1249  TCCGGCAGTCGTGCCAATTTACCGGTGCTGGCAATTCAGCGTGGCGTATTTAAAGTGCTG    1308

Query    541   CCGATTATCGACTGGGATAACCGAACTATTTATCAGTACCTGCAAAAACATGGCCTGAAA    600
               ||||||||||||||||||||||||||||||||||||||||||||||||||||||||||||
Sbjct    1309  CCGATTATCGACTGGGATAACCGAACTATTTATCAGTACCTGCAAAAACATGGCCTGAAA    1368

Query    601   TATCACCCATTATGGGATGAAGGATATTTATCCGGTGGGCGATACCCATACAACCCGTAAA    660
               ||||||||||||||||||||||||||||||||||||||||||||||||||||||||||||
Sbjct    1369  TATCACCCATTATGGGATGAAGGATATTTATCCGGTGGGCGATACCCATACAACCCGTAAA    1428

Query    661   TGGGAACCCGGCATGGCGGAAGAAGAAACGCGTTTCTTTGGCTTAAAAAGGGAATGTGCG    720
               ||||||||||||||||||||||||||||||||||||||||||||||||||||||||||||
Sbjct    1429  TGGGAACCCGGCATGGCGGAAGAAGAAACGCGTTTCTTTGGCTTAAAAAGGGAATGTGCG    1488

Query    721   TTACACGAAGGGTAA (SEQ ID NO:4)                                735
               |||||||||||||||
Sbjct    1489  TTACACGAAGGGTAA (SEQ ID NO:5)                                1503
```

Alignment Statistics
```
Matches = 735    Mismatches = 0 , Gaps = 0
Score = 1366.93 bits (735), Expect = 0
Identities = 735/735 (100%)
Gaps = 0/735 (0%)
Strand = Plus/Plus
```

SYSTEMS AND METHODS FOR IDENTIFYING NUCLEOTIDE SEQUENCE MATCHES

RELATED APPLICATIONS

This application is a continuation-in-part of U.S. application Ser. No. 12/720,638 filed Mar. 9, 2010 which claims priority from Provisional Application No. 61/158,730 filed on Mar. 9, 2009, each of which are incorporated herein by reference in their entirety.

FEDERALLY SPONSORED RESEARCH OR DEVELOPMENT

This work may have been partially supported by a Phase I grant from the National Institutes of Health grant number R43 GM082117-01 and a Phase II grant from the National Institutes of Health grant number R44 GM082117-02A1. The U.S. government may have certain rights in this invention.

INCORPORATION OF SEQUENCE LISTING

The entire contents of a paper copy of the "Sequence Listing" in computer readable form (.txt) that is identical to the PatentIn 3.5 computer software generated sequence listing containing the file name SequenceListing 070477-5001-US-01_ST25.txt, which is 3 kilobytes in size and was created on Sep. 29, 2015, is herein incorporated by reference in its entirety.

BACKGROUND

Genomics, the study of the genomes of organisms, is an active area of biotechnology that has been used to identify targets for pharmaceutical compounds and to gain insight into disease mechanisms. As the field of genomics has matured, automated nucleotide sequencing techniques and advanced assembly algorithms have resulted in the complete sequencing of the genomes of hundreds of organisms, including the human genome. Recently developed automated sequencing devices make use of automated and massively parallel sequencing techniques to produce gigabases of data in a single machine run. These automated sequencing devices have greatly reduced the time and cost of sequencing the genomes of individual humans, making personalized medicine increasingly feasible. Personalized medicine makes use of an individual's sequenced genome to determine the individual's susceptibility to diseases and to determine the individual's responsiveness to drug regimes.

Typically, automated sequencing technologies cleave the nucleotide sample to be processed into a set of smaller nucleotide strands, which are then sequenced, yielding a read sequence set containing all of the reads from a sample. Each read of the read sequence set is the nucleotide sequence of one of the smaller nucleotide strands, as determined by the automated sequencing device. The read sequence set is then assembled into a complete genome by piecing together the reads into a continuous nucleotide sequence by aligning overlapping portions of the reads in the set.

A challenging computational task related to assembling the read sequence data into a genome is the alignment of the sequences. The sequences in the read sequence data set may either be compared to other sequences in the data set (de novo assembly) and arranged so that sequences with the same series of nucleotide bases are overlapped, or the sequences may be assembled by aligning the sequences in the read sequence data set to a data set of an existing template genome, such as a data set in a publicly available genetic database (reference-guided assembly). Regardless of the methods used, the assembly of the sequences into a genome entails the pairwise comparison of the sequences of one data set to the sequences from another data set.

During the pairwise comparison process, all of the nucleotide sequences of one data set are compared individually to all of the nucleotide sequences of another data set. When both of the data sets are small and can be completely stored into the volatile memory of a computing device, it is reasonably efficient to pass nucleotide sequences of the data sets from storage on a nonvolatile memory device, such as a hard disk, to the volatile memory of the computing device to make the pairwise comparisons.

However, automated sequencing devices may potentially generate enormous data sets containing large numbers of nucleotide sequences that typically are stored in nonvolatile memory during the genome assembly process. Conventional gene assembly systems process entire data sets in a single operation, requiring careful management of the transfer of nucleotide sequence data from nonvolatile memory to volatile memory for processing. However, despite the measures taken to minimize processing times, conventional gene assembly systems typically have long processing times. For example, typical existing techniques organize the pairwise comparison of sequences in a raster-type scan, which requires a great deal of computational overhead for larger data sets. Advanced computational systems with large volumes of volatile memory operating at maximum capacity and a large time frame are typically required to assemble such large data sets.

SUMMARY

In one embodiment, a layout assembly system automatically assembles a genomic nucleotide sequence. The layout assembly system includes memory that contains a read sequence set, a comparing sequence set, and one or more modules configured to execute on at least one processor.

The read set includes a plurality of read entries. Each read entry includes a read sequence and a read sequence index assigned to identify the read sequence. The read sequence includes a first sequence of nucleotides.

The comparing sequence set includes one or more comparing entries. Each comparing entry includes a comparing sequence and a comparing sequence index assigned to identify the comparing sequence. The comparing sequence includes a second sequence of nucleotides.

The one or more modules include a mer generating and sorting system, a hit determination system, a hit table sorting system, a hit table condensing system, and a post processing system.

The mer generating and sorting system includes a sequence preprocessing system, a cmer generation system, and a mer sorting system. The sequence preprocessing system divides one or more read mers from each read sequence, assigns to each read mer the read sequence index corresponding to the read sequence from which the read mer was divided, assigns a read position index to each read mer identifying a number of nucleotides from a location within the read sequence from which the read mer was divided and assigns a read strand index to each read mer identifying each read mer as a forward sequence or a reverse sequence. Each read mer includes at least one of a first sequence of nucleotides. The sequence preprocessing system also generates a plurality of read mer table entries that each include one read mer, the read sequence index assigned to the one read mer, the read position index assigned to the one read mer, and the read strand index assigned to the one read mer. The sequence preprocessing system generates a read mer table that includes each read mer table entry.

The sequence preprocessing system also divides one or more comparing mers from each comparing sequence, assigns to each comparing mer the comparing sequence index corresponding to the comparing sequence from which the comparing mer was divided, assigns a comparing position index to each comparing mer identifying a number of nucleotides from a location within the comparing sequence from which the comparing mer was divided and assigns a comparing strand index to each comparing mer identifying each comparing mer as a forward sequence or a reverse sequence. Each comparing mer includes at least one of the second sequences of nucleotides. The sequence preprocessing system also generates a plurality of comparing mer table entries that each includes one comparing mer, the comparing sequence index assigned to the one comparing mer, the comparing position index assigned to the one comparing mer, and the comparing strand index assigned to the one comparing mer. The sequence preprocessing system generates a comparing mer table that includes each comparing mer table entry.

The cmer generation system replaces each read mer that includes a pyrimidine central nucleotide with a first reverse complement. The pyrimidine central nucleotide is a nucleotide located at the same distance from a first nucleotide of the read mer and a last nucleotide of the read mer. The pyrimidine central nucleotide may be cytosine, thymine, or uracil. The first reverse complement is a third sequence of nucleotides. Each third sequence nucleotide is the complement of a first corresponding nucleotide of the first nucleotide sequence arranged in reverse order. Similarly, the cmer generation system replaces each comparing mer comprising the pyrimidine central nucleotide with a second reverse complement. The second reverse complement is a fourth sequence of nucleotides in which each fourth sequence nucleotide is the complement of a second corresponding nucleotide of the second nucleotide sequence arranged in reverse order.

The mer sorting system sorts the one or more read mer table entries by the read mer, and sorts the one or more comparing mer table entries by the comparing mer.

The hit determination system identifies each match between the comparing mers and the read mers and generates a hit table entry for each match. Each hit table entry includes the comparing sequence index corresponding to a matching comparing mer, the read sequence index corresponding to a matching read mer, an orientation index assigned to identify an orientation of the matching comparing mer and the matching read mer as a same orientation or an opposite orientation, and a frameshift assigned to identify a third number of nucleotides to shift the read sequence corresponding to the matching read mer along the comparing sequence to align the matching read mer to the matching comparing mer. The hit determination system also generates a hit table that contains each hit table entry.

The hit table sorting system sorts the hit table entries by the comparing sequence index, sorts the hit table entries having a same comparing sequence index by the read sequence index, sorts the hit table entries having the same comparing sequence index and the same read sequence index by the orientation index, and sorts the hit table entries having the same comparing sequence index, the same read sequence index, and the same orientation index by the frameshift.

The hit table condensing system determines a score for each match between one hit table entry and one or more other hit table entries. The score is a total count of each match. The hit table condensing system creates a condensed hit table entry for each match that includes the one hit table entry and the score, and generates a condensed hit table that contains each condensed hit table entry.

In another embodiment, the layout assembly system is used to rapidly search large sequence databases, such as the National Center for BioInformatic's (NCBI's) non-redundant (nr) database, with an arbitrarily large set of query sequences. Existing tools, such as NCBI's nucleotide BLAST (Basic Local Alignment Tool), perform searches one at a time in a serial fashion and therefore, are ill suited for batch processing of large numbers of queries. In this application of the layout assembly system, the read sequence consists of an arbitrarily large set of query sequences, which may be an in silico predicted set of all genes in a newly assembled genome or a collection of sequence reads from an uncharacterized environmental sample and the comparing sequence is comprised of a sequence database (such as the nr database). The mer generating and sorting system, hit determination system, hit table sorting system, hit table condensing system, and post processing system are capable of determining the best match(es) for each entry in the read sequence set with those in the comparing sequence, producing a BLAST-like output. However, because all the queries are processed together, there are dramatic performance improvements over existing implementations of BLAST, especially for large query sets.

The post processing system generates an output file that may include the condensed hit table or a BLAST-like series of alignments, depending on the embodiment.

BRIEF DESCRIPTION OF DRAWINGS

FIG. 48 is an example of the BLAST-like alignment output produced by the database search tool. The header contains basic information (e.g. name, length in nucleotides, entry ID) on the sequence set 1 entry ("Query") and matching sequence set 2 database entry ("Template" or "Sbjct"). The Alignment section contains the matching region of Query and Sbjct sequences including the corresponding coordinates for both sequences. Pipes between sequences indicate identity at that position. The Alignment Statistics section contains absolute numbers of matches, mismatches and gaps as well as a bit score ("Score") and expectation value ("Expect"). The bit score is a normalized value calculated from the raw score and is expressed in units of bits, a common measure in information theory. The expectation value is used to estimate the probability of obtaining the observed alignment score with two random sequences. Expectation values are less sensitive to length than bit scores and are therefore generally a better measure of alignment quality.

DETAILED DESCRIPTION

Overview

Figure 1:
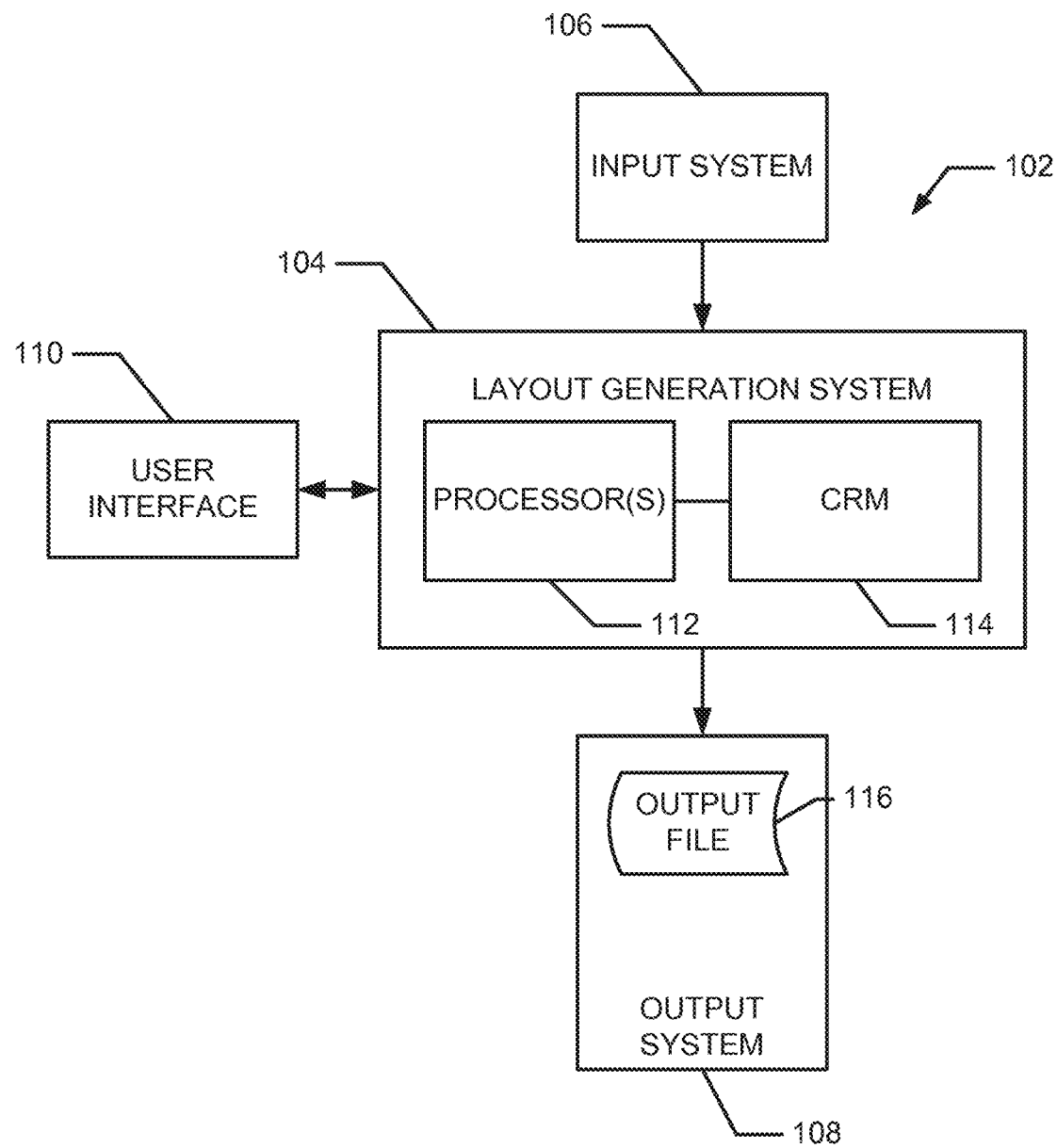
FIG. 1 is a block diagram of a layout assembly system in accordance with an embodiment of the present invention.

Systems and methods of the present invention may be used to match the nucleotide sequences of a first sequence set (sequence set 1) to each other, or to match the nucleotide sequences of the first sequence set to the nucleotide sequences of a second sequence set (sequence set 2), which may be used as a template. A sequence set has one or more sequences, and each sequence contains one or more nucleotides. A sequence set optionally may include information identifying the sequences.

The sequences in each sequence set are divided into mers, where each mer may be a subset of a sequence in one of the sequence sets. As the mers are formed, two or more indices are assigned to each of the mers to identify the particular nucleotide sequence from which the mer originated, as well as the location of the mer's sequence of nucleotides within the larger nucleotide sequence. The mers from each sequence set are assembled into a respective mer table along with their associated indices. In one aspect, the mers from each sequence set may be assembled into one mer table, along with their associated indices.

Because the nucleotide sequences of the sequence sets may originate from double-stranded DNA samples, some of the mers may have originated from forward-directed strands and other mers may have originated from reverse-directed strands. The mers in each mer table are processed to generate strand-independent mer tables that remove the effects of the direction of the sequences from subsequent processing.

In one aspect, two strand-independent mer tables are stored in nonvolatile memory. Each of the mer tables is sorted to arrange the mers in ascending or descending order, resulting in the mer table entries with the same mer nucleotide sequence being grouped together in the first sorted mer table and the second sorted mer table. In an aspect, the mers of both tables are the same length to facilitate a pairwise comparison of the mers from the first sorted mer table (table 1) and the mers from the second sorted mer table (table 2).

In another aspect, one strand-independent mer table containing the mers from two or more sequence sets is stored in nonvolatile memory. The mer table is sorted to arrange the mers in ascending or descending order. Each group of mer table entries having the same mer are sorted to arrange each group into two or more subgroups, where each subgroup contains the mer table entries corresponding to one sequence set from which the mers originated.

The mers from each sorted mer table are compared pairwise. Each match between the mers is recorded as an entry in a hit table that contains indices identifying the sequences from which each matched mer originated, the location of each mer within its originating sequence, and a frameshift index that specifies a number of nucleotides to shift the first sequence along the second sequence to align the segments of the sequences from which the matched mers were derived.

During processing, the mer table entries from the two sorted mer tables may be transferred from nonvolatile memory to volatile memory for the pairwise matching in one aspect. Because of the sorted arrangement of the mer table entries, small subsets of the sorted mer tables can be loaded into volatile memory from nonvolatile memory to compare the nucleotide sequences of the mers. In one aspect, a first group of mer table entries from a first mer table having the same mer sequence is transferred from nonvolatile memory to volatile memory for processing. Similarly, only a first group of mer table entries from a comparing table having the same mer sequence is transferred from nonvolatile memory to volatile memory for pairwise matching. When the next groups of mers from the sorted mer tables are obtained for subsequent pairwise matching, each of the mer tables are read starting at the entry following the last entries used in the previous pairwise comparison. In this aspect, the entries of the sorted mer tables are read a single time in one direction, minimizing the processing time spent locating and transferring the mer table entries of the sorted mer tables from nonvolatile memory to volatile memory. In addition, only those table entries required for the comparison are transferred from nonvolatile memory to volatile memory for pairwise comparison, which reduces the amount of volatile memory used for the pairwise comparison process.

Reading and processing groups of mer table entries during the pairwise comparison process greatly reduces the processing time relative to existing assembly methods that require one of the sequence sets to be loaded in its entirety into volatile memory for processing. Because only those mers that actually match are read from the nonvolatile memory into volatile memory for pairwise comparison and matching, the amount of volatile memory required to assemble a nucleotide sequence set using the layout assembly system is greatly reduced relative to the amount of volatile memory required by existing assembly methods. In addition, because the assembly methods of the layout assembly system are not limited by volatile memory capacity, the maximum size of the mer tables that may be processed by the layout assembly system is limited only by nonvolatile memory capacity, which is much larger than volatile memory capacity.

Depending on the type of sequence data and the desired outcome of the assembly process, the entries of the hit table may be analyzed using different processes. For example, the sequences in a first sequence set may be derived from a deoxyribonucleic acid (DNA) sample taken from a patient, and the sequences in a second sequence set may be a set of comparing genes related to a disease state. In this example, the entries of the hit table may be assessed to determine the degree of matching between the patient's sequences and the sequences of the comparing genes to diagnose the patient. In another example, the sequences in the first sequence set may be derived from a messenger ribonucleic acid (mRNA) sample, and the sequences in the second sequence set may be derived from a set of RNA sequences associated with the expression of a particular gene in an organism. In this example, the matches in the hit table may be used to determine the degree of expression of one or more genes in an organism.

Layout Assembly System Overview

FIG. 1 is a block diagram of an exemplary layout assembly system 102. The layout assembly system 102 includes a layout generation system 104, an input system 106, an output system 108, and a user interface 110.

The layout generation system 104 processes the one or more sequence sets, each having one or more sequences, identifies matches between one or more of the sequences from one or more of the sequence sets and one or more of the sequences from one or more of the other sequence sets, and generates a hit table that is a summary of the matches. In some instances, the matches may be used to assemble the sequences of one or more of the sequence sets into a longer continuous nucleotide sequence. In some instances, the results of the processing are written to an output file 116 in the output system 108. For example, the arrangement of sequences in a sequence set may be written to the output file 116. The layout generation system 104 may generate information to the user interface 110, including the status of the layout assembly process, results such as the output file 116, or queries for system input.

The layout generation system 104 includes one or more processors 112 and volatile and/or nonvolatile memory and can be embodied by or in one or more distributed or integrated components or systems. The layout generation system 104 may include computer readable media (CRM) 114 on which one or more algorithms, software, modules, data, computer readable instructions, and/or firmware is loaded and/or operates and/or which operates on the one or more processors 112 to implement the systems and methods identified herein. The computer readable media 114 may include volatile media, nonvolatile media, removable media, non-removable media, and/or other media or mediums that can be accessed by a general purpose or special purpose computing device. For example, computer readable media 114 may include computer storage media and communication media, including computer readable media. Computer storage media further may include volatile, nonvolatile, removable, and/or non-removable media implemented in a method or technology for storage of information, such as computer readable instructions, data structures, program modules, and/or other data. Communication media may, for example, embody computer readable instructions, data structures, program modules, algorithms, and/or other data, including as or in a modulated data signal. The communication media may include an information delivery system. The communication media may include wired and/or wireless connections and technologies and may be used to transmit and/or receive wired or wireless communications. Combinations and/or sub-combinations of the systems, components, modules, and methods and processes described herein may be made.

The input system 106 includes one or more devices or systems used to generate or transfer an electronic version of one or more sequences or sequence sets and/or other inputs and data to the layout generation system 104. The input system 106 may include, for example, a hard disk that stores input files that are read by or transferred to the layout generation system 104. The input system 106 also may include a storage system that stores electronic data, such as electronic data files. The input system 106 also may be one or more processing systems and/or communication systems that transmit and/or receive electronic files and/or other electronic document information or data through wireless and/or wire line communication systems, and/or other data to the layout generation system 104. The input system 106 further may include one or more processors, a computer, volatile and/or nonvolatile memory, computer readable media, a mouse, a trackball, touch pad, or other pointer, a key board, another data entry device or system, another input device or system, a user interface for entering data or instructions, and/or a combination of the foregoing. The input system 106 may be embodied by or in or operate using one or more processors or processing systems, one or more distributed or integrated systems, and/or computer readable media. The input system 106 is optional for some embodiments.

Examples of nonvolatile memory include nonvolatile read-only memory, flash memory, and magnetic and/or optical storage devices, such as hard disks, floppy disks, magnetic tape, and optical discs. Other examples of nonvolatile memory exist. Examples of volatile memory include random access memory, such as SRAM and DRAM. Other examples of volatile memory exist.

The output system 108 includes one or more systems or devices that receive, display, and/or store data. The output system 108 may include a communication system that communicates data with another system or component. The output system 108 may be a storage system that temporarily and/or permanently stores data, such as input files, intermediate data tables generated by the layout generation system, output files, and/or other data. The output system 108 also may include a computer, one or more processors, one or more processing systems, or one or more processes that further process data. The output system 108 may otherwise include a monitor or other display device, a computer, a printer, another data output device, volatile and/or nonvolatile memory, other output devices, computer readable media, a user interface for displaying data, and/or a combination of the foregoing. The output system 108 may receive and/or transmit data through a wireless and/or wire line communication system. The output system 108 may be embodied by or in or operate using one or more processors or processing systems, one or more distributed or integrated systems, and/or computer readable media. The output system 108 is optional for some embodiments.

The user interface 110 receives one or more inputs from a user and/or generates data for display to a user. The user interface 110 includes one or more systems or devices that receive, transmit, display, and/or store data of the layout assembly system 102. The user interface 110 may include a monitor or other display device, a keyboard, mouse, or other input device, one or more processors, a computer, a printer, and/or a combination of the foregoing.

Layout Assembly System

Figure 2:
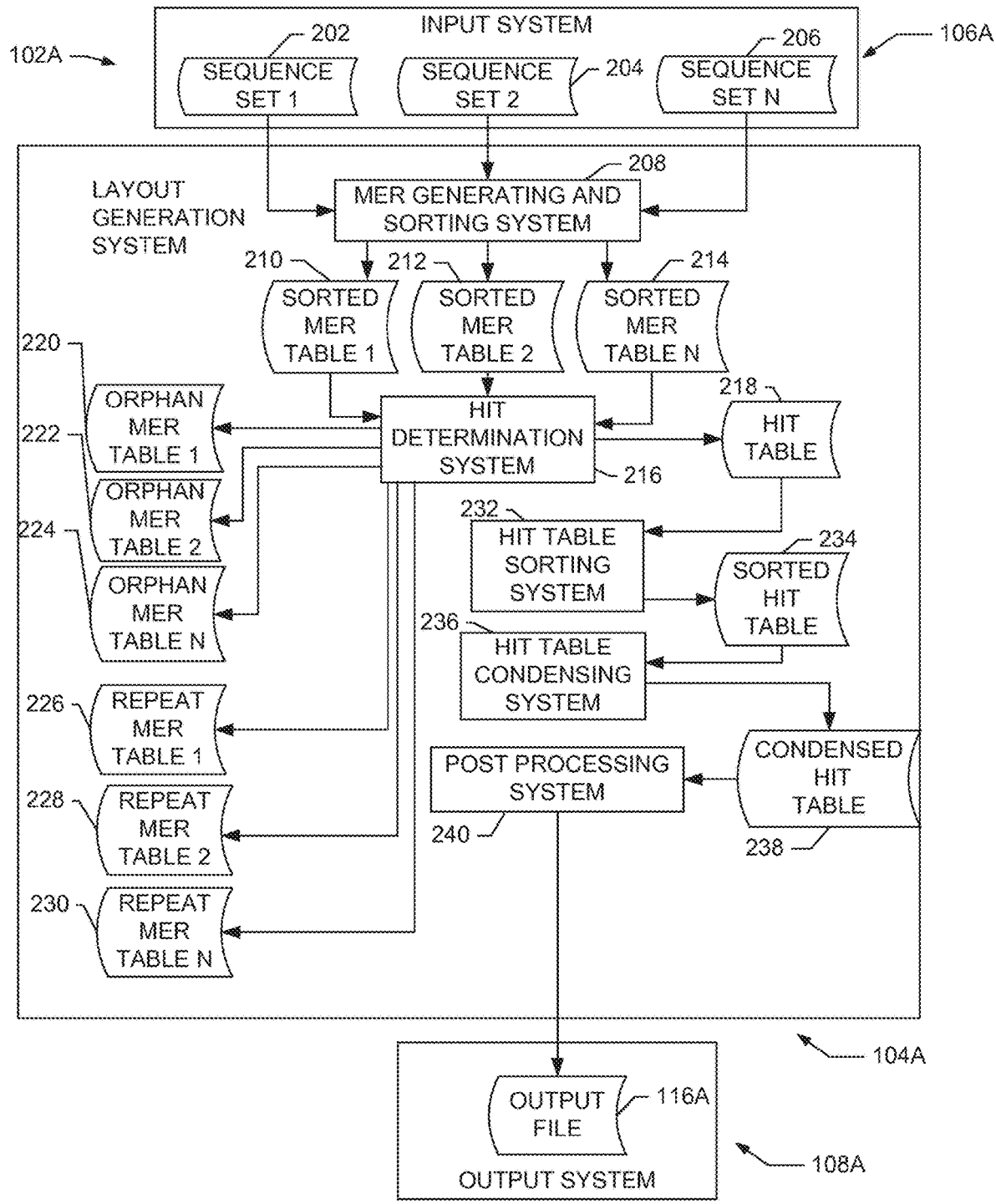
FIG. 2 is a block diagram of a layout assembly system in accordance with an embodiment of the present invention.

FIG. 2 is a block diagram of an exemplary layout assembly system 102A for automatically assembling a nucleotide sequence, such as a genome. The layout assembly system 102A includes an input system 106A that stores one or more sequence sets 202-206 in nonvolatile memory. The layout assembly system 102A also includes a layout generation system 104A that retrieves or receives sequence sets from the input system 106A, processes the sequence sets to determine matches, and then generates two more entries for the matches. In some instances, the layout assembly system 102A stores the entries for the matches in an output file 116A in the output system 108A. One example of an output system 108A is a hard disk that stores the output file 102A.

The layout generation system 104A matches one of the sequence sets 202-206 to one or more other sequence sets. Each of the sequence sets 202-206 includes one or more nucleotide sequences and, optionally, information identifying the sequences. Each of the nucleotide sequences contains one or more nucleotides. In one example, two sequence sets 202-204 are processed. In another example, one sequence set 202 is processed. In another example, N sequence sets 202-206 are processed, where N is a number greater than 2. In another example, sequence set 1 202 is a read sequence set containing one or more read sequences. A read sequence may be a nucleotide sequence resulting from the analysis of a fragment of genetic material by an automated sequencing device. Examples of genetic material include deoxyribonucleic acid (DNA), messenger ribonucleic acid (mRNA), ribosomal ribonucleic acid (rRNA), and transfer ribonucleic acid (tRNA). Other examples exist. In this example, sequence set 2 204 is a comparing sequence set, which is a sequence set that is compared to the read sequence set to identify the one or more matching sequences. In this example, sequence set 1 202 is assembled using sequence set 2 204 as a template.

In one aspect, one or more sequence sets 204 and/or 206 are used as a template to assemble the sequences of a first sequence set 202. In one aspect, the template sequences are previously analyzed and assembled nucleotide sequences. Examples of previously analyzed and assembled nucleotide sequences include genes of prokaryotes and eukaryotes, prokaryote and eukaryote genomes, and sequences listed in databases, such as the Human Genome Project database, the Human Gene Mutation Database, the Single Nucleotide Polymorphism database, the Haplotype Map, the Watson 454 genome database, and others. In another aspect, the template sequence set is a copy of the first sequence set 202, such as when the first sequence set is a novel sequence set with no existing template. In one aspect, the sequence set ranges in size from about 50 reads per set to about 100 million reads per set. In another aspect, the total size of a sequence set ranges from about $10^3$ nucleotides to about $10^{11}$ nucleotides per sequence set.

The layout generation system 104A includes modules to process the sequence sets 202-206. In the example of FIG. 2, the modules include a mer generating and sorting system 208, a hit determination system 216, a hit table sorting system 232, a hit table condensing system 236, and a post processing system 240. The modules may be stored on a CRM 114 or execute on one or more processors 112.

The mer generating and sorting system 208 divides each sequence of each sequence set 202-206 into one or more mers and generates a mer table entry for each mer. Each mer table entry includes one or more indices identifying the sequence from which the mer's nucleotides were divided and the location on the sequence from which the mer's nucleotides were divided. The mer generating and sorting system 208 generates a mer table for each sequence set 202-206 processed during a comparison and matching operation, which may include 1, 2, or N sequence sets. Alternately, the mer generating and sorting system 208 generates one mer table that includes mer table entries for each of the sequence sets processed during the comparison and matching operation. Each mer table is sorted by the mer generating and sorting system 208 by the nucleotide sequence to arrange its entries in mer nucleotide sequence order resulting in the sorted mer tables 210-214. The number of sorted mer tables generated by the mer generating and sorting system 208 corresponds to the number of mer tables and the number of sequence sets processed by the mer generating and sorting system. In one example, sequence sets 1 and 2 202-204 are processed and sorted mer tables 1 and 2 210-212 are generated by the mer generating and sorting system. In another example, a single sorted mer table is generated from a single mer table.

The hit determination system 216 pairwise compares the entries of one sorted mer table 210 to the entries of one or more other sorted mer tables 212-214. The hit determination system 216 identifies matches between mers and generates the entries of a hit table 218. A match between one mer and another mer occurs when each of the nucleotides within the one mer occur in the same order as each of the nucleotides within the other mer. In one example, the hit determination system 216 pairwise compares the mers from a sorted mer table 1 210 to the mers of a sorted mer table 2 212. In one example, the sorted mer table 1 210 is a sorted read mer table, and the sorted mer table 2 212 is a sorted comparing mer table.

Each of the hit table entries contain one or more indices, including a sequence set index 1, a sequence set index 2, a sequence index 1, a sequence index 2, a position index 1, a position index 2, a strand index 1, a strand index 2, an orientation index, and a frameshift. The sequence set index 1 and sequence index 2 identify the originating sequence sets of the matched mers. The sequence index 1 and sequence index 2 identify the originating sequences of each matched mer. The position index 1 and position index 2 identify locations in the originating sequences of a selected nucleotide in the matched mers. The strand index 1 and strand index 2 identify whether the matched mers correspond to forward originating sequences or reverse originating sequences. The orientation index specifies whether the matched mers were oriented in the same direction or in the opposite direction relative to each other. The frameshift identifies a number of nucleotides that the originating sequence of one matched mer must be shifted down the originating sequence of the other matched mer to align the nucleotides of both mers. The originating sequence is the sequence from which the mer was divided. Similarly, the originating sequence set is the sequence set containing the originating sequence.

In one aspect, if there are any mers in the sorted mer tables 210-214 that do not match a corresponding mer in one or more other sorted mer tables, the hit table determination system 216 places the mer table entries corresponding to the non-matched mers into orphan mer tables 220-224. For example, mer table entries corresponding to non-matched mers from sorted mer table 1 210 are placed in orphan mer table 1 220, and mer table entries corresponding to non-matched mers from sorted mer table 2 212 are placed in an orphan mer table 2 222. In another aspect, one orphan mer table holds mer table entries for all non-matched mers from all mer tables processed by the hit determination system 216.

Overly repeated matches between mers from the sorted mer tables 210-214 and 212 may not be informative to the nucleotide assembly process in one aspect. A group of mer matches may be identified as overly repeated if the number of mer matches in the group exceeds a user-defined repeated mer threshold. In this aspect, mer table entries for these overly repeated mer matches are placed into repeat mer tables 226-230. For example, mer table entries from overly repeated mer matches from sorted mer table 1 210 are placed into repeat mer table 1 226, and mer table entries from overly repeated mer matches from mer table 2 212 are placed into repeat mer table 2 228. Alternately, one repeat mer table holds mer table entries for all overly repeated mer matches.

The hit table sorting system 232 sorts the hit table entries of the hit table 218 to group together entries that include mers derived from the same sequence index 2 (second sequence index group) in the sequence set 2 204. The hit table sorting system 232 further sorts the hit table entries so that the hit table entries that include mers derived from the same sequence index 1 (first sequence index group) in sequence set 1 202 are placed together within each second sequence index group. The hit table sorting system 232 further sorts the hit table entries so that the hit table entries that include the same orientation index (orientation index group) are placed together within each first sequence index group. The hit table sorting system 232 further sorts the hit table entries so that the hit table entries that include the same frameshift (frameshift group) are placed together within each orientation index group. The hit table sorting system 232 further sorts the hit table entries so that the hit table entries that include the same position index 2 (position index group) are placed together within each frameshift group. After sorting the hit table entries of the hit table 218, the hit table sorting system 232 transfers the hit table entries into a sorted hit table 234.

The hit table condensing system 236 compares the entries of the sorted hit table 234 to identify repeated hit table entries, which are hit table entries having at least one other hit table entry in the same position index 2 group. The hit table condensing system 236 generates a condensed hit table entry for each set of repeated hit table entries that includes one instance of the repeated hit table entry and an index containing the number of repeated entries. The hit table condensing system 236 transfers all of the condensed hit table entries into a condensed hit table 238. In one aspect, the hit table condensing system 236 is modified and exists in a different form from the layout generation system 104. In another aspect, the hit table condensing system 236 is excluded from the layout generation system 104, and the post processing system 240 instead processes a sorted hit table 234, as explained below.

The layout generation system 104 also includes a post processing system 240 that processes the entries of the condensed hit table 238. In one aspect, the entries of the condensed hit table 238 are processed to assemble a sequence set 202 into a longer nucleotide sequence. Examples of longer nucleotide sequences include a gene, a chromosome, and a genome. Other examples exist. In another aspect, the entries of the condensed hit table 238 are processed to determine the expression of a particular gene product. The post processing system 240 may process the entries of the condensed hit table 238 using one or more post processing algorithms. The particular post processing algorithm used is selected based on the type of data contained within one or more sequence sets 202-206 being processed, as well as the desired information to be obtained from the layout assembly system 102A. In one example, if the sequence set 1 202 is a DNA sample from a patient, and the sequence set 2 204 is a set of nucleotide sequences from a previously assembled human genome, the desired result may be to generate an assembled genome for the patient by determining the most likely arrangement of the nucleotide sequences of the sequence set 1 onto the nucleotide sequences of sequence set 2 204.

Sequence Set

Figure 3:
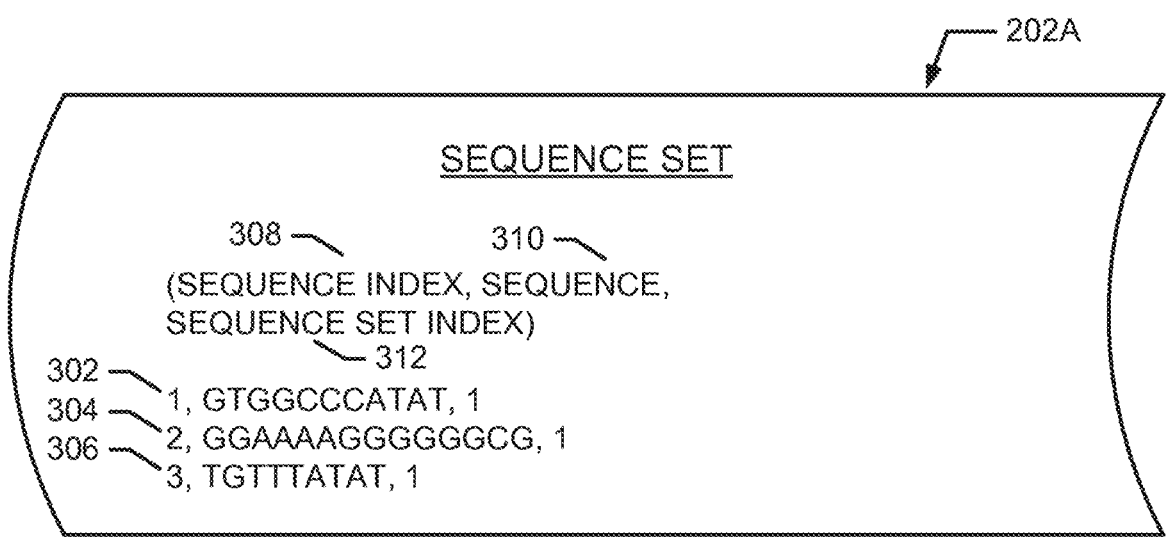
FIG. 3 is a diagram of a sequence set in accordance with an embodiment of the present invention. The sequence set shown includes three sequence set entries, each containing a sequence index, an exemplary sequence, and a sequence set index. The three exemplary sequences are GTGGC-CATAT (SEQ. ID NO: 1), GGAAAAGGGGGCG (SEQ. ID NO:2), AND TGTTTATAT. These exemplary sequences are fictitious and are provided to illustrate the methods of an embodiment of the present invention.

A sequence set is one or more sequence entries, where each sequence entry includes a sequence with one or more nucleotides and information identifying the sequence. FIG. 3 shows an exemplary sequence set 202A. The sequence set 202A contains one or more sequence entries 302-306. Each sequence entry 302-306 contains a sequence index 308, a sequence 310, and a sequence set index 312.

The sequence index 308 is a number assigned to each sequence 310 to uniquely identify each sequence 310. For example, as the sequence set 202A is divided into mers and further processed, the sequence index 308 may be included with the processed data to specify the location in the sequence set 202A from which the data was derived.

The sequence 310 is a string of one or more nucleotides. For example, the sequence 310 may be a read sequence or a sequence from a genetic database. In one example, the sequence 310 is encoded as a series of letters, for example ATGC, corresponding to the nucleotide bases of the sequence. In another example, the nucleotide bases are encoded as binary numbers using symmetric bit coding or symmetric fitch coding. In symmetric bit coding, A is encoded as 11, G is encoded as 10, C is encoded as 01, and T is encoded as 00. In symmetric fitch coding, A is encoded as 1000, G is encoded as 0100, C is encoded as 0010, and T is encoded as 0001. Other examples exist.

The sequence set index 312 is an integer assigned to each entry to identify the sequence set from which the sequence 310 originated. In an aspect, the sequence set index is included with data resulting from the processing of one or more sequences from a sequence set 202 to identify the sequence set 202 from which the data were derived.

All or a portion of the sequence entries 302-306 are alphanumeric data, integers, hexadecimal numbers, binary numbers, or another data encoding convention. Other examples exist.

Other forms and formats of the sequence sets 202-206 may be used, and the order of the indices 308-312 may be changed.

Mer Generating and Sorting System

Figure 4:
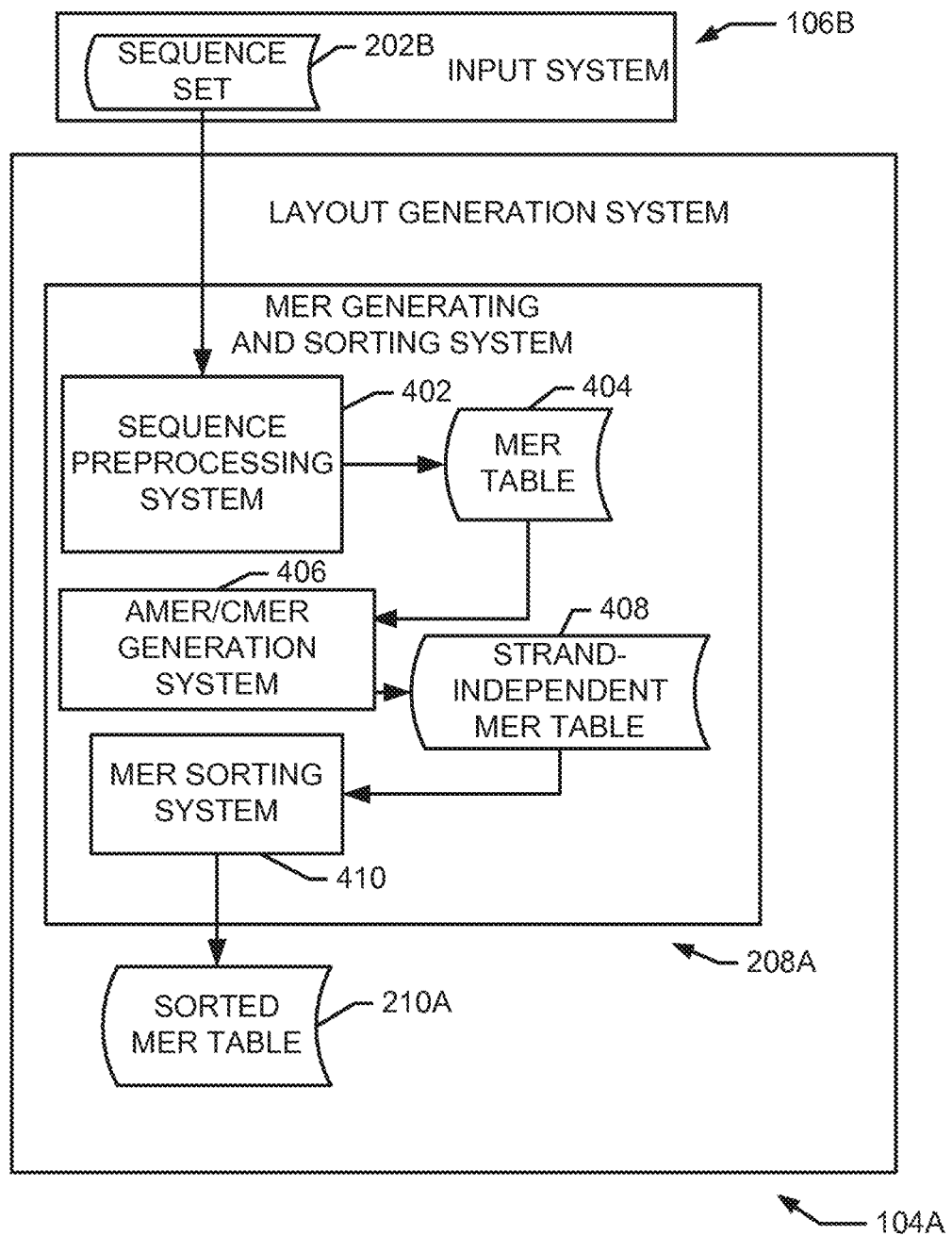
FIG. 4 is a block diagram of a mer generating and sorting system in accordance with an embodiment of the present invention.

FIG. 4 shows a block diagram of an exemplary mer generating and sorting system 208A. The mer generating and sorting system 208 reads in or receives a sequence set 202 from the input system 106, divides one or more sequences of the sequence set into one or more mers, processes the mers to remove the effect of nucleotide strand orientation, and places the mers in order of mer nucleotide sequence into a sorted mer table 210A.

The sequence processing system 402 reads in or otherwise receives each of the sequence entries of the sequence set 202B and divides each sequence into the mers. The sequence processing system 402 assigns one or more indices to each mer to identify the location within the sequence and sequence set 202B from which the mer was divided. The sequence processing system 402 generates a mer table entry for each mer, and each mer table entry includes the mer, the sequence index, a position index, a strand index, and the sequence set index. The sequence index and the sequence set index are the indices previously assigned to the sequence and sequence set from which the mer was divided. The position index is a number identifying a location in the originating sequence of a selected nucleotide in the mer. The strand index is a number that specifies whether the mer is derived from a forward originating sequence or a reverse originating sequence. In one aspect, a strand index of "1" indicates that the mer was derived from a forward nucleotide sequence, and a strand index of "2" indicates that the mer was derived from a reverse nucleotide sequence. Other numbers, flags, or indicators may be used. The sequence processing system 402 assembles each of the mer table entries into the mer table 404.

The amer/cmer generation system 406 removes the potentially confounding effect of the direction of the nucleotide strand from which the mers were derived. In one aspect, the nucleotide sequence of each mer is used to generate the reverse complement nucleotide sequence. The mer is then compared to its corresponding reverse complement, and one or the other or neither is retained according to one or more rules (identified below). In one aspect, the same rule is applied to all mer tables consistently. The mer or its reverse complement is then reassigned to the location indices to form a strand-independent mer table entry. The amer/cmer generation system assembles the one or more amer/cmer table entries derived from the entries of the mer table 404 into a strand-independent mer table 408.

The mer sorting system 410 sorts the entries of the strand-independent mer table by the mer nucleotide sequences to generate a sorted mer table 210A.

Sequence Preprocessing System

Figure 5A:
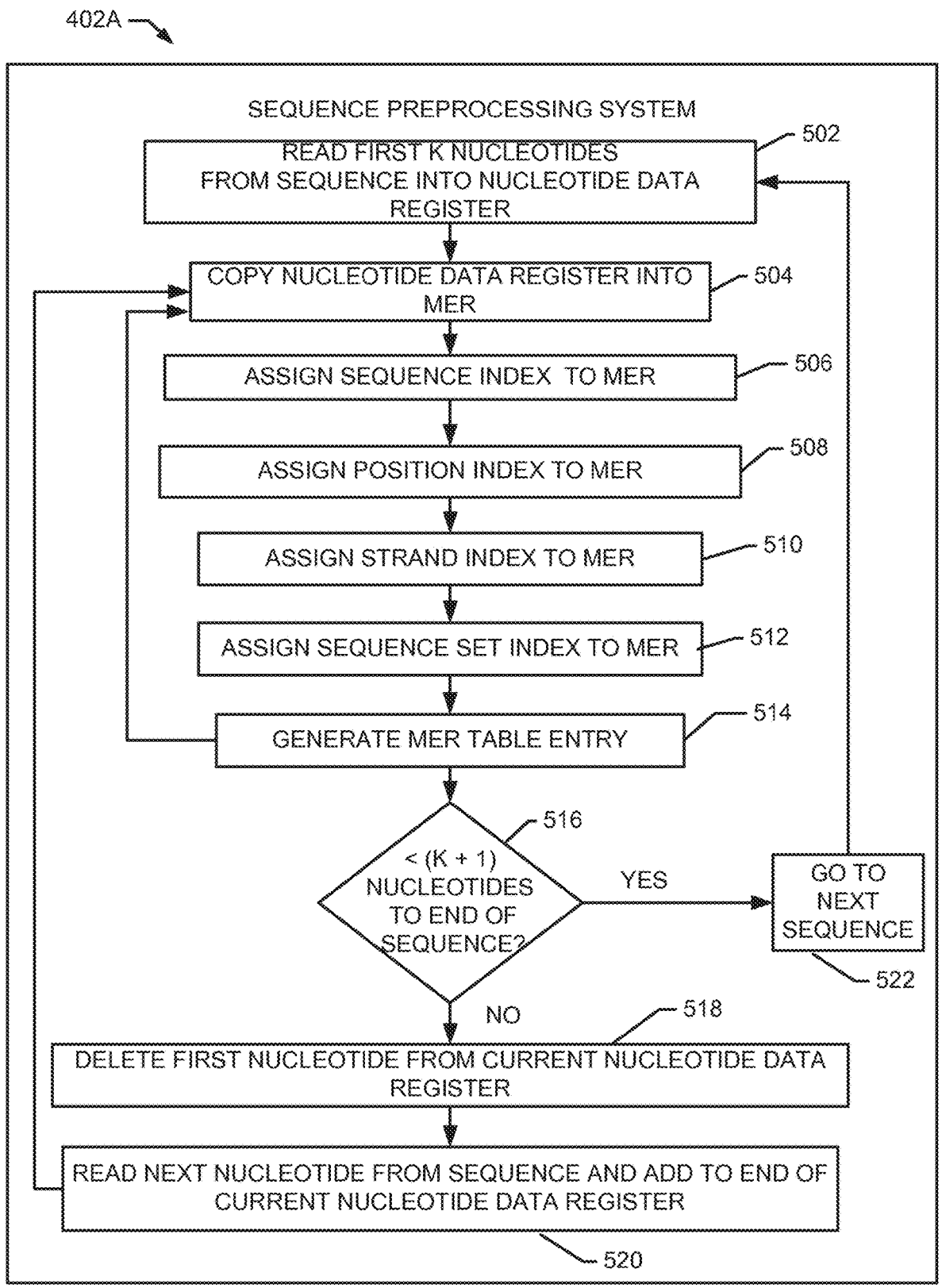
FIG. 5A is a block diagram of a sequence preprocessing system in accordance with an embodiment of the present invention.

FIG. 5A is a flow chart showing the mer generation process of an exemplary sequence preprocessing system 402A. The sequence preprocessing system 402A divides each sequence of the sequence set 202 into the mers, assigns the indices to specify the location of the mers within the originating sequence, and generates a mer table 404A containing the mer table entries.

As discussed above, a mer is a shorter nucleotide sequence divided out of a longer sequence. The length of each mer is less than or equal to the length of the shortest sequence length among all of the sequences of all of the sequence sets 202-206 to be processed. In addition, the length of the mers may be based on other factors, including the estimated frequency of sequencing errors, the estimated frequency of single nucleotide polymorphisms (SNPs) in the sequences, and the desired processing time to assemble the sequence set into at least one longer nucleotide sequence. Other factors may exist. Shorter mers increase the likelihood of capturing regions of the sequences that do not contain sequencing errors or SNPs, but shorter mers also increase the total number of mers to be processed by the layout assembly system, resulting in a longer processing time. In addition, shorter mers may have a higher chance of introducing random matches that are not indicative of any homology. Thus, these factors are balanced by the layout assembly system. In one example, a mer is between about 2 and about 100 nucleotides long. In another example, a mer is about 19, 20, or 21 nucleotides long.

The sequence preprocessing system 402A reads in the first K nucleotides of a sequence from a sequence set, such as sequence set 1 202, into the nucleotide data register at step 502 and copies the nucleotide data to the mer at step 504. K is a number that specifies the length of the mers.

As shown at steps 506-512, the sequence preprocessing system 402A assigns the sequence index, a position index, a strand index, and a sequence set index to the mer. An entry for the mer table 404 is generated at step 514. The mer table entry includes the mer, the assigned sequence index, assigned position index, assigned strand index, and the assigned sequence set index. In one aspect, the sequence preprocessing system 402A assigns an initial value of 1 for the strand index, corresponding to a forward sequence. In this aspect, the final strand index is determined in the amer/cmer generation system 406.

The sequence preprocessing system 402A then determines whether less than K+1 nucleotides remain in the sequence at step 516. If there are at least K+1 nucleotides remaining in the sequence, the system deletes the first nucleotide from the nucleotide data register at step 518, then reads the next nucleotide from the sequence and appends the nucleotide to the end of the current nucleotide data at step 520. The nucleotide data assembled in step 520 is copied into the next mer table entry at step 504. The sequence preprocessing system 502A repeats steps 518-520 and 504-514 if K+1 or more nucleotides remain in the sequence at step 516. If less than K+1 nucleotides remain in the sequence, then too few nucleotides remain to form any additional mers, and the system advances to the next sequence in the set at step 522.

In one aspect, the sequence preprocessing system 402A creates mer table entries for all mers resulting from the mer generation process. In another aspect, the sequence preprocessing system 502A creates mer table entries for only a subset of mers that meet a specified inclusion criterion. In this aspect, the selection criterion is selected to reduce the total number of mers processed by the hit determination system 216 without significantly impacting the accuracy of the layout generation process.

In general, mers may include a subset of contiguous nucleotides divided out of a longer sequence, a subset of non-contiguous nucleotides divided out of a longer sequence based on a different pattern or rule, or a combination of contiguous and non-contiguous nucleotides. For example a mer may be formed by assembling every other nucleotide in a sequence, every third nucleotide in a sequence, or every sequence following a palindromic sequence. Other examples exist.

In an exemplary aspect, mers may be formed by selecting a subset of contiguous nucleotides and replacing any instances of repeating contiguous nucleotides with a single nucleotide that matches the repeating group. For example, a sequence that includes nucleotide C followed by string of ten repeats of the nucleotide A, followed by the nucleotide G would be replaced by the nucleotide sequence CAG. Mers that are formed in this manner are defined by "flowmers" in the context of the application. That is, a flowmer is a subset of a sequence of nucleotides in which repeated nucleotides are removed, eliminated, or otherwise not included, leaving a single instance of the repeated nucleotides. Methods of generating flowmers from nucleotide sequences and assembling the sequences into flowmer tables are discussed in detail below.

Figure 5B:
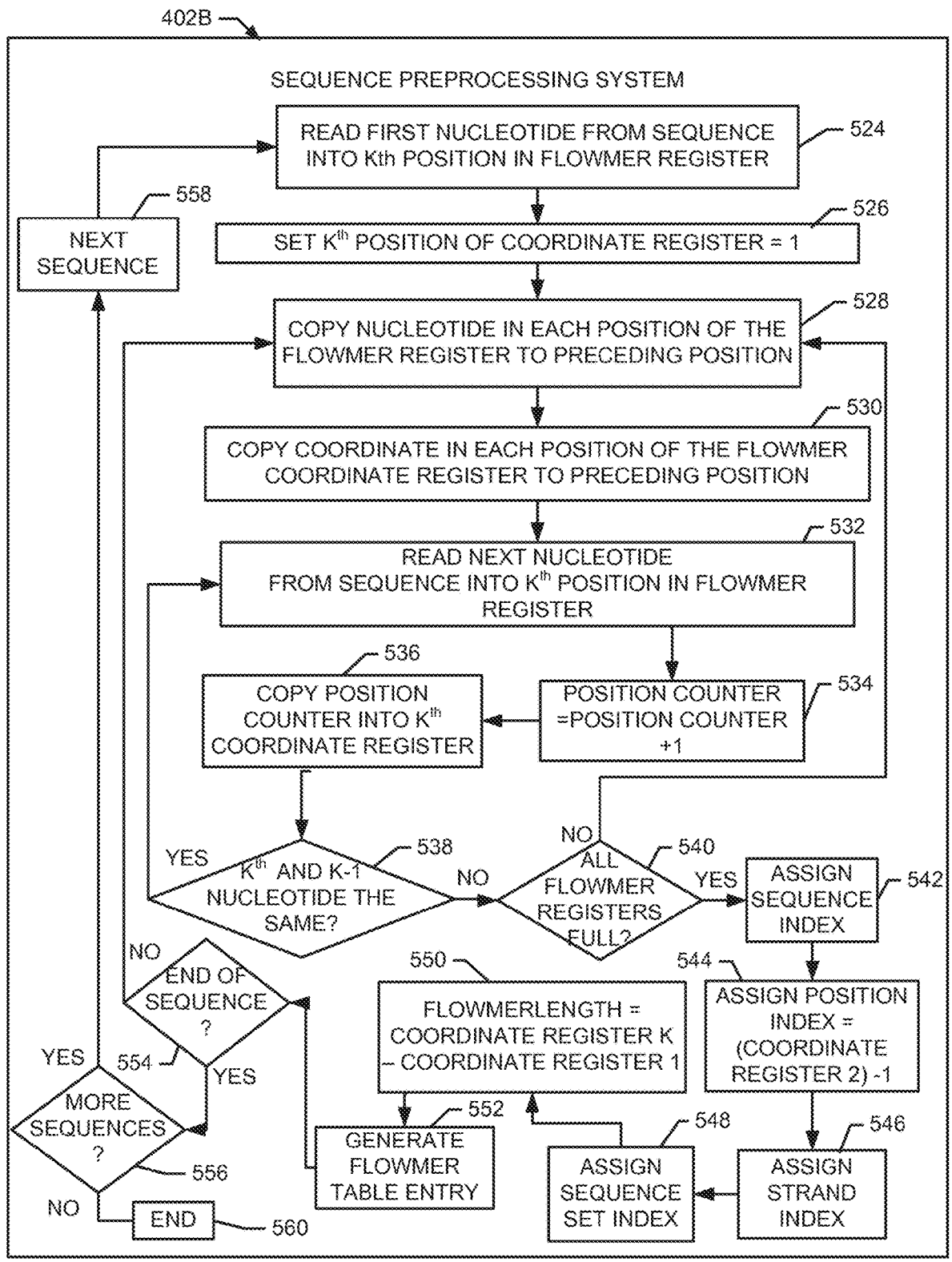
FIG. 5B is a block diagram of a sequence preprocessing system in accordance with another embodiment of the present invention.

An alternative sequence preprocessing system 402B for generating flowmers from a nucleotide sequence and for creating flowmer table entries is shown in FIG. 5B. In this aspect, nucleotides of the sequence are read into flowmer register one nucleotide at a time by the sequence preprocessing system 402B and evaluated for inclusion into a flowmer. As the nucleotides are read in, the position of each nucleotide included in a flowmer is saved in a coordinate register. Both the flowmer register and the coordinate register contain K entries corresponding to the K nucleotides to be included in each flowmer.

The first nucleotide of the sequence is read into the last ($K^{th}$) position in the flowmer register at step 524, and the $K^{th}$ position of the coordinate register is set to a value of 1 at step 526. Each nucleotide in the flowmer register is then shifted over one position at step 528 by copying the $K^{th}$ position nucleotide into the (K−1) position, the second position into the first position, and so on. Similarly, the coordinate register positions are shifted over one position at step 530 in a similar manner by copying the $K^{th}$ position coordinate into the (K−1) position coordinate and so on.

The next nucleotide in the sequence is then read into the $K^{th}$ position in the flowmer register at step 532. The position counter, tracking the nucleotide's position within the sequence is incremented by one at step 534, and this position counter is copied into the $K^{th}$ coordinate register at step 536. The Kth nucleotide in the flowmer register is compared to the K−1 nucleotide in the register at step 538. It the two nucleotides are the same, then the next nucleotide is read at step 532, and the process repeats until a $K^{th}$ nucleotide is read that is different from K+1 nucleotide at step 538.

When a non-repeating nucleotide is detected at step 538, the flowmer registers are checked to see if all registers are full at step 540. If the registers are not yet full at step 540, then more nucleotides need to be read into the register before a full-length mer can be generated. Steps 528-538 are repeated until the flowmer registers are full at step 540, indicating that a complete flowmer sequence has been identified.

A sequence index is assigned to the flowmer sequence at step 542, and a position index is determined by subtracting 1 from the coordinate of coordinate register position 2 at step 544. A strand index and a sequence set index are assigned to the flowmer sequence at steps 546 and 548 respectively. A flowmerlength is determined by subtracting the coordinate register in position K from position 1 at step 550, and a flowmer table entry is generated at step 552. If there are any remaining nucleotides to be read from the sequence at step 554, the registers of the flowmer and flowmer position registers are shifted in step 528 and 530 respectively to start the process of generating the next flowmer. This process repeats until no more nucleotides remain to be read in the sequence.

Once the end of a sequence is detected at step 554, if there are additional sequences at step 556, the next sequence is read at step 558 and the process repeats for each sequence in the sequence set. If no more sequences remain at step 556, the system ends processing at step 560.

The flowmerlength is a quantity that specifies the length of the subset of the sequence from which the flowmer was generated by removing repeating nucleotides. Because the flowmerlength includes the nucleotides that were removed, the number of nucleotides in the flowmer may be less than the flowmerlength. In addition, although each flowmer has the same specified length of K nucleotides, the flowmerlength may vary due to the variable number of repeating nucleotides that may be removed in the process of generating flowmers. In one example, if a flowmer that contains 15 nucleotides is generated by removing 40 repeating nucleotides from a sequence, the flowmerlength would be 55 nucleotides (15+40). In the special case in which a sequence from which the flowmer was generated has no repeating nucleotides, the flowmerlength would be equal to the number of nucleotides in the flowmer.

Except where otherwise specified below, the flowmers may be processed using essentially the same processing methods and assembly techniques as those used for mers containing subsets of contiguous nucleotides from the sequence. In general, within any of the discussions below, the terms "mer" and "flowmer" may be used interchangeably, unless specifically stated otherwise.

Mer Thinning and Mer Minimization

The efficiency of the layout generation system 104 may be lowered when relatively large volumes of sequencing data are analyzed. Each nucleotide in the data is effectively considered in K different mers and K different hits due to the overlapping nature of mers, where K is the total number of mers generated from all sequences of a sequence set. However, if some reduction in the number of mers, and the corresponding matches between mers is allowed, some mers may be dropped in a systematic manner, resulting in a considerable gain in efficiency. Ideally, the vast majority of droppedmers may well be redundant due to the overlapping nature of mers.

In one aspect, mer thinning may be used to reduce the quantity of mers included as entries in a mer table 404 by simply skipping mers and only retaining every $N^{th}$ mer only in the mer table entries. For a given value of N, where N is an integer specifying the mer thinning interval, an N-fold reduction in the number of mers to be included in the mer table entries is achieved. In one aspect, n is selected to be less than the length of any sequence in a sequence set. If N is less than the mer length K, then every nucleotide in each sequence of a sequence set is still included at least once in the reduced set of mers.

Mer thinning generally is not be performed on both the comparing sequence set and the read sequence set, because the criterion of retaining every $N^{th}$ mer generated from a sequence is a purely spatial selection criterion, in which the mers to be retained are selected based on their spatial position within a sequence. For example, retaining every Nth mer of each sequence in a sequence set imposes a very regular spatial pattern of mer retention on the sequences of the sequence set. However, the spatial positions between the read and comparing sequences may not be easily reconciled. In one aspect, the full set of comparing mers may be retained and the full set of read mers may be reduced using the mer thinning method, because typically the full set of read mers is much larger than the full set of comparing mers. The thinning interval n is selected to provide a subset of mers which incorporate the majority of nucleotides in all of the read sequences as completely as possible. Although mer thinning may render an inconsistent number of hits of different read sequences, each read sequence is internally consistent and therefore may be reasonably mapped on its own.

In another aspect, the quantity of mers included as entries in the mer tables may be reduced by a method of mer minimization. This method checks each mer against an internal pattern and eliminates those mers which do not match the pattern. In this aspect, the pattern used to select mers for inclusion in the mer tables may be a non-biased pattern. The non-biased pattern results in an approximately random selection of mers with respect to all sequences in the sequence set overall, and a sufficient number of mers per individual sequence to ensure the inclusion of the majority of nucleotides within each individual sequence during the layout assembly process. Non-limiting examples of a non-biased pattern include the selection of mers immediately following or containing an "A" nucleotide, a "C" nucleotide, a "T" nucleotide, or a "G" nucleotide; the selection of mers immediately following or containing a specified nucleotide sequence ranging between 2 and about 6 nucleotides in length; and the selection of mers immediately following a palindrome mer, in which the mer sequence is the same as the reverse complement sequence.

In another aspect, a non-biased pattern of bases may be derived from the analysis of a variety of genomes. A candidate pattern of mer minimization may be evaluated by assessing the amount of reduction in total mers using the candidate pattern. An approximately $4^n$-fold reduction of the number of mers may be achieved using a non-biased pattern, where 'n' is the number of bases included in the pattern.

Mer minimization methods may be applied to read mers, comparing mers, and to both read and comparing mers with minimal loss in the accuracy of the layout generation process, because the non-spatial mer selection criterion results in a consistent but random pattern of mers that is independent of the sequence from which the mers are derived. In yet another aspect, the non-biased pattern of bases used in the mer minimization method is selected to produce a sufficiently high frequency of occurrence of mers relative to the mer length and read length, resulting in a sufficient amount of mer data to accurately and quickly perform the mapping of read sequences to the comparing sequence.

In still another aspect, the number of mers in a mer table generated by the sequence preprocessing system 402A from a sequence set may be reduced by selecting one or more mertags, which are a subset of the set of all mers originating from a sequence set, based on a mertag selection criterion. Reducing the entries of a mer table reduces the length of time to assemble a sequence set by reducing the number of pairwise comparisons made during the mer matching process, reduces the number of hits in the hit table to be sorted and condensed, and reduces the number of condensed hit table entries to be processed by the post processing system. In this aspect, the mer table is processed to eliminate all mer table entries that do not include one of the mertags. In an embodiment, about 2 or 3 mertags are present in each sequence of a sequence set, the mertags are randomly distributed throughout the sequences of the sequence set, and the mertags are repeated between about 2 and 500 times within all of the sequences of a sequence set. Though, more than 3 mertags may exist.

The mertags may be selected by choosing every $n^{th}$ mer in a mer table, where n may range between 1 and about 100. In another aspect, the mertags may be selected by choosing every mer immediately following or containing an "A" nucleotide, a "C" nucleotide, a "T" nucleotide, or a "G" nucleotide in a mer table. In another aspect, the mertags may be selected by choosing every mer immediately following or containing a specified nucleotide sequence ranging between 2 and about 6 nucleotides in length. In another aspect, the mertags may be selected by choosing every mer immediately following a palindrome mer, in which the mer sequence is the same as the reverse complement sequence.

A list of potential mertags may be selected by choosing 3 mers at random from each sequence of the sequence set. The mertags are then selected by choosing all mers in the mer table that match an entry from the list of potential mertags. In addition, after all mertags have been selected, the separation of the mertags on each sequence of the sequence set (a mertag gap) may be determined.

If a mertag gap is detected, such as when the separation of two consecutive mertags on a sequence exceeds a threshold mertag separation, then additional mertags may be selected to fill in each mertag gap. In this aspect, the threshold mertag separation is a distance between the end of a mertag and the beginning of the next consecutive mertag on a sequence. For example, the threshold mertag separation may range between about one mer length and about 10 mer lengths. Also in this aspect, the mertags selected to fill in the mertag gap on all of the sequences of the sequence set may be selected by inspection by a user or selected by applying another rule, such as any one of the mertag selection rules described above. Once the additional mertags have been selected to fill in all mertag gaps detected in all sequences of the sequence set, all mer table entries from the complete mer table with mers matching the additional mertags may be added to the mertag table. Other examples exist.

In one aspect, the mertags are generated during the mer generation process. In another aspect, the mertags are selected from the mer tables generated by the sequence preprocessing system 502A.

Mer Table

Figure 6A:
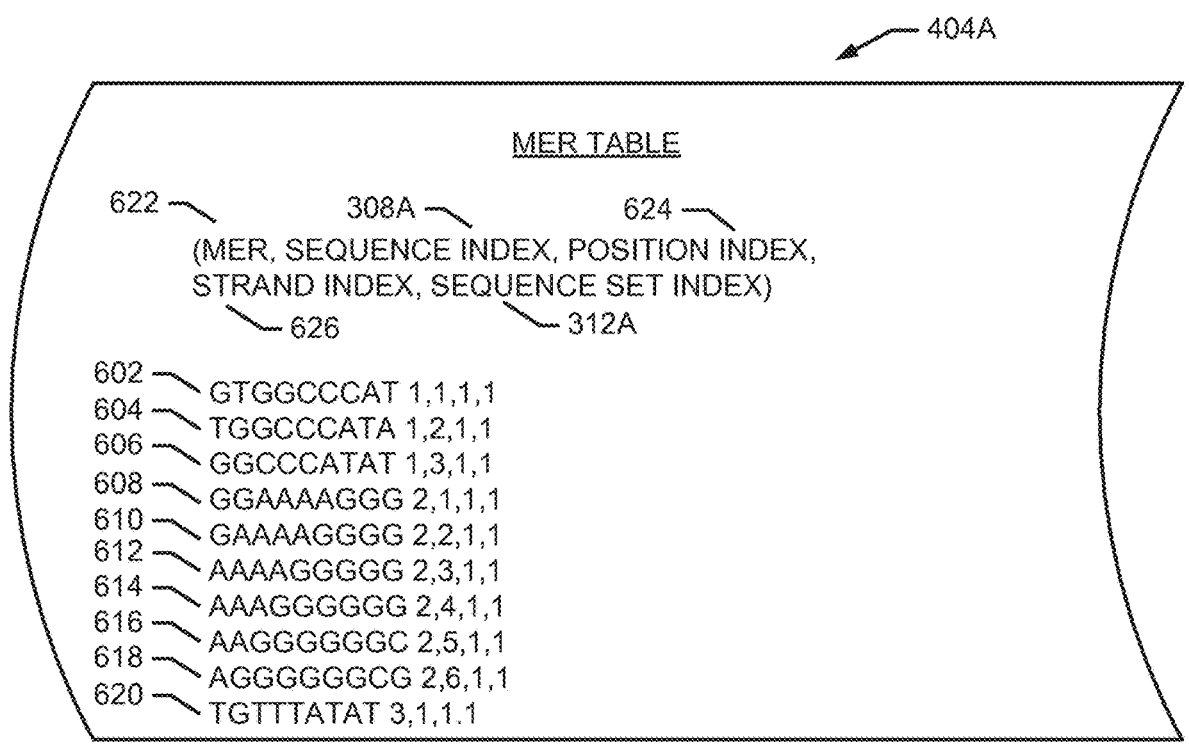
FIG. 6A is a diagram of a mer table in accordance with an embodiment of the present invention.

FIG. 6A depicts an example of a mer table 404A. The mer table 404A contains one or more mer table entries 602-620. Each mer table entry has the mer 622 along with the sequence index 308A, position index 624, strand index 626, and sequence set index 312A that are all assigned to the mer 622. The sequence index 308A is the sequence index of the sequence from which the mer 622 was divided. The position index 624 identifies the location in the originating sequence of a selected nucleotide of the mer, such as a number that stores the location of the mer 622 or a nucleotide of the mer within its originating sequence. In one example, the position index 624 is a number equal to the number of nucleotides from the first nucleotide of the sequence at which the first nucleotide of the mer 622 is located. In other examples, the position index identifies the location in the originating sequence of the center nucleotide of the mer or the last nucleotide of the mer. The strand index 626 is an index that specifies whether the mer 622 is a forward sequence or a reverse complement sequence. In one aspect, the strand index 626 is a number set to 1 for forward sequences and set to 2 for reverse complement sequences. Other numbers, flags, or indicators may be used, such as 0 and 1.

Figure 6B:
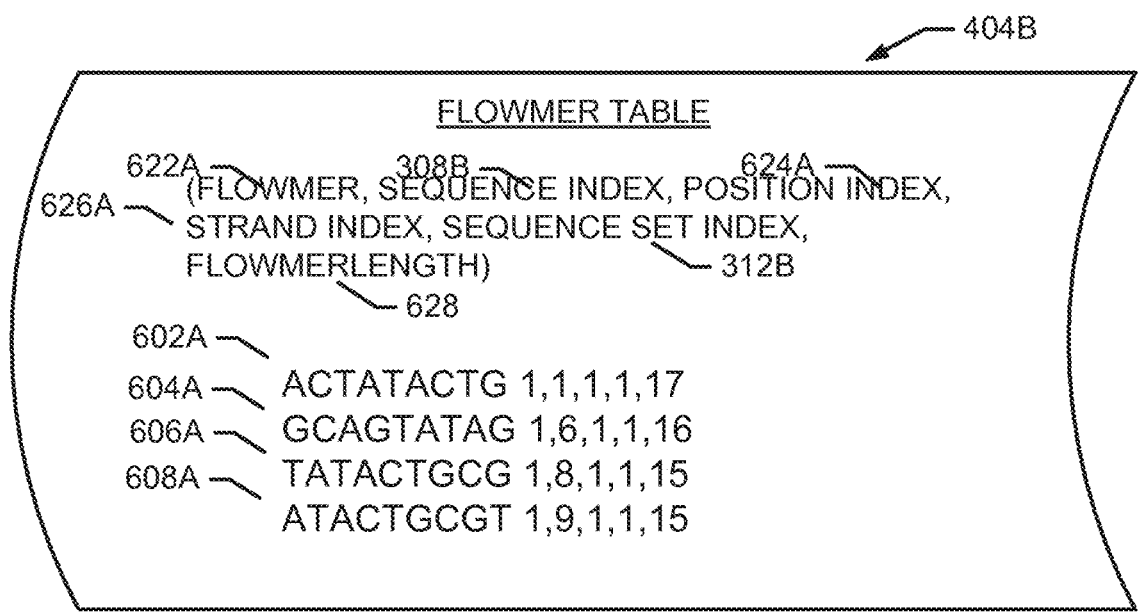
FIG. 6B is a diagram of a flowmer table in accordance with an embodiment of the present invention.

FIG. 6B depicts an example of a flowmer table 404B. The mer table 404B contains one or more flowmer table entries 602A-608B. Each flowmer table entry has the flowmer 622A along with the sequence index 308B, position index 624A, strand index 626A, and sequence set index 312B, and flowmerlength 630 that are all assigned to the flowmer 622A. The sequence index 308B, position index 624A, strand index 626A, and sequence set index 312B are defined previously above. The flowmerlength 628 is number of nucleotides in the subset of the sequence from which the flowmer was generated. However, the flowmerlength 628 may not be equal to the mer length, which is the number of nucleotides in mer, except in the case when no repeating nucleotides were removed in the process of generating flowmer from the sequence.

Other forms and formats of the mer table 404 may be used, and the order of the indices may be changed. Other index types, numbers, or designations may be used.

Mer Generation Example

Figure 7A:
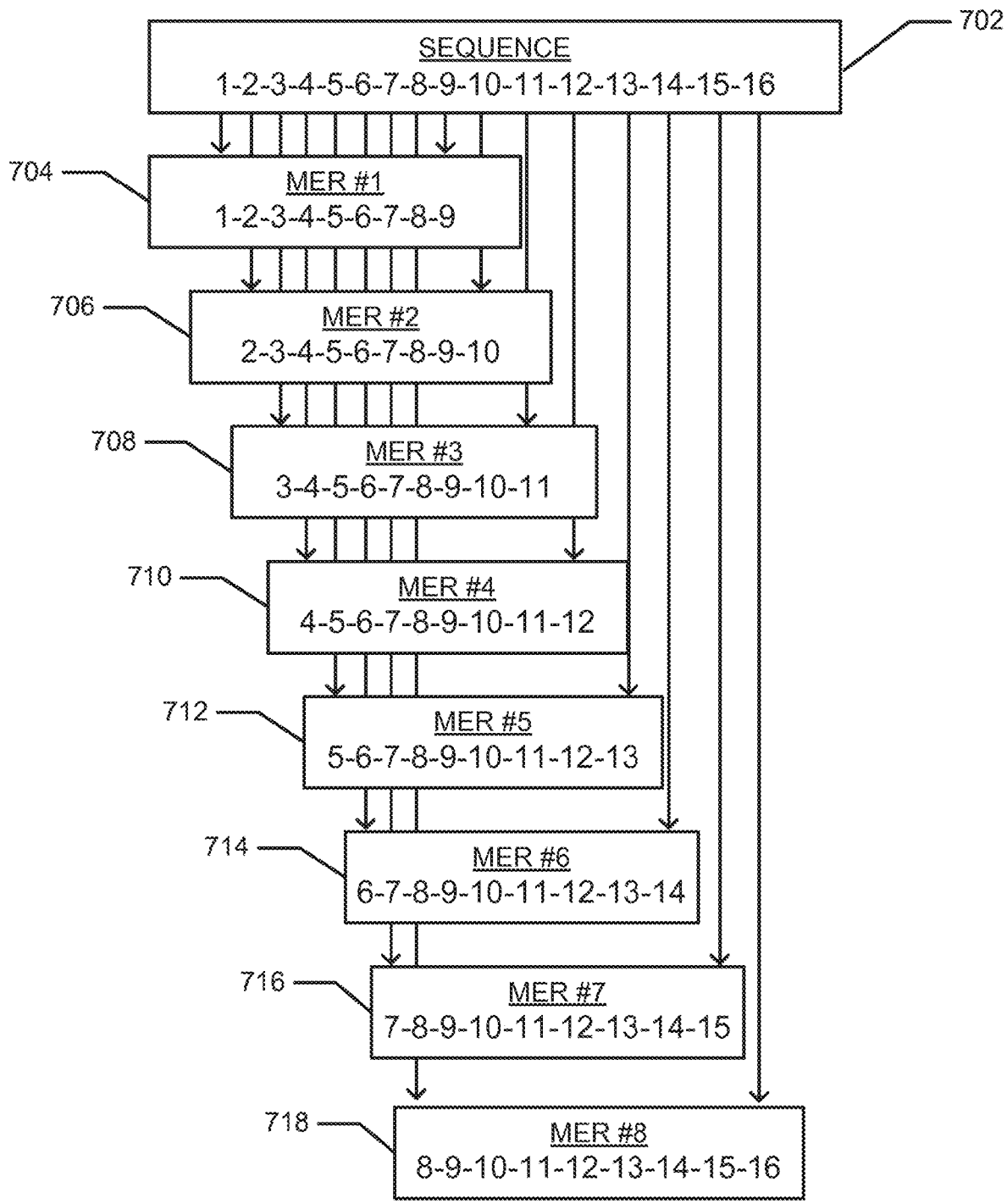
FIG. 7A is a diagram illustrating the division of a sequence into mers in accordance with an embodiment of the present invention.

FIG. 7A illustrates the results of the process used by an exemplary sequence preprocessing system 402 to divide a sequence 702, having 16 nucleotides, into a set of mers 704-718 having mer sequences that are 9 nucleotides long. For illustrative purposes, the nucleotides in FIG. 7A are represented by numbers to facilitate the tracking of the sequences of nucleotides into the resulting mers 704-718. The first mer 704 divided out of the sequence 702 is made up of the first 9 nucleotides of the sequence 702. The second mer 706 is generated by removing the first nucleotide from the first mer 704 and adding the tenth nucleotide of the sequence 702 to the end of the remaining nucleotides of the first mer 704. This process of removing the leading nucleotide and adding the next nucleotide of the sequence 702 to the end of the previous mer is repeated to generate the subsequent mers 708-718. The last mer 718 divided from the read sequence 702 is made up of the final 9 nucleotides in the sequence 702. Once the final nucleotide of the sequence 702 has been added to generate the last mer 718, the process used by the sequence preprocessing system 402 is repeated on any other sequences remaining in the sequence set. Each sequence from each of the sequence sets 202-206 is divided into mers using the same process.

Figure 7B:
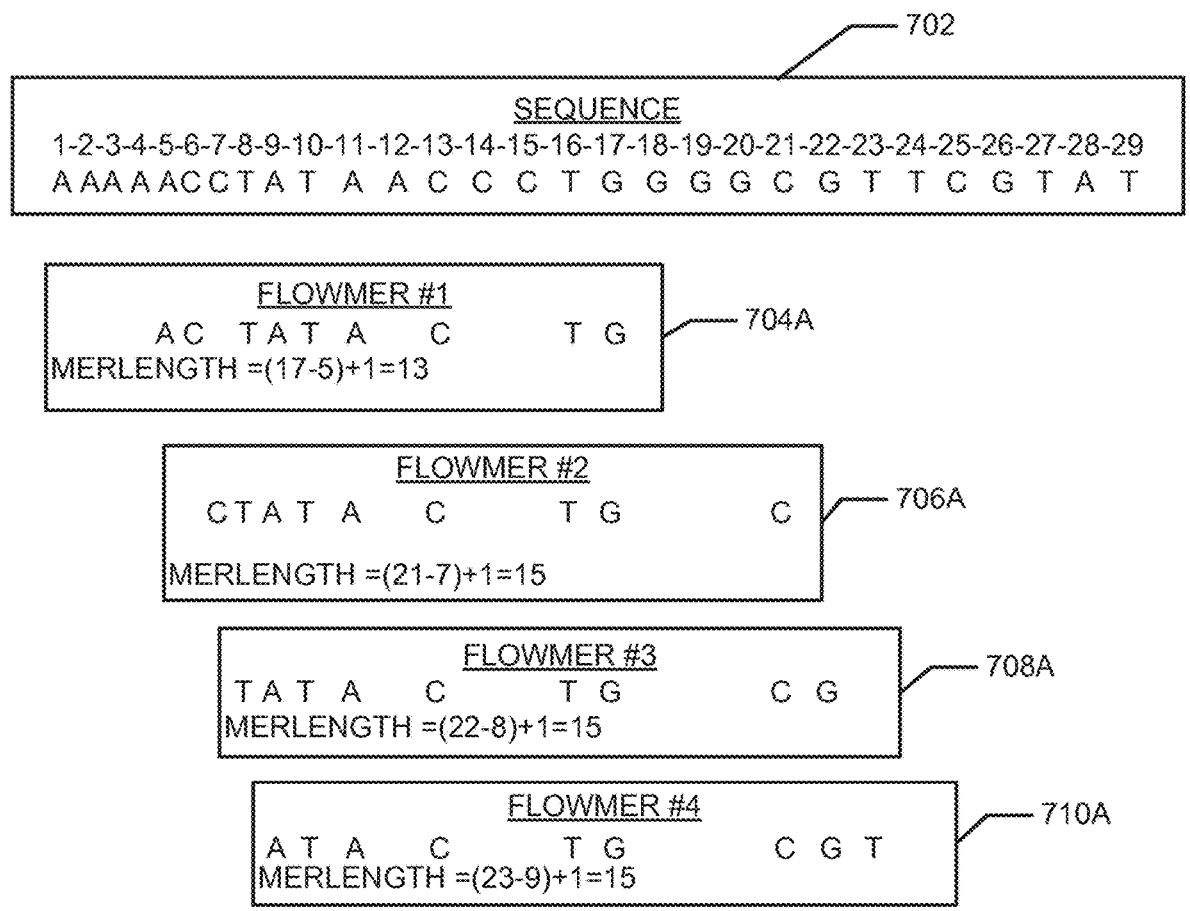
FIG. 7B is a diagram illustrating the division of an exemplary sequence AAAAACCTATAACCCTGGG-GCGTTCGTAT (SEQ ID NO: 3) into flowmers in accordance with an embodiment of the present invention. This exemplary sequence is fictitious and is provided to illustrate the methods of an embodiment of the present invention.

FIG. 7B illustrates the results of the process used by an exemplary sequence preprocessing system 402A to divide a sequence 702A, having 29 nucleotides, into a set of flowmers 704A-710A having flow mer sequences that are 9 nucleotides long. For illustrative purposes, the nucleotides in FIG. 7B are represented by the letters T, A, C, or G, and spaces are included between the consecutive nucleotides within the flowmers 704A-710A to indicate that duplicate nucleotides were removed from the original sequence 702A. the first mer 704A divided out of the sequence 702 includes the last A nucleotide in the initial repeated group from position 5 of the sequence, followed by the first C of the next repeated group from position 6, TATA from positions 8-11, the first C of the repeated group from position 13, T from position 16, and the first G of the repeated group from position 17. In the flowmer 704A, the leading repeated nucleotides at the beginning of the flower 704A and the trailing repeated nucleotides at the end of the flowmer 704A are trimmed from the sequence in the process of generating the flowmer 704A, as illustrated in Figure B.

In an aspect, this convention of trimming any leading and trailing repeated nucleotides during flowmer generation is followed in order to simplify the subsequent processing of the flowmers, in particular, in aligning sequences of opposite direction (one sequence forward-directed and one sequence reverse-directed) based on matching flowmers, as will be discussed further below. In another aspect, the repeating leading nucleotides and repeated trailing nucleotides may be both retained in the process of generating a flowmer from a sequence. For example, if this convention was used for flowmer 704A, the first nucleotide would be the first repeated A from position 1, and the last nucleotide would be the last G of the repeating group from position 20. As a result, the flowmerlength would be 20, rather than 13 as shown in FIG. 7B. Either convention of assigning the positions of any leading and trailing repeated nucleotides may be used, so long as convention is applied consistently for all flowmers generated. Other conventions exist and may be used.

The second flowmer 706A includes all but the first nucleotide of flowmer 704A. In addition, the second flowmer 706A includes a C from position 21. The leading C is from a repeated group. Therefore, the C from position 7 is used in this flowmer. This change in position is because the position of the leading nucleotide is calculated by subtracting 1 from the position of the second nucleotide in the flowmer, as described in step 544 of FIG. 5B. Because the leading C in flowmer 706A is the last in the repeating group, the convention of trimming any leading or trailing repeated groups is maintained.

The third flowmer 708A includes all of the nucleotides of the second flowmer 706A except that the G from position 22 is appended onto the end of the flowmer. The fourth flowmer 710A includes all of the nucleotides of the previous flowmer 708A, with the first T of the repeated group from position 23 appended to the end. This process of removing the leading nucleotide and adding the next nucleotide of the sequence 702A to the end of the previous flowmer is repeated to generate the subsequent flowmers until the final nucleotide in the sequence 702A has been added. Each sequence from each of the sequence sets 202-206 is divided into flowmers going the same process.

AMER/CMER Generation System

The sequences that are analyzed by the layout assembly system 102 may be read sequences resulting from the analysis of a genetic sample by an automated sequencing device. In some cases, such as the sequencing of double-stranded DNA, the read sequences may result from the analysis of either a forward DNA strand or a reverse DNA strand. However, the read sequences do not usually identify the direction of the DNA strand from which it was read. Because a sequence set may be a mixture of forward and reverse sequences, the sequences may be further processed to remove the effect of the direction of the sequences. The amer/cmer generation system 406 reads in the mers from the mer table 404, processes the mers, and generates a strand-independent mer table 408.

The effect of strand direction is removed from each mer by generating a reverse complement sequence for the mer. The reverse complement sequence is formed by assembling all of the complementary nucleotides corresponding to each nucleotide in the mer, and reversing the order of the complementary nucleotides. The mer sequence and the complement sequence are compared, and either the mer or its reverse complement is used to generate the strand-independent mer table entry based on a mer sequence selection rule. In one example of a mer selection rule, the mer or reverse complement that is the lowest alphabetic sequence is used except if the mer is alphabetically equal to its reverse complement (a palindrome), in which case the mer is excluded from the mer table. In another example of a mer selection rule, the mer or reverse complement that is the highest alphabetic sequence is used except if the mer is alphabetically equal to its reverse complement (a palindrome), in which case the mer is excluded from the mer table. In one embodiment, mers of an odd-number sequence length are used to avoid palindromes. Other examples exist. By applying this corrective process, mers resulting from forward sequences and mers resulting from reverse sequences are compared on a consistent basis.

In another aspect, the amer or cmer generation system may also be used to process flowmers in order to generate a table of strand-independent flowmer tables.

Read AMER Generation System

Figure 8:
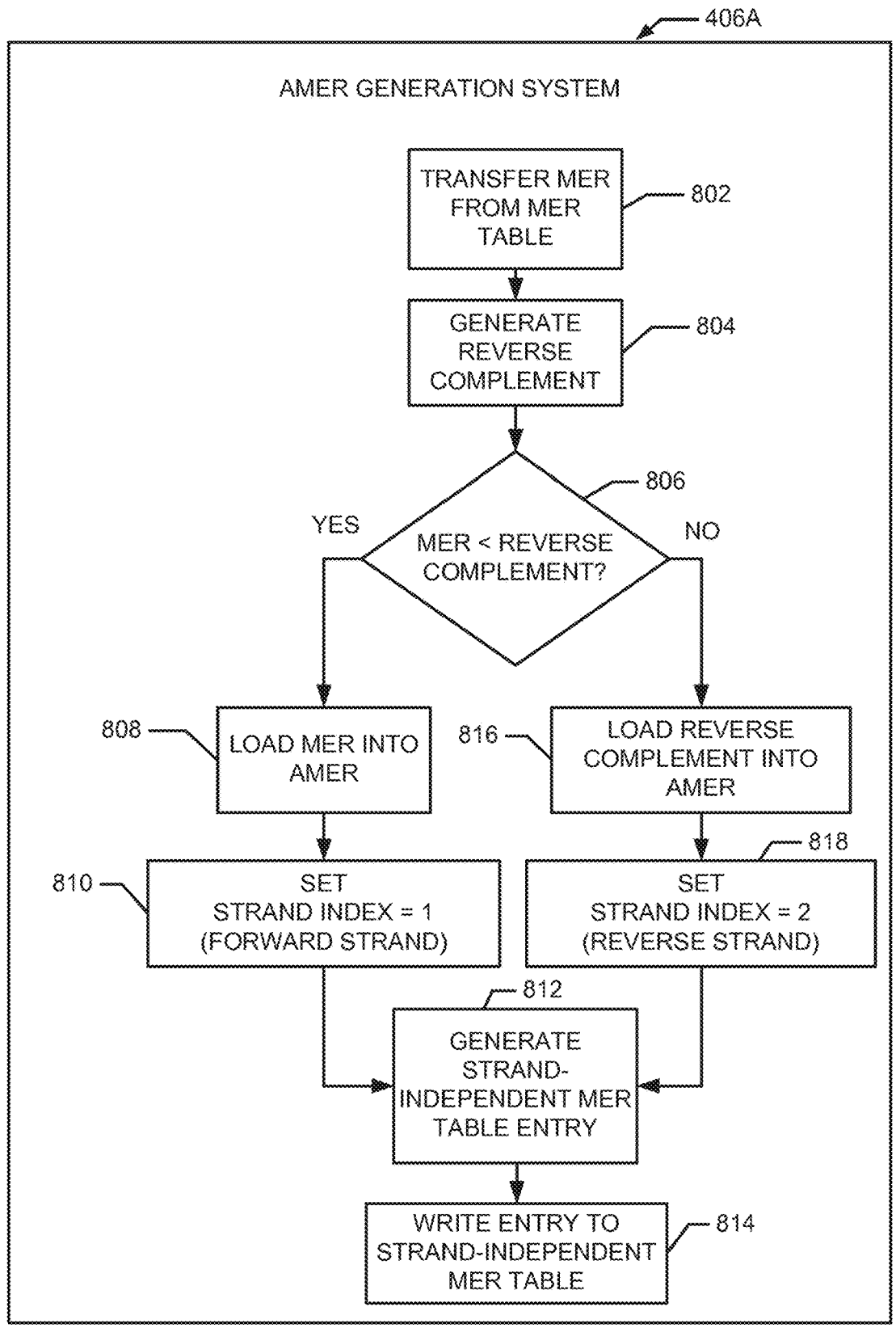
FIG. 8 is a block diagram of an amer generation system in accordance with an embodiment of the present invention.

FIG. 8 is a flow chart showing one example of the process of correcting mers to remove the effect of strand direction from the mers by an exemplary amer generation system 406A. The amer generation system reads in an entry from the mer table 404 at step 802. A reverse complement sequence is generated corresponding to the mer at step 804. The individual nucleotides of the mer sequence and the corresponding reverse complement are compared at step 806. If the mer nucleotides are less than the reverse complement nucleotides, then the mer is loaded into the amer at step 808. A strand index value of 1 is assigned to the amer at step 810 to indicate that the mer is divided from a forward sequence. In this context, a strand index of 1 indicates that the original mer sequence is used in the strand-independent mer table. The amer is then used to generate a strand-independent mer table entry at step 812, which is written to the strand-independent mer table 408 at step 814. If the mer nucleotides are greater than the reverse complement nucleotides, then the reverse complement is written into the amer at step 816. The strand index value of 2 is assigned to the mer at step 818 to indicate the mer is derived from a reverse complement sequence. The amer is then used to generate a strand-independent table entry at step 812, which is written to the strand-independent mer table 408 at step 814.

In an aspect, the comparison of the mer nucleotide may be performed on the basis of the letters ATCG used to represent the nucleotide bases, and the mer is determined to be less than the reverse complement if the mer sequence alphabetically precedes the reverse complement sequence. In another aspect, the reverse complement may be substituted for the mer when the mer is alphabetically after the reverse complement.

In another aspect, the nucleotides may be encoded using numbers, such as the symmetric bit coding, in which A is encoded as 11, G is encoded as 10, C is encoded as 01 and T is encoded as 00. In this aspect, the mer is determined to be less than the reverse complement when the binary representation of the mer is determined to be less than the binary representation of the reverse complement. Other representations of the nucleotide sequences of the mer and its reverse complement may be used, and other rules for comparing the sequences may be used, so long as any rules for comparing the sequences are applied consistently to all nucleotides within all sequence sets processed by the AMER generation system 406A.

Read CMER Generation System

Figure 9:
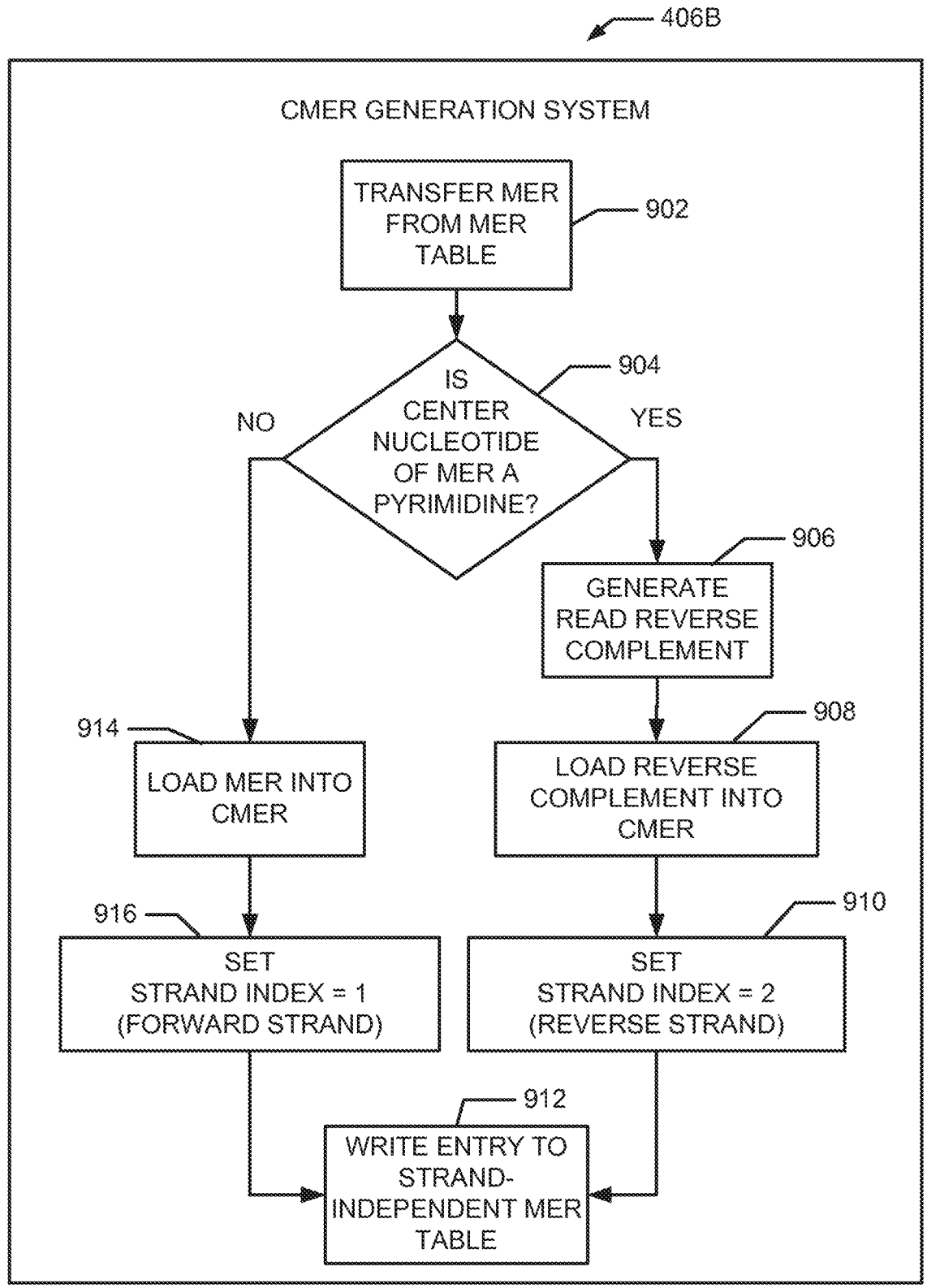
FIG. 9 is a block diagram of a cmer generation system in accordance with an embodiment of the present invention.

FIG. 9 is a flow chart showing another example of the process of correcting the mers to remove the effect of strand direction from the mers by an exemplary cmer generation system 406B. The cmer generation system reads in an entry from the mer table 404 at step 902. The reverse complement is analyzed at step 904 to determine whether the center nucleotide of the mer is a pyrimidine (cytosine, thymine, or uracil). If the center nucleotide is a pyrimidine, then the reverse complement of the mer is generated at step 906 and loaded into the cmer at step 908. The cmer is assigned a strand index of 2 at step 910. If the center nucleotide of the mer is not a pyrimidine, then the mer is loaded into the cmer at step 914, and a strand index value of 1 is assigned to the cmer at step 916. The resulting cmers are used to generate entries that are written to the strand-independent mer table 408 at step 912.

In an aspect, the length of the mer is an odd number, so that the center nucleotide of the mer is a discrete single nucleotide. In another aspect, in the case of a mer with an even number of nucleotides, a pair of central nucleotides immediately adjacent to the center of the nucleotide strand is assessed using a mer loading rule to determine whether to load the mer or the reverse complement of the mer into the cmer register. In one example of a mer loading rule, the pair of central nucleotides is compared to the corresponding reverse complement of the pair of central nucleotides. The mer is loaded into the cmer if the pair of central nucleotides alphabetically follows the corresponding reverse complement of the pair of central nucleotides. For example, the central nucleotides GT alphabetically follow the reverse complement of the central nucleotides AC. The reverse complement is loaded into the cmer if the reverse complement of the central nucleotide pair alphabetically follows the pair of central nucleotides. If the pair of central nucleotides is the same as their reverse complement (a palindrome), then the next pair of nucleotides out from the center of the mer sequence is compared to its corresponding reverse complement. The mer is loaded into the cmer if the next pair of nucleotides is alphabetically higher than the corresponding reverse complement of the next pair of nucleotides. The reverse complement is loaded into the cmer if the reverse complement of the next nucleotide pair alphabetically follows the next nucleotide pair. If the next pair of nucleotides is a palindrome, then each successive pair of nucleotides out from the center of the mer sequence is compared until either the mer or reverse complement is loaded into the cmer, or the entire mer sequence is found to be a palindrome, in which case the mer is eliminated from the mer table. In another embodiment, the mer table entries corresponding to palindrome mers are moved to a palindrome mer table. Other rules may be used.

Amer Generation Example

Figure 10:
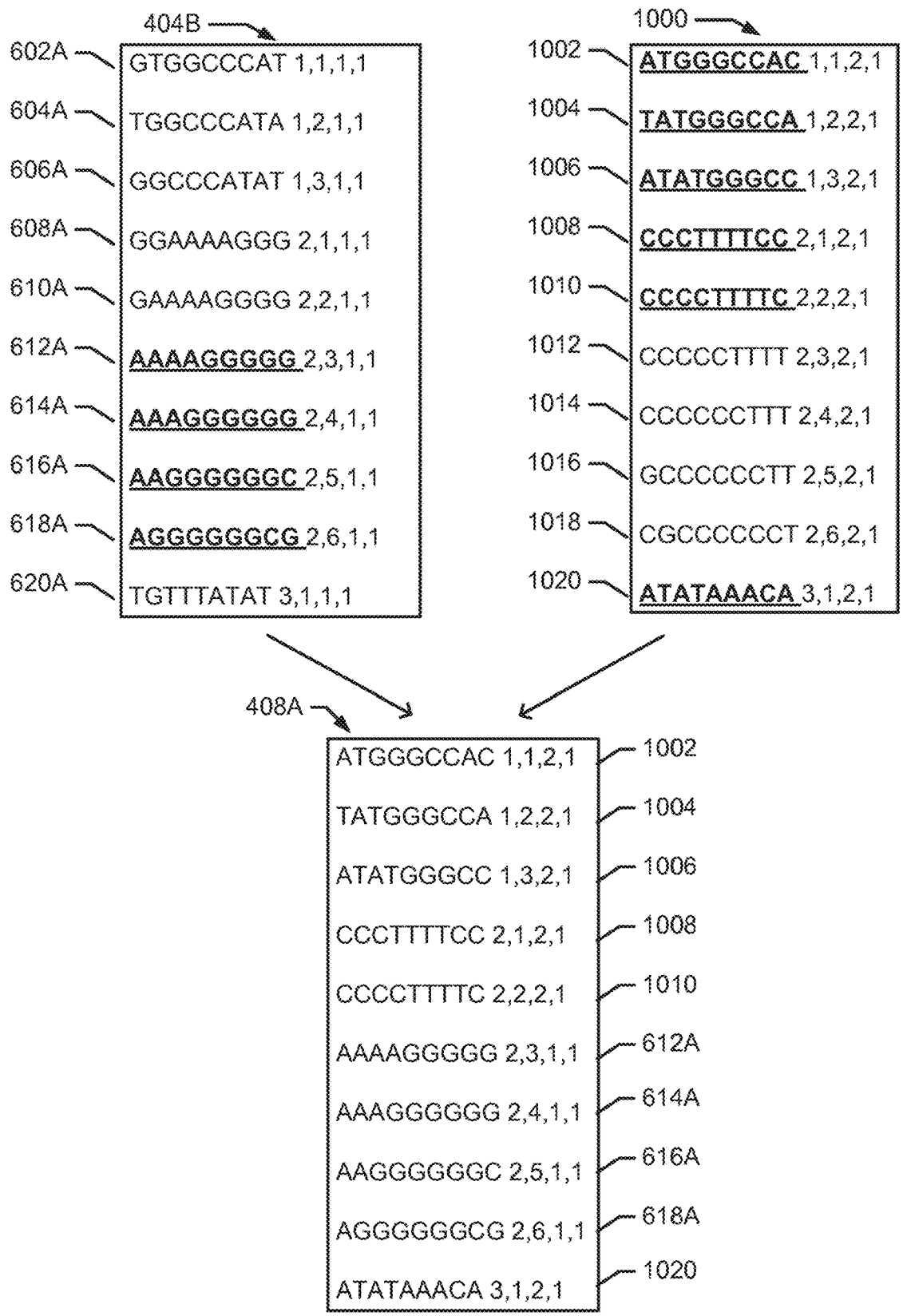
FIG. 10 is an illustration showing the process of removing the effect of strand direction from mers in accordance with an embodiment of the present invention.

FIG. 10 is an illustration of the assessment process used by the amer generation system shown in FIG. 8 to generate a strand-independent mer table 408. The mer table entries 602A-620A are compared to their corresponding reverse complements 1002-1020. For each mer/reverse complement pair, the alphabetically preceding member of the pair is selected for inclusion in the strand-independent mer table 408. The members of each pair that were selected using this rule are indicated in FIG. 10 by underlining and bold face type. The selected entries are written into the strand-independent mer table 408A.

For example, the mer entry 612A (AAAAGGGGG) precedes its reverse complement 1012 (CCCCCTTTT), so mer entry 612A appears as the sixth entry in the strand-independent mer table 408.

Strand-Independent Mer Table

Figure 11:
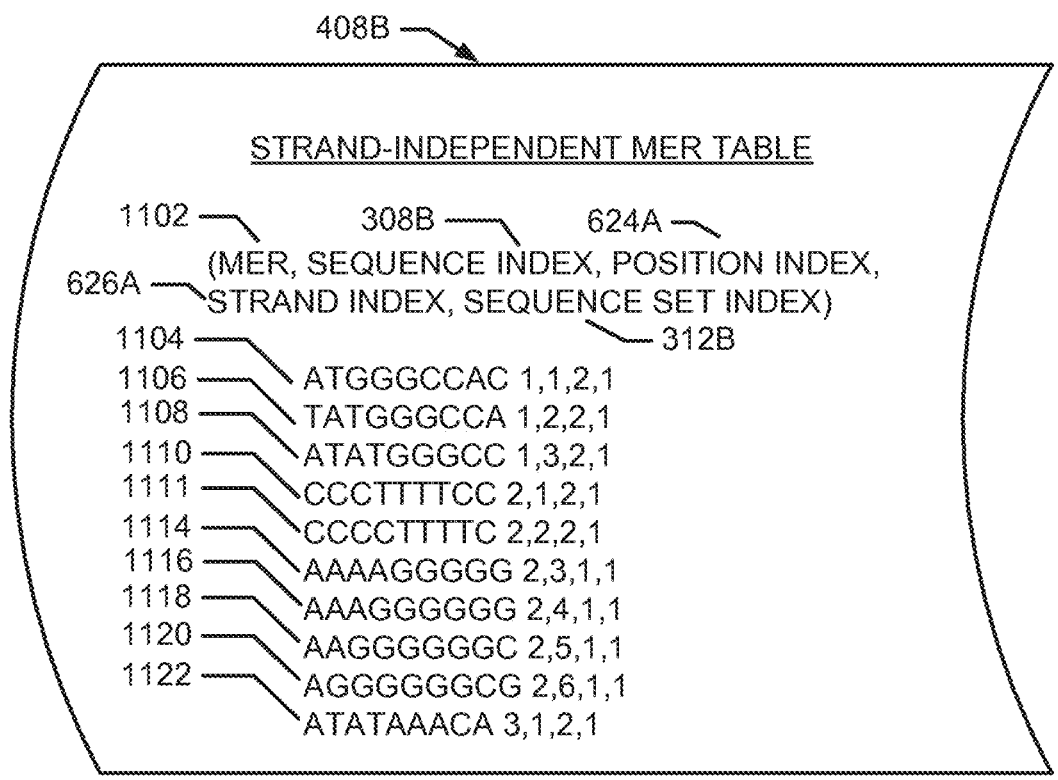
FIG. 11 is a diagram of a strand-independent mer table in accordance with an embodiment of the present invention.

FIG. 11 shows an exemplary strand-independent mer table 408B. Each of the mer table entries 1104-1122 includes a mer 1102 and the sequence index 308B, the position index 624A, and the sequence set index 312B that specify the location of the mer 1102 within the sequence sets 202-206. In addition, the mer table entries include the strand index 626A that indicates whether the mer is a forward sequence or a reverse sequence. The strand-independent table 408B is sorted by the mer sorting system 410 prior to proceeding with a pairwise comparison with a strand-independent mer table derived from another sequence set.

Other forms and formats of the strand-independent mer table 408A may be used, and the order of the indices may be changed. Other index types, numbers, or designations may be used.

Mer Sorting System/Sorted Mer Table

Figure 12:
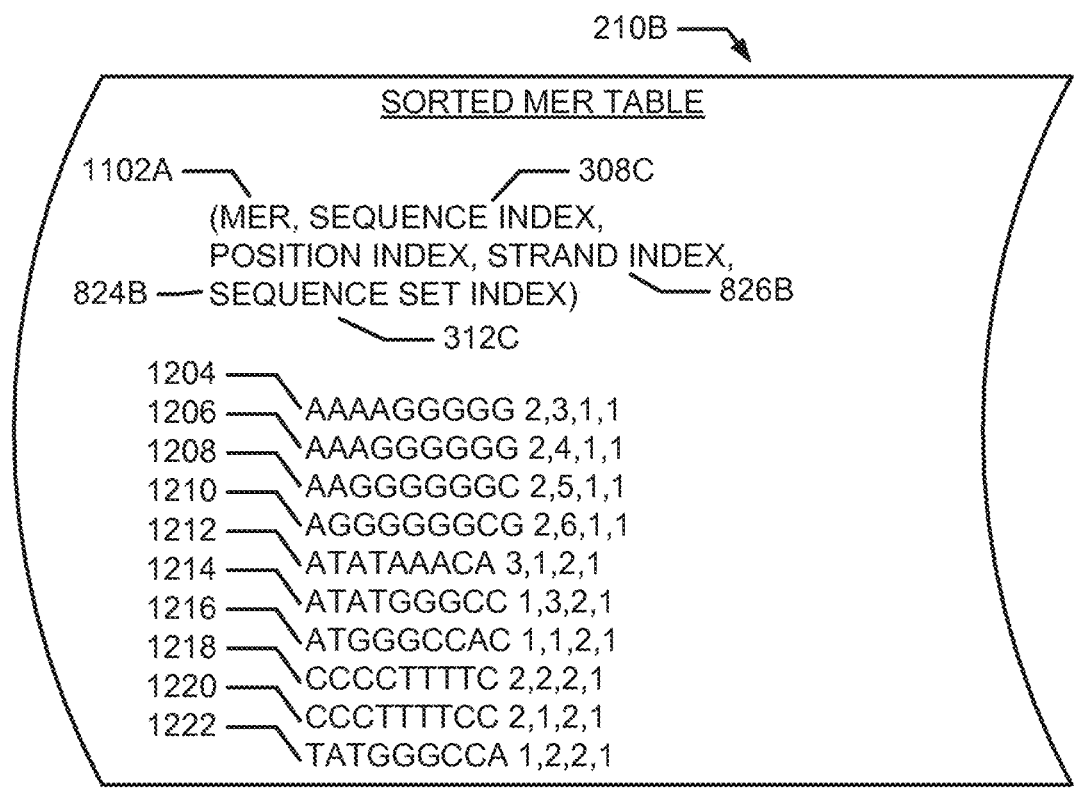
FIG. 12 is a diagram of a sorted mer table in accordance with an embodiment of the present invention.

The mer sorting system 410 sorts the entries of the strand-independent mer table 408B by the nucleotide sequences of the mers and generates a sorted mer table 210. FIG. 12 shows an exemplary sorted mer table 210A. The table entries 1204-1222 result from sorting the mers 1102 from the strand-independent mer table 408B into alphabetical order. Each sorted mer table entry 1204-1222 includes the mer 1102A, the sequence index 408C, the position index 824B, the strand index 826B, and the sequence set index 412C corresponding to the mer table entries 1104-1122 of FIG. 11.

Other forms and formats of the strand-independent mer table 408A may be used, and the order of the indices may be changed. In one example, one strand-independent mer table may include entries for each of the sequence sets 202-206. Other index types, numbers, or designations may be used.

As a result of the sorting, the table entries containing mers 1102A having the same nucleotide sequence are grouped together in each of the sorted mer tables 404. This ordered arrangement of the sorted mer table entries facilitates the subsequent pairwise comparison of table entries of the two or more mer tables 404 by the hit determination system 216.

Hit Determination System

Figure 13:
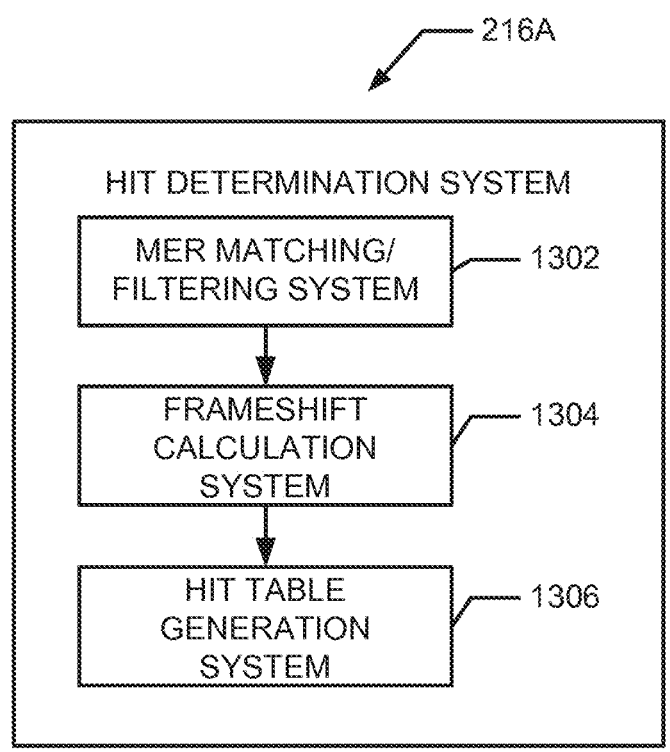
FIG. 13 is a block diagram of a hit determination system in accordance with an embodiment of the present invention.

FIG. 13 is a block diagram of an exemplary hit determination system 216A. In one aspect, the hit determination system 216A includes a mer matching/filtering system 1302, a frameshift calculation system 1304, and a hit table generation system 1306. The mer matching/filtering system 1302 compares each of mers 1102 contained in the entries of one sorted mer table 210A, defined herein as a mer1 (mer1 alternatively is referred to as a read mer), to the each of the mers from another sorted mer table 212A, defined herein as a mer2 (mer2 alternatively is referred to as a comparing mer). The one sorted mer table 210A alternatively may be referred to as the read mer table, and the other sorted mer table 212A may alternatively be referred to as the comparing mer table. In addition, the mer matching/filtering system 1302 may track the number of times a particular mer1/mer2 match occurs and remove any match that occurs at a frequency lower than a SNP threshold or that occurs at a frequency higher than a repeated mer threshold. In one embodiment, the mer matching/filtering system 1302 may compare the entries of a single sorted mer table 210 that includes entries corresponding to each of the sequence sets 202-206. The frameshift calculation system determines the distance in nucleotides that the read sequence containing mer1 must shift along the comparing sequence containing mer2 in order to align the nucleotide sequences of the matched mer1/mer2 pair. The hit table generation system 1306 assembles the location information and frameshift for each of the mer1/mer2 matched pairs, generates a hit table entry, and appends the hit table entry to the hit table.

Mer Matching/Filtering System

Figure 14:
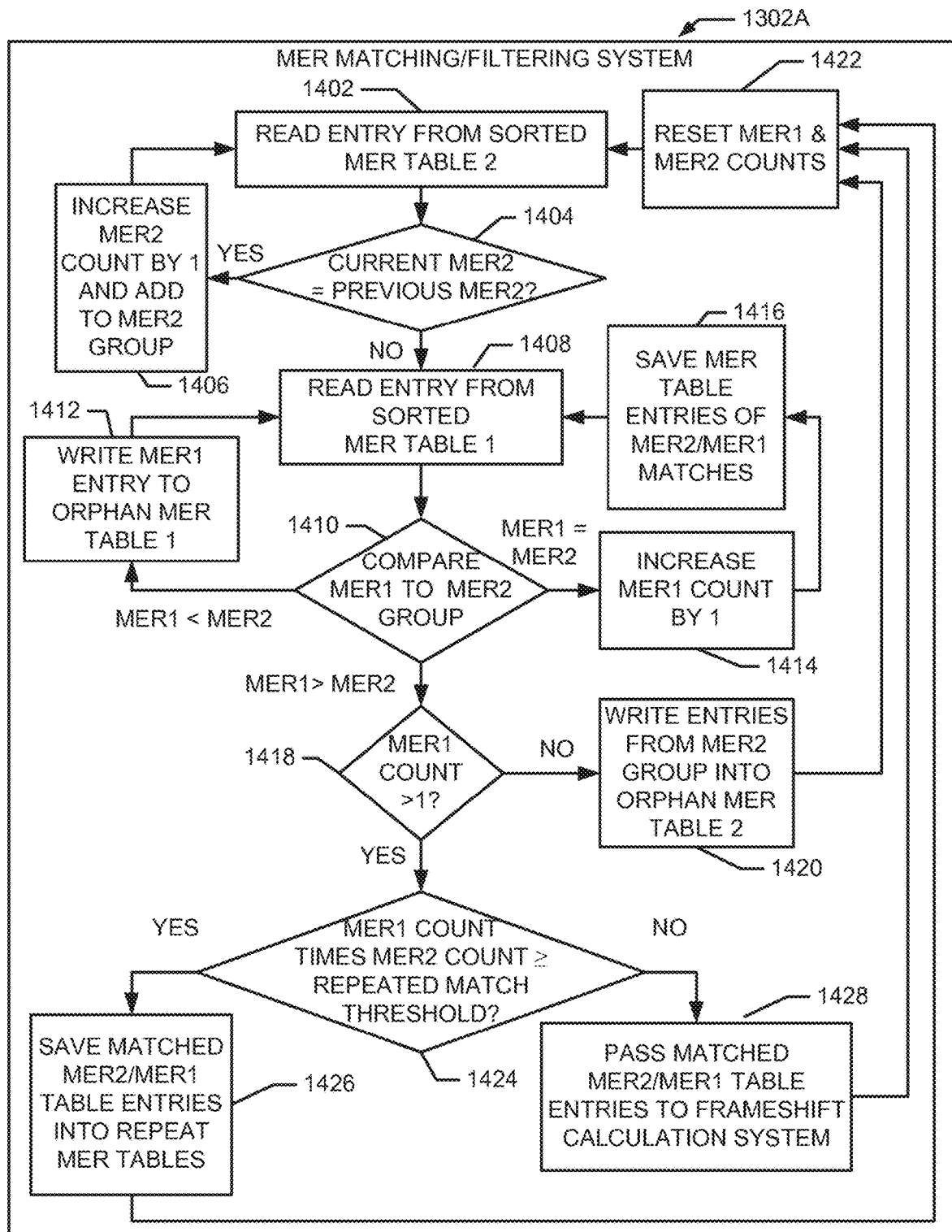
FIG. 14 is a block diagram of a mer matching/filtering system in accordance with an embodiment of the present invention.

FIG. 14 is a flow chart illustrating the processes used by an exemplary mer matching/filtering system 1302A to determine matches between each mer from one sorted mer table 210 and each mer from another sorted mer table 212. The mer matching/filtering system 1302A reads in an entry from the sorted mer table 2 212 at step 1402. The current comparing mer2 is compared to the previous comparing mer2 at step 1404 and included in a group of comparing mer2s at step 1406 if the current mer2 matches the previous mer2. In addition, a mer2 count is increased by 1 for each mer2 added to the group at step 1406 to track the number of mer2s in the current comparison group.

If the current mer2 is different than the previous mer2, a comparison of the group of mer2 nucleotide sequences to each mer1 from sorted mer table 1 210 is performed. At step 1408, a mer1 is read from the sorted mer table 210. Mer2 is compared to mer1 at step 1410.

If the current mer1 is less than the current mer2, then any mer1 that matches the current mer2 is located after the current mer1. In this case, the mer table entry containing the current mer1 is transferred to the orphan mer table 1 220 at step 1412, and the next entry of sorted mer table 1 210 is read.

If the current mer1 matches mer2, a hit table entry is recorded for the matching comparing mer2/read mer1 pair. For example, if there are six mer2's in the current mer2 group that match the current mer1, a total of six hit table entries are recorded corresponding to the matches of the current mer1 to each individual mer2 in the current group. In addition, the number of mer1 nucleotide sequences that produce matches with the mer2 sequences is tracked by incrementing a mer1 count (read mer count) at step 1416 each time a match occurs.

If mer1 is greater than mer2, then any matching mer1 has been identified previously. In this case, the system 1302A checks the mer1 count at step 1418. If the mer1 count is 1 or less, no matches were determined for the current mer2 group, and the mer table entries containing the comparing mer2 sequence in the current comparing mer 2 group are written to the orphan mer table 2 222.

If the mer1 count is greater than one, then at least one match was detected for the current mer2 group. In this case, the total number of matches between the current mer2 group and the mer1's is determined by multiplying the current mer 2 count by the current mer1 count at step 1424. If the product exceeds a repeated match threshold, then the current group of matching mer2 and mer1 table entries saved at step 1416 are transferred to a repeat mer table 2 228 and a repeat mer table 1 226, respectively.

In one aspect, the repeated match threshold is a value equal to the product of the total number of sequences in sequence set 1 times the total number of sequences in sequence set 2 204. In another aspect, the repeated mer threshold may range between about 10 and about 100,000,000 mer sequence comparisons (hits). [Q for inventors: Does the 100,000,000 value make sense? Is there a preferred or default value you are currently using?]] The repeated match threshold is configurable in some aspects.

If the total number of matches in the current group is less than the repeated match threshold for each data set, then the group of mer table entries saved in step 1416 is passed to the frameshift calculation system at step 1428.

In yet another aspect, repeated mers may be identified by counting the number of mers in each of the sorted mer tables 210-212 that have identical mer nucleotide sequences. If the number of repeated mers in a mer table exceeds the repeated mer threshold, then the sorted mer table entries having the repeated mer sequence are transferred to one of the corresponding repeat mer tables 226-230. The counting of mers may be performed by the mer matching/filtering system 1302, the mer sorting system 410, in a separate mer counting system, or in other systems of the layout assembly system 102.

In yet another aspect, one sorted mer table contains entries for each of the sequence sets 202-206. In this aspect, those entries in a group of matching mers having a sequence set index 312 corresponding to one sequence set are added to the mer2 group, and those entries having a sequence index 213 corresponding to another sequence set are compared to the entries in the mer2 group.

The value of the repeated mer threshold may depend on the expected frequency of repeated nucleotide sequences in the sequence sets and the length of the mers. In another aspect, the layout assembly system 702 uses a larger repeated mer threshold for a sequence set in which the expected frequency of repeated nucleotide sequences is high, and a smaller repeated mer threshold when the expected frequency is low. In another aspect, the repeated mer threshold ranges between about 2 mer repeats and about 1000 mer repeats. In yet another aspect, the repeated mer threshold is about 20 mer repeats.

Example of Mer Matching

Figure 15:
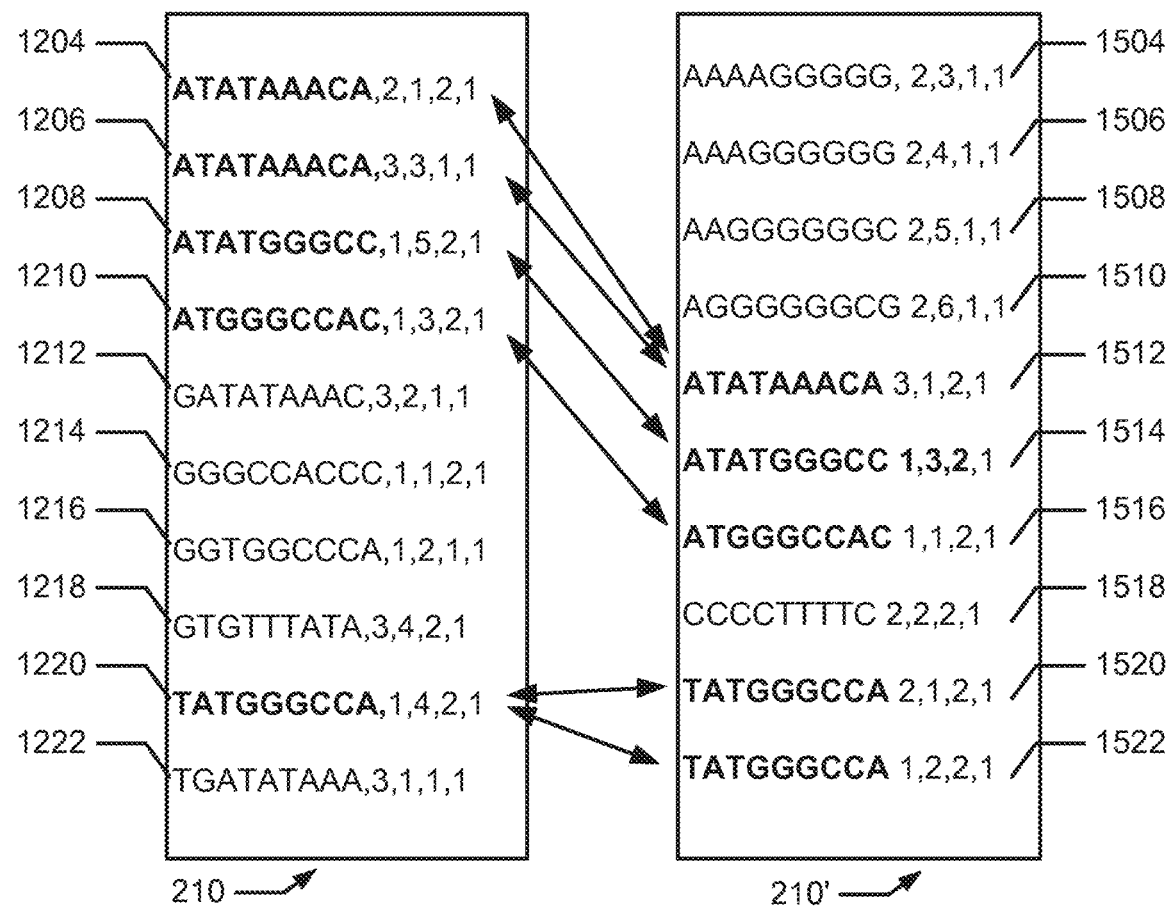
FIG. 15 is an illustration showing the process of determining matches between mers in accordance with an embodiment of the present invention.

FIG. 15 is an illustration of the comparison process used by the mer matching/filtering system 1302. The sorted mer table entries 1204-1222 of a first sorted mer table 210 are compared to the sorted mer table entries 1504-1522 of a second sorted mer table 210'. Because the sorted mer table entries 1504-1510 and 1518 of the second mer table 210' do not have any matches among the sorted mer table entries 1204-1222 of the first mer table 210, these entries are written to an orphan mer table 222 corresponding to the second mer table 210'. Similarly, the sorted mer table entries 1212-1218 and 1222 of the first sorted mer table 210 do not match any of the sorted mer table entries 1504-1522 of the second sorted mer table 210' and are transferred to an orphan mer table 220.

The sorted mer table entry 1512 of the second sorted mer table 210' matches the sorted mer table entries 1204 and 1206 of the first sorted mer table 210'. So, two hit table entries are generated by the mer matching/filtering system 1302. Two hit table entries are also generated for the matched sorted mer table entries 1208/1514 and 1210/1516. Because entry 1220 matches entry 1520 and entry 1522, two additional hit table entries are generated by the mer matching/filtering system 1302. Once all of the matches have been determined by the mer matching/filtering system 1302, the hit table entries are passed to the frameshift calculation system 1304.

Frameshift Calculation System

Figure 16A:
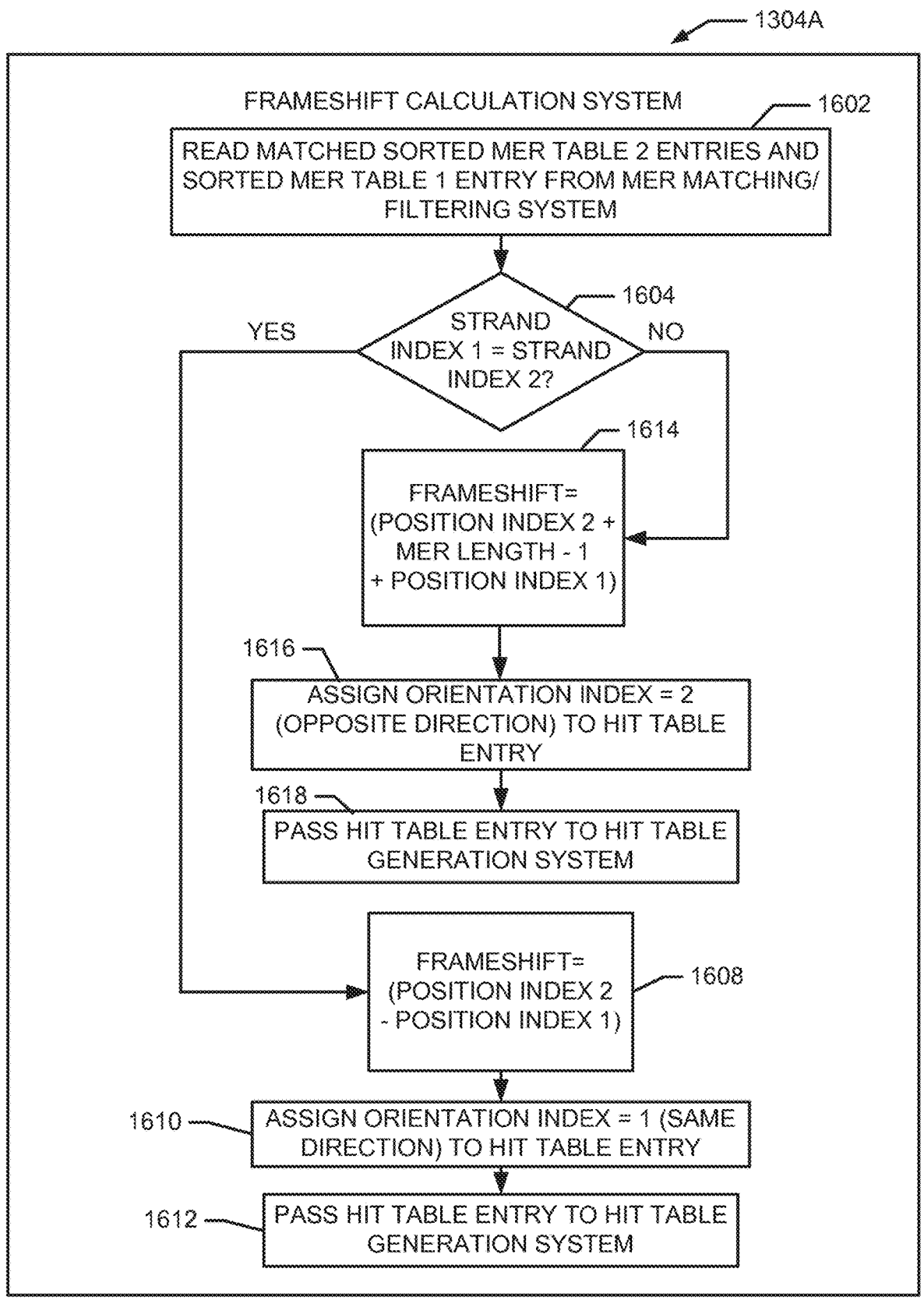
FIG. 16A is a block diagram of a frameshift calculation system in accordance with an embodiment of the present invention.
Figure 16B:
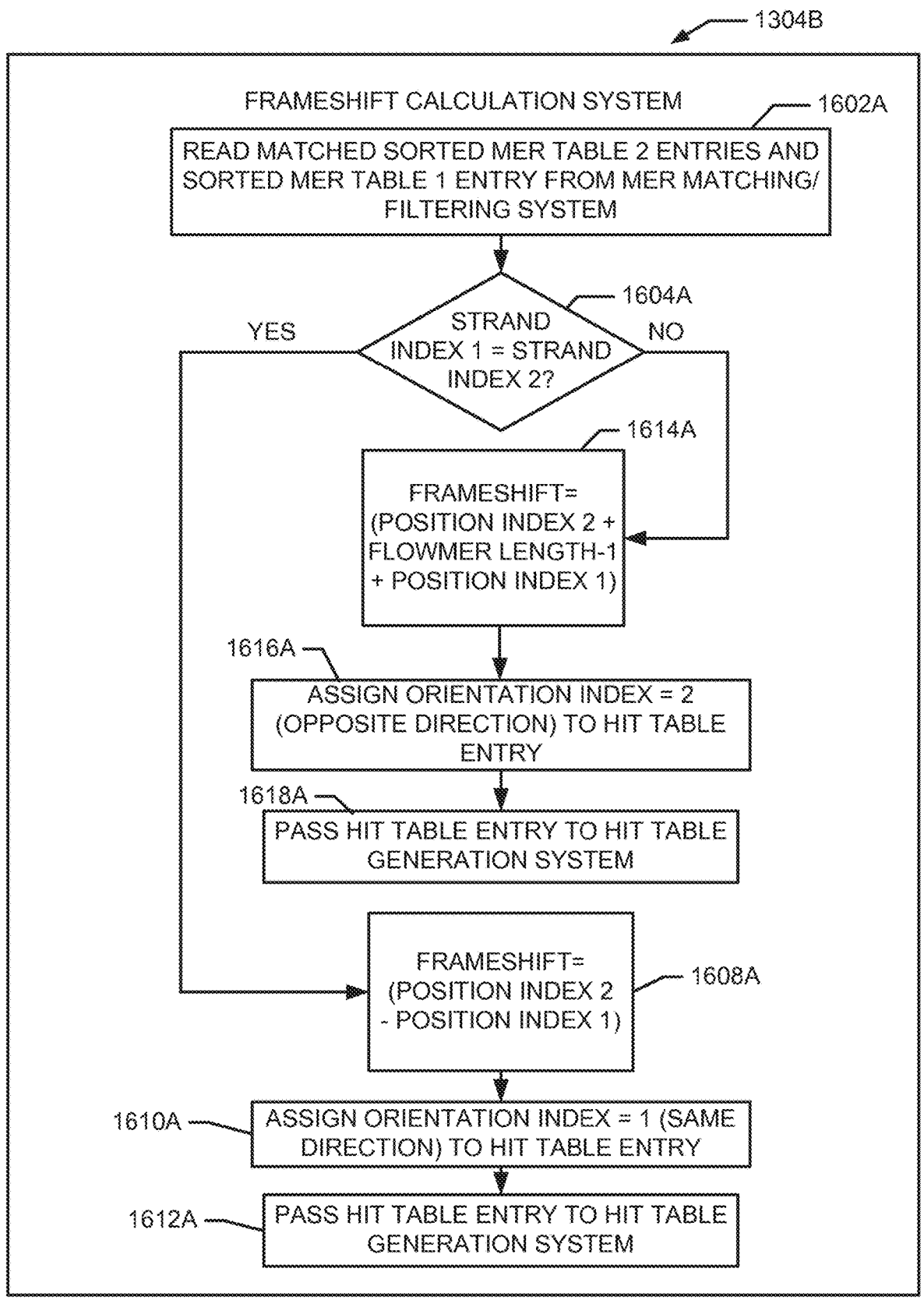
FIG. 16B is a block diagram of a frameshift calculation system in accordance with another embodiment of the present invention.

FIG. 16 is a flowchart illustrating the processes used by an exemplary frameshift calculation system 1304A to calculate a frameshift of each match identified by the mer matching/filtering system 1302. The frameshift is a number assigned to each entry in the hit table that specifies the number of nucleotides that the originating sequence of mer1 must be shifted down the originating sequence of mer2 to align mer1 with mer2. The frameshift is the position of the first base of one sequence projected on the first base of the other sequence when matched at the mer. Alternatively, other selected comparing bases may be used such as the last base in the sequences. At step 1602, the mer table entries for each mer1 and mer 2 corresponding to a group of matches are read by the frameshift calculation system 1304A.

For each of the matches, the strand index 1, alternately referred to as the read strand index, from the mer1 table entry is compared to the strand index 2, alternatively referred to as the comparing strand index, from the mer2 table entry at step 1604.

If the strand indices have the same value, then mer2 and mer1 are oriented in the same direction. In this case, the frameshift is determined by calculating the difference between position index 2 and position index 1 at step 1608. In one example, position index 1 may be a read mer position index, and position index 2 may be a comparing mer position index. An orientation index of 1 is assigned to a hit table entry corresponding to the match to specify that mer2 and mer1 in the match were aligned in the same direction at step 1610. The hit table entry is passed to the hit table generation system 1306A at step 1612.

If strand index 1 is not equal to strand index 2, then mer2 and mer1 are oriented in opposite directions. In this case, the frameshift is determined by obtaining the sum of position index 2, position index 1, and the mer length at step 1614. An orientation index value of 2 is assigned to the mer2/mer1 pair to specify that the mer sequences are oppositely directed at step 1616, and a hit table entry is passed to the hit table generation system at step 1618.

Hit Table Generation System

Figure 17:
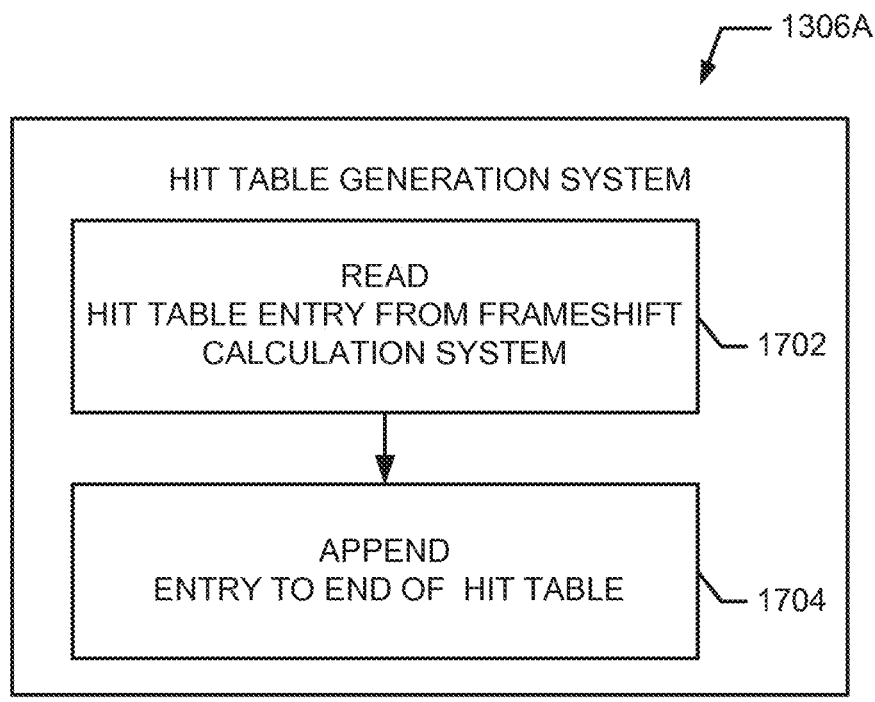
FIG. 17 is a block diagram of a hit table generation system in accordance with an embodiment of the present invention.

FIG. 17 is a flow chart illustrating the processes used by an exemplary hit table generation system 1306A to assemble the hit table entries into a hit table 502. The hit table generation system 1306A reads each hit table entry generated by the frameshift calculation system 1304 at step 1702 and writes the hit table entry to the end of the hit table at step 1704.

Hit Table

Figure 18:
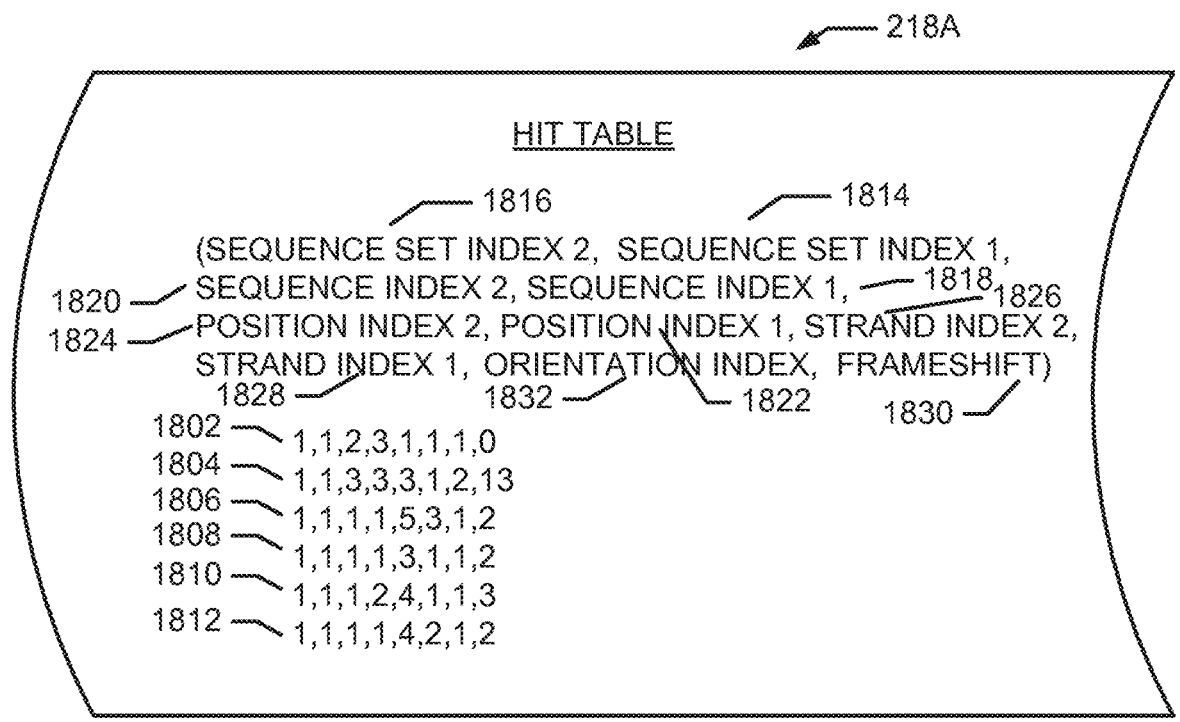
FIG. 18 is a diagram of a hit table in accordance with an embodiment of the present invention.

The hit table 218 is a summary of all matches between the mers from sorted mer table 1 210 and the mers from sorted mer table 2 212. An exemplary hit table is shown in FIG. 18. The hit table contains a list of hit table entries 1802-1812. Each hit table entry contains one or more indices that specify the location of mer2 and mer1 in their respective originating sequence sets, the direction of the mers, the orientation of the mers relative to each other, and the frameshift of the match. Sequence set index 1 1814 and sequence set index 2 1816 specify the originating sequence sets of mer1 and mer 2 respectively. Sequence index 1 1818 and sequence index 2 1820 specify the sequences within the sequence sets that contain mer1 and mer 2 respectively. Position index 1 1822 and position index 2 1824 specify the locations of mer1 and mer2 on their respective sequences. Strand index 1 1828 and strand index 2 1830 specify whether the mers are forward or reverse in direction, and the orientation index 1832 specifies whether the mers are oriented in the same direction or different directions. All or a portion of the hit table entries 1802-1812 may be alphanumeric data, integers, hexadecimal numbers, binary numbers, or another data encoding convention. Other examples exist.

Hit Table Sorting System

Figure 19:
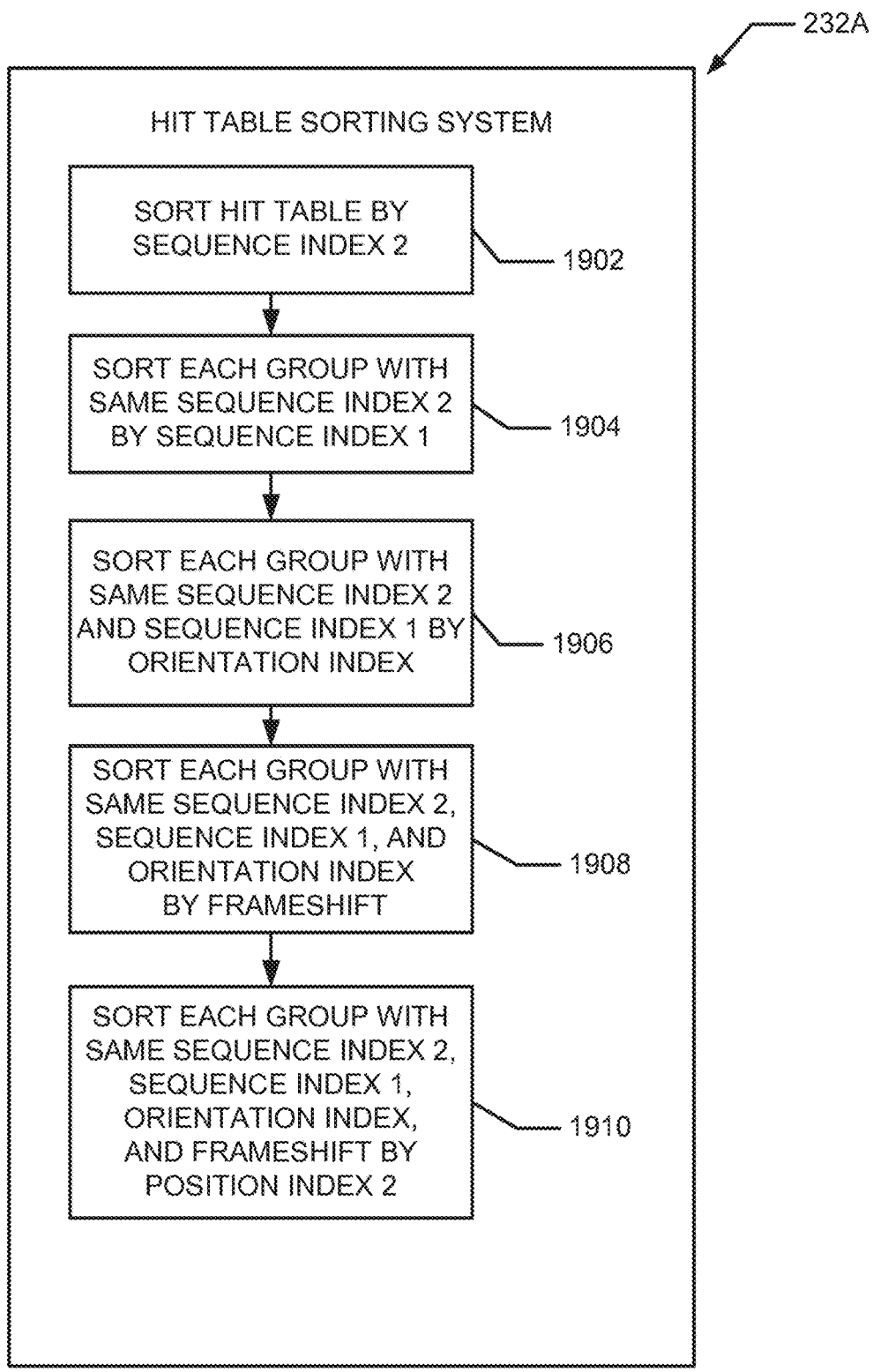
FIG. 19 is a block diagram of a hit table sorting system in accordance with an embodiment of the present invention.

FIG. 19 is a flowchart illustrating the processes used by an exemplary hit table sorting system 232A to sort the hit table 218 generated by the hit determination system 216. In one aspect, the hit table sorting system 232A rearranges the entries of the hit table 218 to order the entries by sequence index 2, sequence index 1, orientation index, frameshift, and position index 2.

The entries of the hit table 218 are sorted by sequence index 2 at step 1902, which arranges the hit table entries into groups (sequence index 2 groups) having the same sequence index 2. Within each sequence index 2 group, the hit table entries are further sorted by sequence index 1 at step 1904, forming groups of hit tables having same sequence index 1 (sequence index 1 group). Within each sequence 1 group, the hit table entries are further sorted by orientation index at step 1906, forming groups of hit table entries (orientation index groups) having the same orientation index value. Within each orientation index group, the hit table entries are further sorted by frameshift at step 1908, forming groups of hit table entries (frameshift groups) having the same frameshift value. Within each frameshift group, the hit table entries are further sorted by position index 2 at step 1910, forming groups of hit table entries (position index groups) having the same value of position index.

The resulting sorted hit table 234 contains a series of hit table entries that are arranged into smaller groups containing the hit table entries corresponding to all matches between mers derived from one sequence of sequence set 2, and mers derived from one or more sequences of sequence set 1. Within each of these groups, the entries corresponding to matches between mers derived from one sequence 2, such as one comparison sequence, and one sequence 1, such as one read sequence, are grouped together. Within each group of entries corresponding to matches between one sequence 2, such as the comparing sequence, and one sequence 1, such as the read sequence, the entries are further arranged into groups of matches between mers oriented in the same direction and mers with opposite orientation. The sorted hit table 234A is passed to the hit table condensing system 240.

Different sorting algorithms may be used to implement the sorting functions of the hit table sorting system 232A. Examples of sorting algorithms include bubble sort, cocktail sort, comb sort, gnome sort, selection sort, insertion sort, shell sort, binary tree sort, library sort, merge sort, in-place merge sort, heapsort, smoothsort, quicksort, introsort, patience sorting, strand sort, pigeonhole sort, bucket sort, counting sort, LSD Radix sort, MSD Radix sort, and spreadsort. Other examples exist.

Sorted Hit Table

Figure 20:
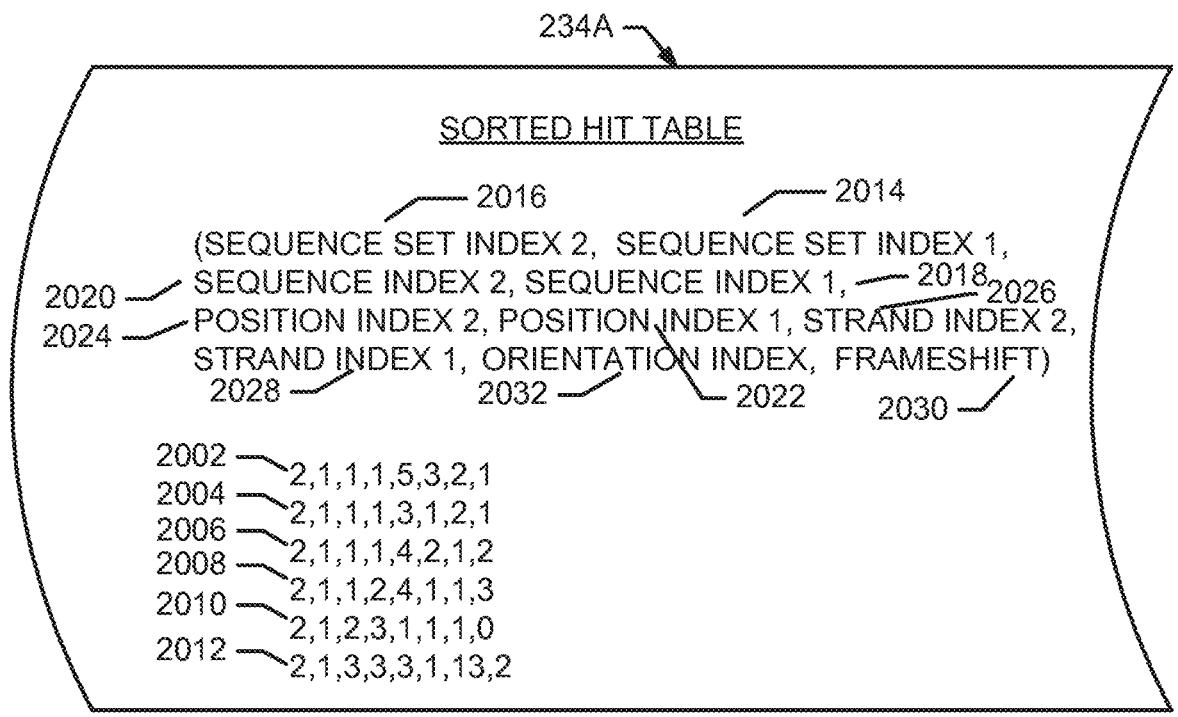
FIG. 20 is a diagram of a sorted hit table in accordance with an embodiment of the present invention.

An exemplary sorted hit table 234A is shown in FIG. 20. The hit table contains a list of hit table entries 2002-2012. Each hit table entry 2002-2012 contains one or more indices that specify the location of mer2 and mer1 in their respective originating sequence sets, the direction of each matched mer in the orientation of the mers relative to each other, and the frameshift of the match. Sequence set index 1 2014 and sequence set index 2 2016 specify the originating sequence sets of mer1 and mer 2 respectively. Sequence index 1 2018 and sequence index 2 2020 specify the originating sequences within the sequence sets for mer1 and mer 2 respectively. Position index 1 2022 and position index 2 2024 specify the locations of mer1 and mer2 on their respective originating sequences. Strand index 1 2028 and strand index 2 2030 specify whether the mers are forward or reverse in direction, and the orientation index 2032 specifies whether the mers are oriented in the same direction or different directions. The frameshift specifies the number of nucleotides that the originating sequence of mer1 must be shifted down the originating sequence of mer2 to align mer1 with mer2. All or a portion of the hit table entries 2002-2012 may be alphanumeric data, integers, hexadecimal numbers, binary numbers, or another data encoding convention. The sorted hit table 234A is passed to the hit table condensing system 236 for further processing.

Hit Table Condensing System

The hit table condensing system 236 processes the sorted hit table 234 to identify and combine any multiple hits between each sequence of sequence set 1 202 (read sequence) and each sequence of sequence set 2 204 (comparing sequence). For each hit identified as having duplicates, the number of duplicates is recorded as a score, defined in this context as the number of duplicate hits. The score is an approximation of the number of bases from a given sequence from sequence set 1 202 that forms a hit at a particular location in sequence set 2.

Figure 21:
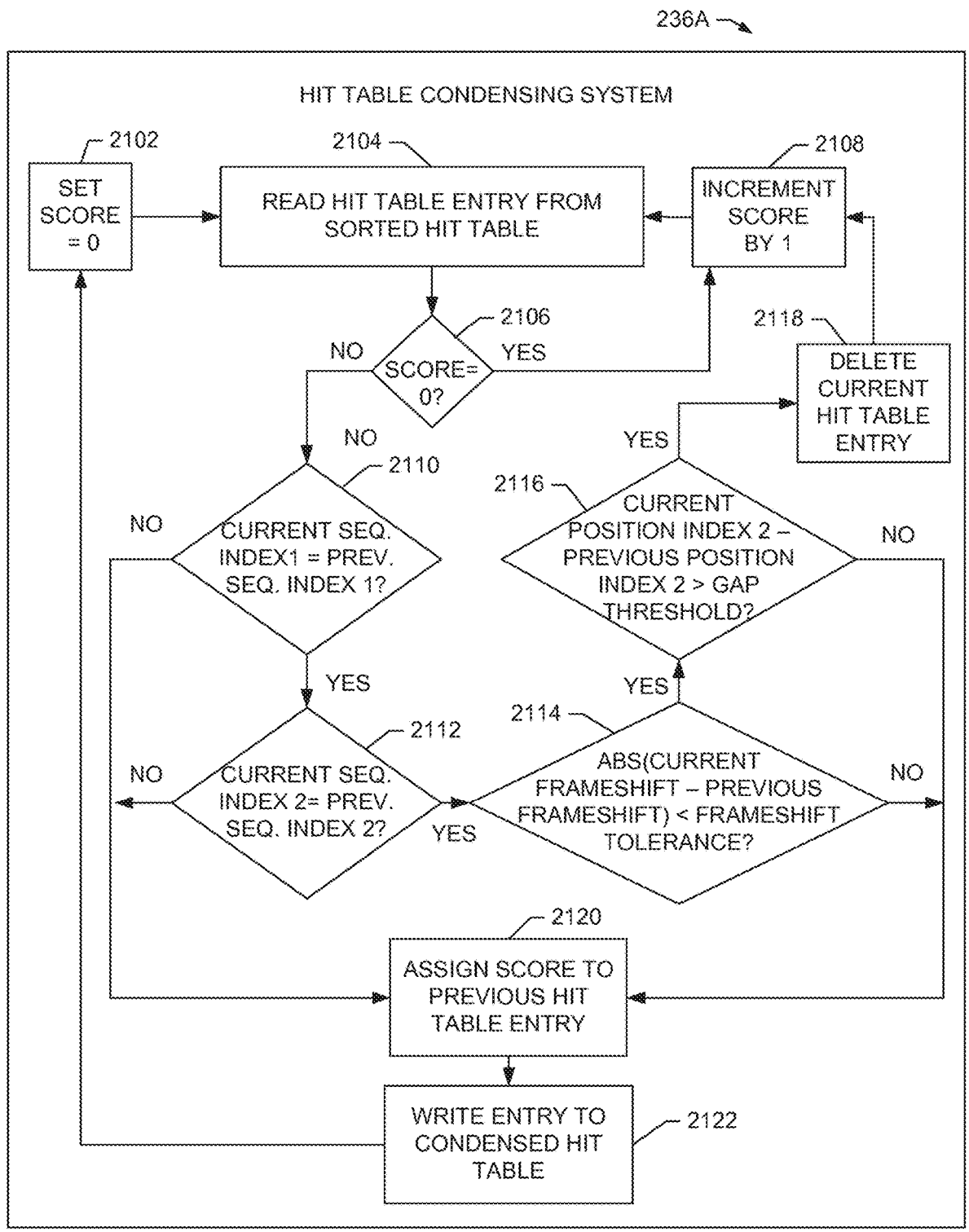
FIG. 21 is a block diagram of a hit table condensing system in accordance with an embodiment of the present invention.

FIG. 21 is a flow chart illustrating the processes used by an exemplary hit table condensing system 236A to determine a score for the number of duplicate hit table entries in the sorted hit table 234 and to generate a condensed hit table 238. Initially, the hit table condensing system 236A initializes the score to a value of zero at step 2102 and then reads a first current hit table entry from a sorted hit table 234 at step 2104. A score of zero is assigned to specify the start of a new set of matched hit table entries. The value of the score is checked at step 2106. If the current value of the score is equal to zero, then the score is increased by 1 at step 2108, and another hit table entry is read from the sorted hit table 234 at step 2104.

If the score is not equal to zero at step 2106, various indices from the current sorted hit table entry are compared to the corresponding indices from the previous sorted hit table entry. The current sequence index 1 2014 is compared to the previous sequence index 1 at step 2110. If the sequence index 1 values match, the current sequence index 2 2016 is compared to the previous sequence index 2 at step 2112. If the sequence index 2 values match, the current frameshift 2030 and the previous frameshift are compared at step 2114.

In step 2114, the absolute value of the difference between the current frameshift and the previous frameshift are compared to a frameshift tolerance. The frameshift tolerance, in this context, is the acceptable variation of frameshift due to error sources, such as SNPs or sequencing errors. In one aspect, the frameshift tolerance, expressed as a number of nucleotide bases, may be any value from zero up to about 10 nucleotides. If the incremental change between the current frameshift and the previous frameshift falls within the frameshift tolerance at step 2114, the position index 1 2022 is evaluated at step 2116.

As described previously, position index 2 2024 specifies the position of the first nucleotide of the sequence used to generate a mer2 relative to the first nucleotide of a comparing sequence from sequence set 2 204 when the mer2 is aligned with the mer1. If the current and previous mer2s are located too far apart on the sequence from sequence set 1 2014, a gap may exist between the two mers that may confound the layout assembly process. If the incremental difference between the current and previous position index 2 falls within a gap threshold, then the current hit table entry is added to the current condensed hit table entry group by deleting the current hit table entry at step 2118 and increasing the score for the current hit table entry by 1 at step 2108. A new comparison is then started by reading a new current hit table entry at step 2104.

In an aspect, the gap threshold may vary from 0 to about 10% of the length of the sequence from sequence set 2. In another aspect, the gap threshold may vary from 0 to about 1000 nucleotides. In an exemplary aspect, the gap threshold may be 10 nucleotides.

If the current hit table entry does not match the previous hit table at any one of steps 2110, 2112, 2114, or 2116, the current hit table entry is set as the first hit table entry of a new group. The current score is assigned to the previous sorted hit table entry at step 2120, and an entry is written to the condensed hit table that includes the previous sorted hit table entry as well as the score at step 2122. After resetting the score to a value of 0 at step 2102, the next hit table entry is read from the sorted hit table 234 at step 2104.

In one aspect, the resulting condensed hit table 238 contains at least one condensed hit table entry that includes all of the indices of the sorted hit table entry, plus a score that specifies how many times the hit table entry was repeated in the sorted hit table 234A. The number of repeats of a hit table entry may be used as an indication of the strength or confidence in the nucleotide match specified in the hit table entry. In another aspect, each condensed hit table entry may contain other descriptive statistics such as a coverage score, defined as the total number of nucleotides from sequence set 1 that were matched to generate the condensed hit table entry. The condensed hit table 238A is passed to the post processing system 240 for further processing and analysis.

Condensed Hit Table

Figure 22:
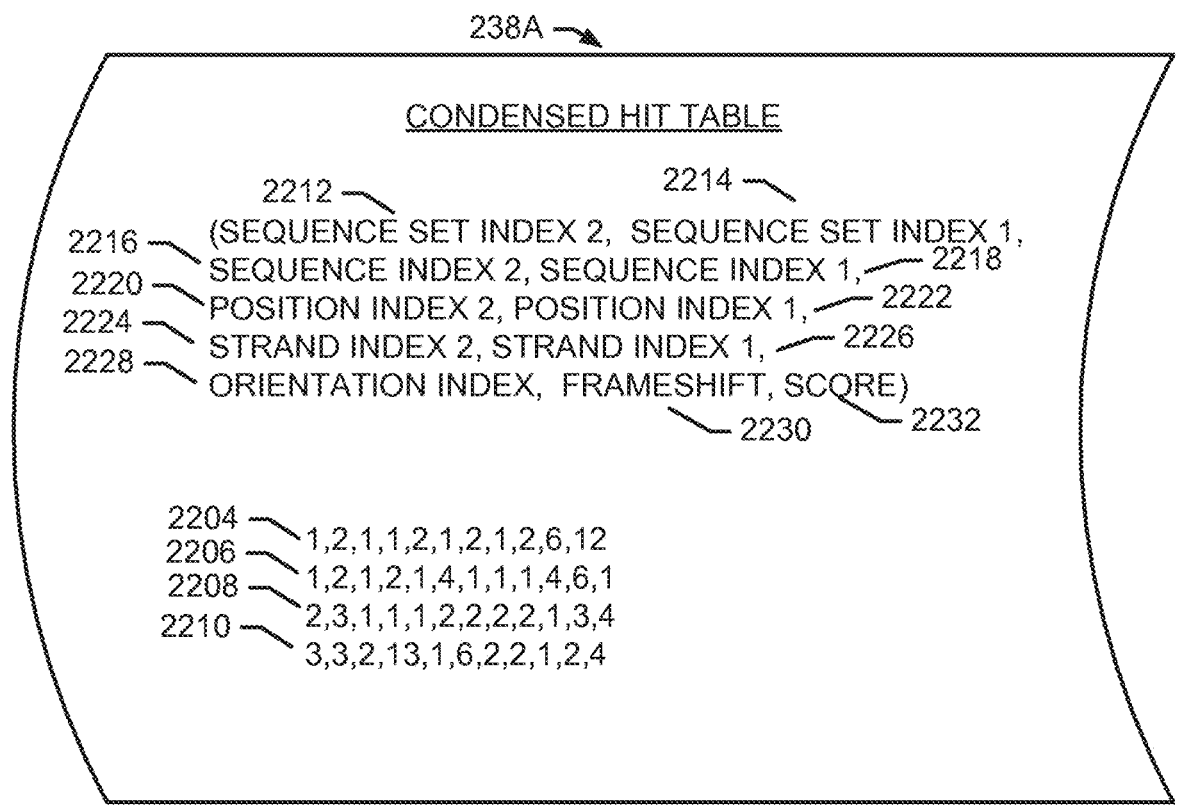
FIG. 22 is a diagram of a condensed hit table in accordance with an embodiment of the present invention.

FIG. 22 is an illustration of an exemplary condensed hit table 238A.

The condensed hit table 238A includes one or more condensed hit table entries 2204-2208. Each condensed hit table entry includes one or more indices 2212-2230 assigned to the entry by the hit determination system 216. The indices include the sequence set index 2 2212, the sequence set index 1 2214, the sequence index 2 2216, the sequence index 1 2218, the position index 2 2220, the position index 1 2222, the strand index 2 2224, the strand index 1 2226, the orientation index 2228, and the frameshift 2230. In addition, each condensed hit table entry includes a score 2232, which specifies the number of times the hit table entry was repeated in the sorted hit table. The condensed hit table 238 is processed by the post processing system 240.

Post Processing System

Figure 23:
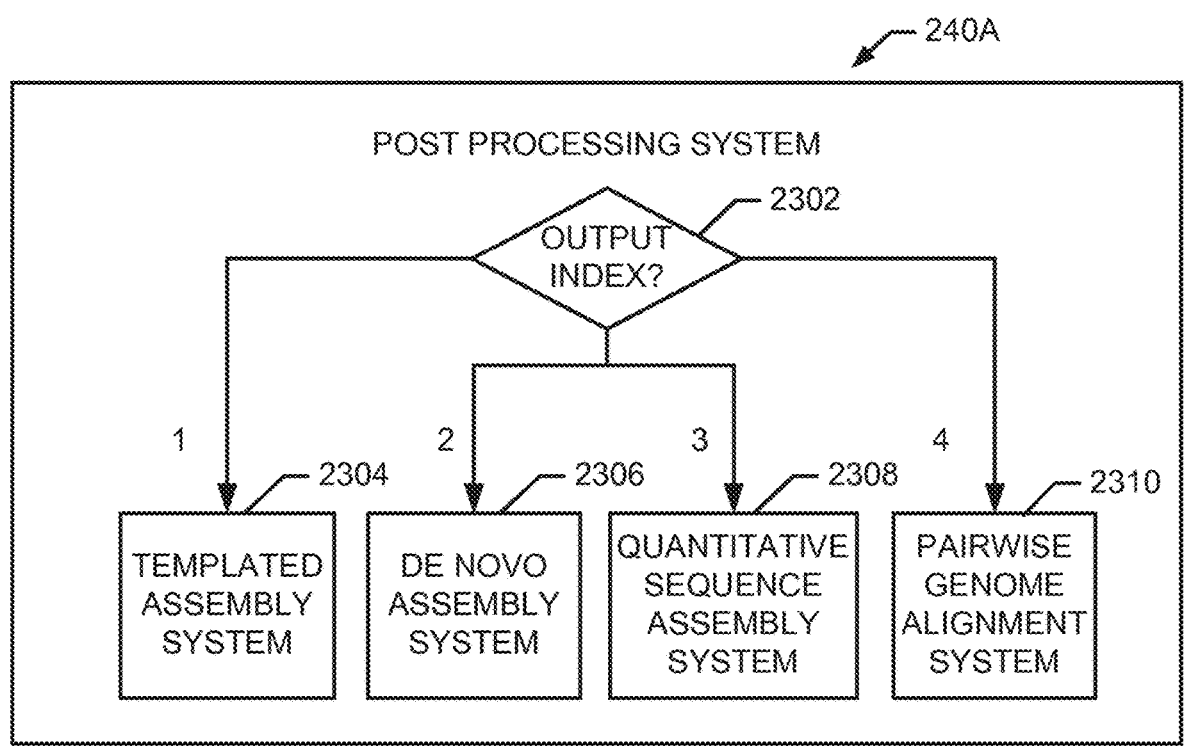
FIG. 23 is a flow chart of the processes of a post processing system in accordance with an embodiment of the present invention.

FIG. 23 is an illustration of an exemplary post processing system 240A.

The post processing system includes four different systems 2304-2310 that process the condensed hit table 238A using four different algorithms depending on whether the output index at step 2302 is 1, 2, 3, or 4. Alternately, the post processing system may include one or more of the four different systems 2304-2310.

The templated assembly system 2304 processes the condensed hit table entries to produce an initial assembly of a first sequence set 202 using a second sequence set 204 as a template. In this system, the first sequence set 202 may be a set of reads sequenced from a DNA sample, and the second sequence set 204 may be a set of chromosome sequences from a genetic database. Other examples exist.

The de novo assembly system processes the condensed hit table entries to produce an initial assembly of a first sequence set 202 using a copy of the first sequence set 202 as the template for assembly. In this system, the first sequence set 202 may be a set of reads sequenced from an organism for which no previous sequence sets exist. In this case, the first sequence set 202 is assembled using a copy of the first sequence set 202 as the template. In one aspect, the second sequence set 204 is the copy of the first sequence set 202. Other examples exist.

The quantitative sequence assembly system 2308 processes the condensed hit table entries to produce a summary of the number of matches between a second sequence set 204 and a first sequence set 202 in which the summary is organized by location in the second sequence set 204. In this system, the first sequence set 202 may be a set of sequenced mRNA or DNA fragments from a patient, and the second sequence set 204 may be a set of gene sequences associated with a genetic product of interest. For example, a genetic product of interest may be a gene that is upregulated in response to a disease state in a patient. Other examples exist.

The pairwise genome alignment system 2310 processes the sorted hit table entries to produce an initial alignment of an organism's genome using an existing sequenced genome as a template. In this system, the first sequence set 202 may be a set of reads from the entire genome of an organism, and the second sequence set 204 may be a sequenced genome from a genetic database. Because of the long sequence length of the genome sequences, the incidence of random sequence errors due to errors in obtaining the reads from the genome, mutations, and other error sources may be higher than for shorter sequence lengths. The pairwise genome alignment accounts for these errors by skipping past regions that appear to harbor potential mutations or other errors that might otherwise confound the assembly process. The pairwise genome alignment system 2310 processes the sorted hit table 234, not the condensed hit table 238. In one embodiment of the pairwise genome alignment system 2310, the hit table condensing system 236 and the condensed hit table 238 are not used or are not present.

Templated Assembly System

Figure 24:
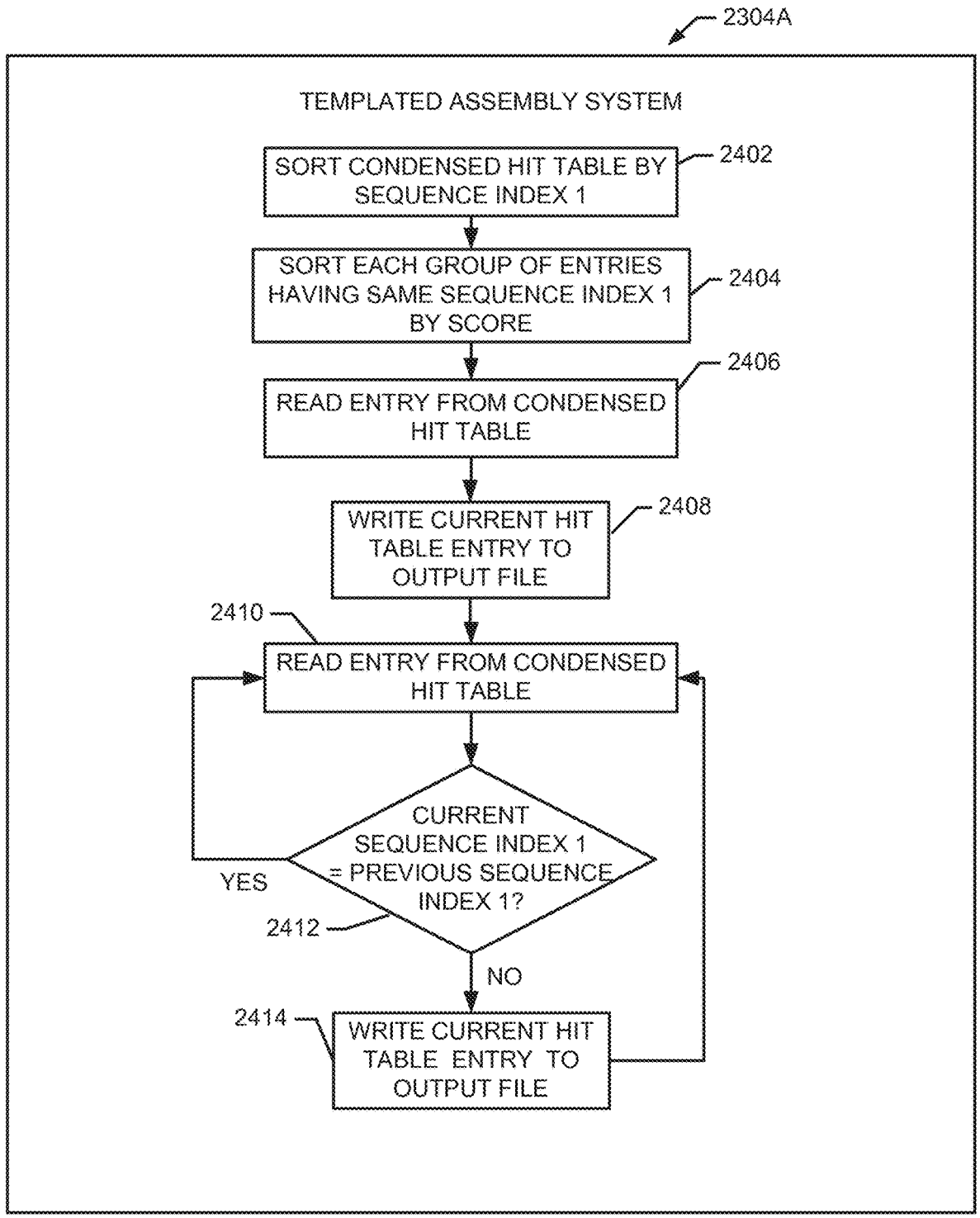
FIG. 24 is a block diagram of a templated assembly post processing system in accordance with an embodiment of the present invention.

FIG. 24 is an illustration of an exemplary templated assembly system 2304A. To produce an initial assembly of a first sequence set 202, the templated assembly system 2304 sorts all entries of the condensed hit table 238 by sequence index 1 2214 at step 2402, and then sorts each group of condensed hit table entries having the same sequence index 1 2214 by score 2232 at step 2404. The condensed hit table is now arranged into groups having the same sequence index 1, and the first entry in each group has the highest score of its group. The remaining steps of the templated assembly system 2304A locates the remaining condensed hit table entries having the highest score for each of the other groups of condensed hit table entries corresponding to each other sequence index 1 2214.

In one aspect, the coverage of each condensed hit table entry is evaluated and all entries not meeting a minimum coverage threshold may be removed prior to processing the condensed hit table 238 by the templated assembly system 2304A. In one aspect, any condensed hit table entries with a score falling under a minimum threshold score are deleted. In another aspect, any condensed hit table entries with a coverage score that is less than a minimum coverage threshold are deleted prior to processing by the templated assembly system 2304A. In this aspect, the minimum coverage threshold may be specified as about twenty nucleotide bases or about fifty percent of the length of the read sequence from sequence set 1 202, whichever is greater. Because each read sequence may have a different length, the minimum coverage threshold may be calculated for each read sequence. Once the condensed hit table entries having insufficient coverage have been removed, processing by the templated assembly system 2304A proceeds.

The first entry of the condensed hit table is read at step 2406 and is written to the output file at step 2408. The next condensed hit table entry is read at step 2410, and the current sequence index 1 is compared to the previous sequence index 1 of the previous condensed hit table entry at step 2412. If the current sequence index is the same as the previous sequence index 1, the current condensed hit table entry is from the same group as the previous condensed hit table entry, and therefore has a lower score. In this case, a new condensed hit table entry is read at step 2410.

If the current sequence index 1 is not the same as the previous sequence index 1 at step 2412, then the current condensed hit table entry is the first of a new group having the same sequence index 1, and which also has the highest score of the group. So, the current condensed hit table entry is written to the output file at step 2414.

The resulting output file is a list of all of the condensed hit file entries having the highest score among all of the other entries having the same sequence index. This list represents an initial assembly of sequence set 1, since each entry of the output file specifies the alignment of each sequence in sequence set 1 that resulted in the highest number of mer matches between sequence set 1 and sequence set 2.

De Novo Assembly System

In one aspect, the de novo assembly system 2306 processes a condensed hit table resulting from the matching of a first sequence set with a second sequence set, in which the second sequence set is a copy of the first sequence set. The de novo assembly system is used when assembling a sequence set for which no template exists.

Figure 25:
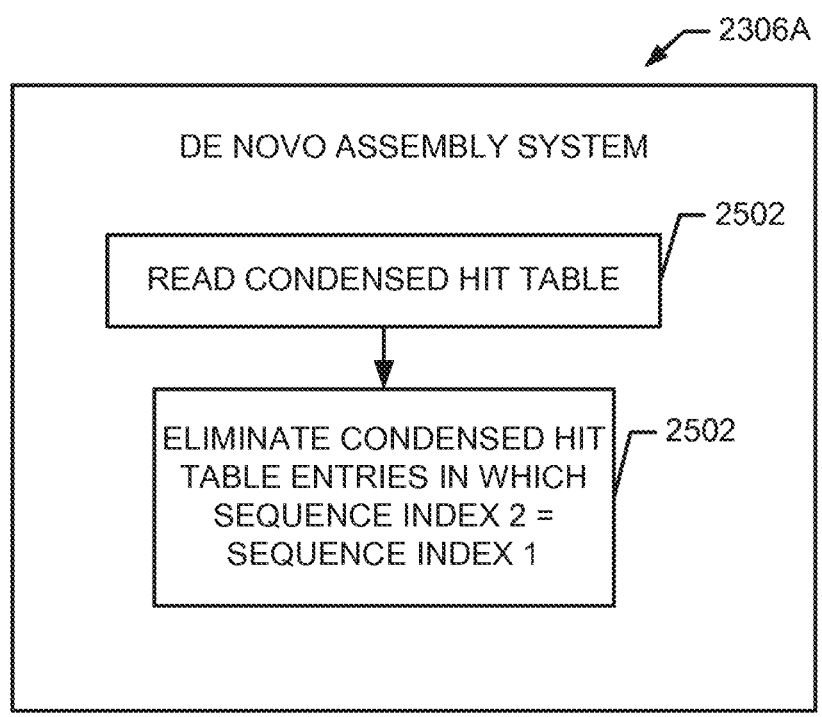
FIG. 25 is a block diagram of a de novo assembly post processing system in accordance with an embodiment of the present invention.

FIG. 25 is an illustration of an exemplary de novo assembly system 2306A. The de novo assembly system 2306A reads in the condensed hit table 238 at step 2502 and eliminates all condensed hit table entries in which sequence index 1 is equal to sequence index 2. The entries in which sequence index 1 is equal to sequence index 2 are those cases in which a sequence from sequence set 1 is matched with the copy of the same sequence in sequence set 2.

The output file generated by the de novo assembly system 2306A is the concentrated hit table with the hits of sequences against their own copies removed. This output file provides a summary of the matches between each strand of sequence set 1 against all of the other strands of sequence set 1.

Figure 41:
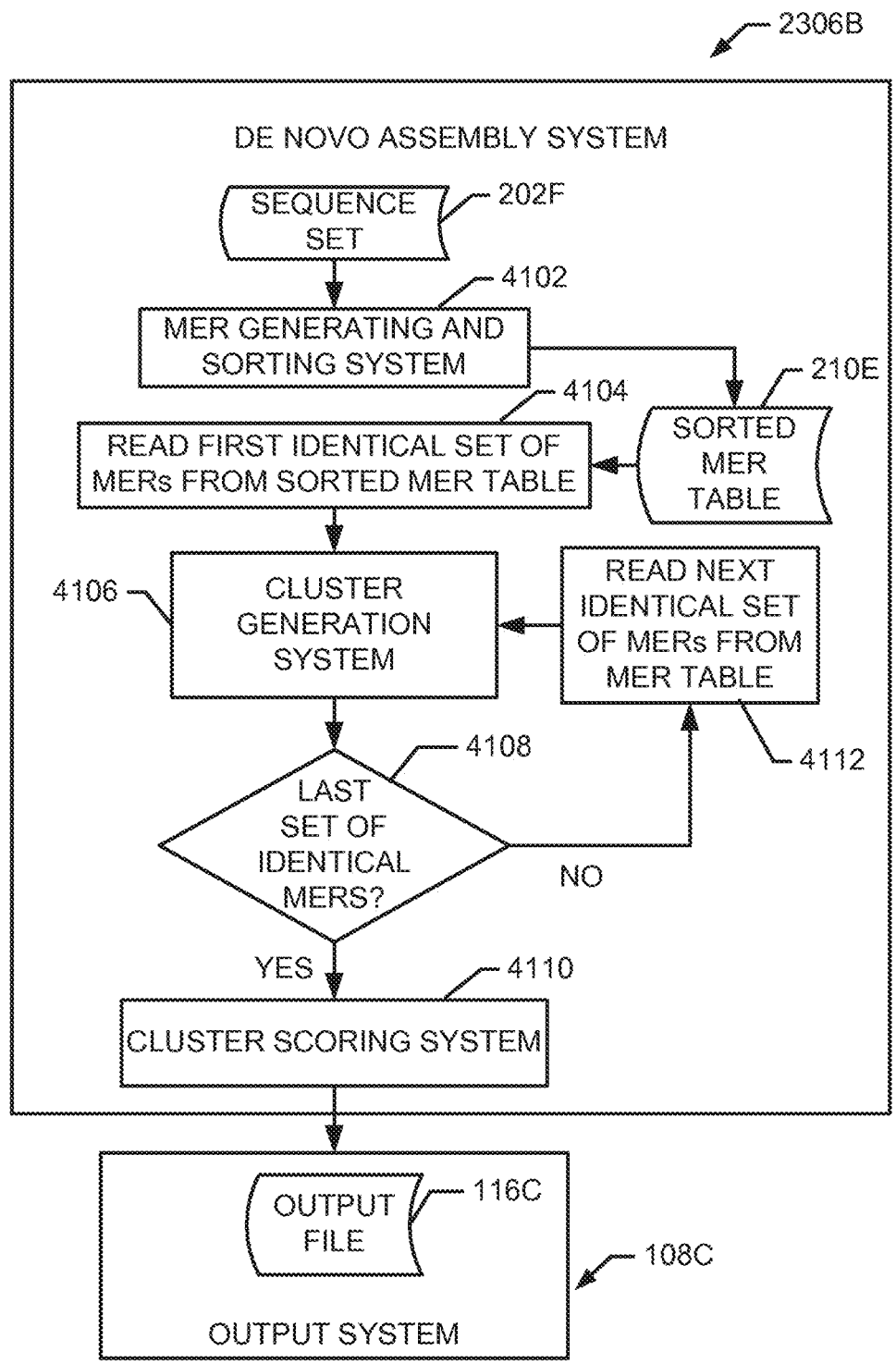
FIG. 41 is a block diagram of a de novo assembly system in accordance with an embodiment of the present invention.

In another aspect, a cluster-based de novo assembly system 4102, shown in FIG. 41, processes a sorted mer table 210E generated from a set of read sequences using methods previously described in FIG. 2 and FIG. 5A. In this aspect, clusters of read sequences are formed based on their shared mer nucleotide sequences. In this context, a cluster refers to a group of read sequences that are associated due to at least one or more shared mer sequences. As more mer sequences from the sorted mer table 210E are processed, the cluster-based assembly system may dynamically form new clusters or combine existing clusters based on the quantities of shared mer nucleotide sequences within the existing clusters.

The cluster-based de novo assembly system 4102 achieves reduced processing times relative to the previously described de novo assembly system 2306 (see FIG. 25) due to several significant reductions in the amount of data processed. The entries of the sorted read mer table are internally compared and matched, rather than comparing one read mer table to a duplicate copy of the same read mer table. In addition, the groups of identical mers are initially screened to exclude mers generated from SNPs, erroneous sequences, or highly repeated sequences that might confound the de novo assembly, further reducing the amount of data manipulated during processing.

An exemplary cluster-based de novo assembly system 4102 is illustrated in FIG. 41. A first group of mers is read from a sorted mer table 210E at step 4104. Each mer in this group possesses identical mer nucleotide sequences. The group of mers is processed by a cluster generation system 4106 which assesses the number of read sequences used to generate the mer sequences. The cluster determination system 4106 assesses whether sufficient numbers of shared mer sequences exist to justify: 1) forming a new cluster of read sequences, 2) combining previously unassigned read sequences to one or more existing clusters, or 3) combining two or more existing clusters to form a larger merged cluster. At step 4108, it is determined whether any additional groups of identical mer sequences remain in the sorted mer table 210E to be processed. If additional mers remain to be processed, the next group of identical mers are read in at step 4110 and assessed by the cluster generation 4106 as before. If no groups of identical mer sequences remain to be processed, the clusters are scored in a cluster scoring system 4112 which generates an output file 116C which may be submitted to a de novo assembler device.

Figure 42:
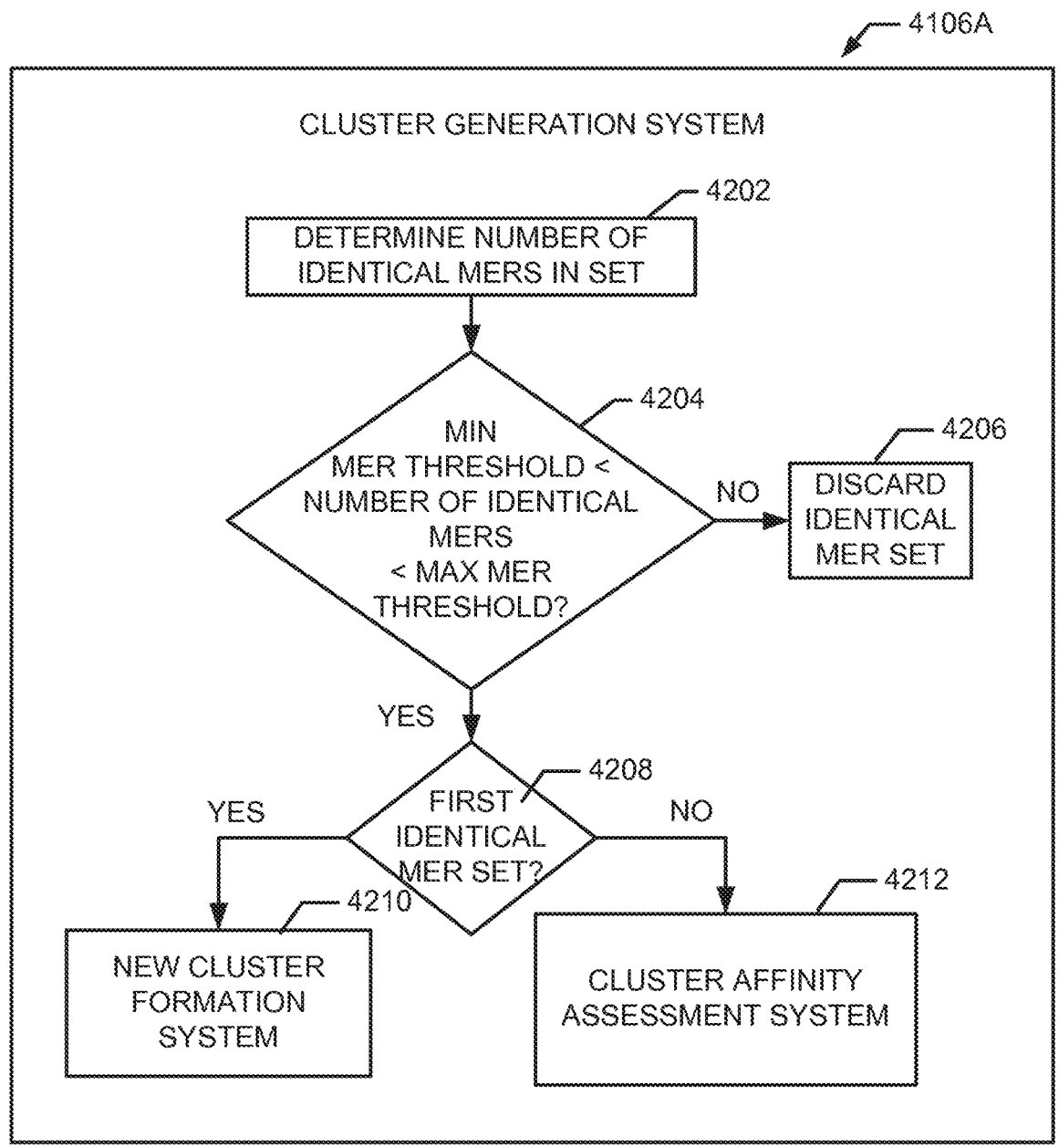
FIG. 42 is a block diagram of a cluster generation system in accordance with an embodiment of the present invention.

An exemplary cluster generation system 4106A, illustrated in FIG. 42, determines the number of identical mer sequences in each group of identical mers at step 4202 and assessed at step 4204 to determine whether the number of identical mers is greater than a minimum mer threshold and less than a maximum mer threshold. If the number of mers in the group is less than the minimum mer threshold, the set of mers is discarded at step 4206, because the mer group contains too few mers to provide useful information for grouping the sequences of the mer group into a cluster. If the number of mers in the group is greater than the maximum mer threshold, the mer group is also discarded. If too many mers share a common mer nucleotide sequence, the mer may be part of a highly repeated sequence, and the inclusion of this group of mers may confound the de novo assembly process.

The minimum mer threshold and maximum mer threshold may be specified based on the estimated coverage of the genome by the sequenced reads. In this context, the estimated coverage is calculated by dividing the total number of nucleotides in all sequenced reads in the read set by the estimated number of nucleotides in the genome. In one aspect, the minimum mer threshold may be set at about 20% of the estimated genome coverage of the sequenced read set. In another embodiment, the maximum mer threshold may be set at about 200% of the estimated genome coverage.

If the number of mers within the set of identical mers falls between the minimum mer threshold and the maximum mer threshold at step 4204, the set of identical mers is further processed. If the set of identical mers is the first set processed, none of the mers have been assigned to a cluster, and the group is formed into a cluster by the new cluster formation system 4210. If the group of identical mer sequences is not the first group to be processed, the group of identical mer sequences is processed further using the cluster affinity assessment system 4212 to determine whether the group of mers should be merged with an existing group, formed into a new cluster, or whether existing clusters should be merged based on the degree of overlap by any previously unassigned sequences within the group of identical mers.

Figure 43:
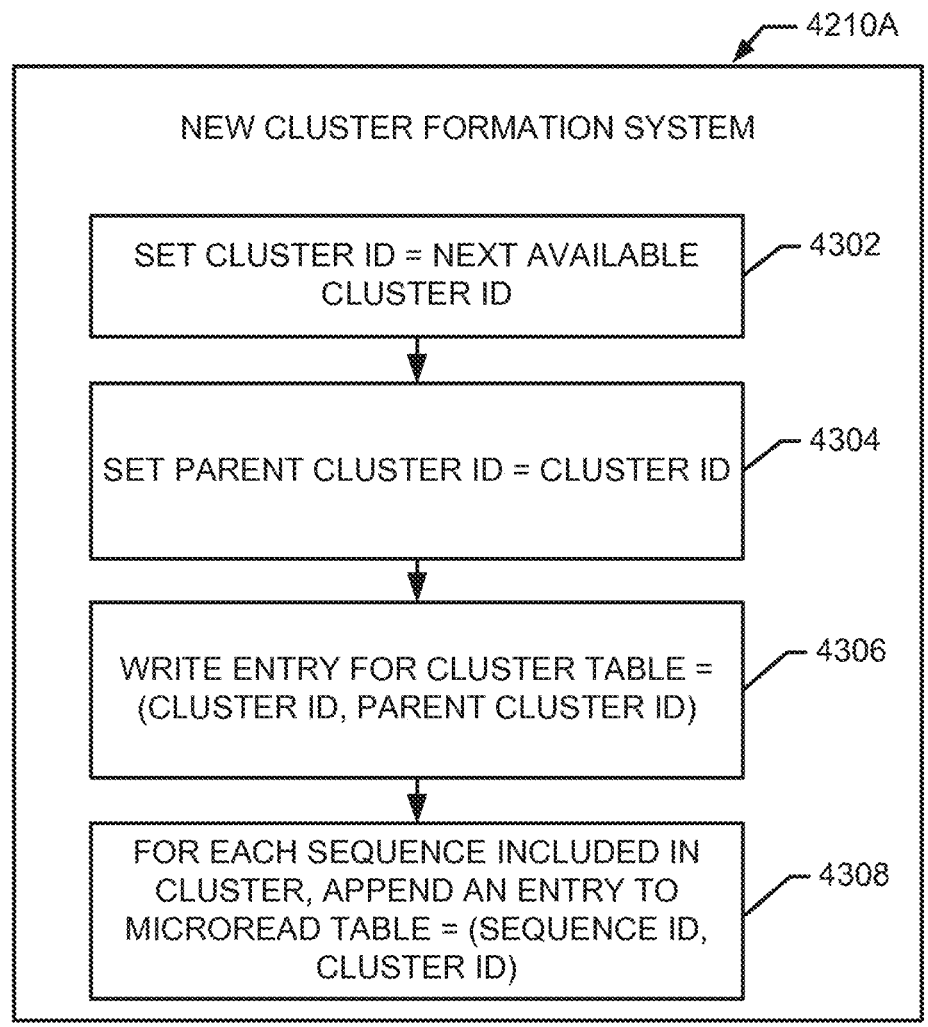
FIG. 43 is a block diagram of a new cluster formation system in accordance with an embodiment of the present invention.

An exemplary new cluster formation system 4210A is illustrated in FIG. 43. The number of unassigned sequences in the mer group (N_unassigned) is determined and compared to a new cluster threshold at step 2410. The new cluster threshold is the minimum number of unassigned sequences in a mer group that support forming a new cluster. In one aspect, the new cluster threshold may be less than about half of the estimated coverage of the genome. In another aspect, the new cluster threshold may be about 2 sequences.

A cluster is formed by specifying a cluster ID for the new cluster at step 4302, setting the parent cluster ID to same value as the cluster ID at step 4304, and writing a cluster table entry that includes the cluster ID and the parent cluster ID at step 4306. Each cluster table entry, which documents a single cluster, is typically of the form (cluster ID, parent cluster ID). The cluster ID documents the original cluster to which each mer group was assigned, and the parent cluster ID documents any clusters with which the original cluster was merged during the processing of subsequent mer groups. For example, if a mer group is the fifth cluster group to be processed by the system and did not merge with any existing clusters at the time the mer group was processed, then a cluster table entry of (5,5) would be appended to the cluster table. As another example, if the fifth cluster was later merged with the $3^{rd}$ cluster, the parent cluster ID of this cluster's table entry would be changed from 5 to 3 to indicate that the $5^{th}$ cluster was merged with the $3^{rd}$ cluster, resulting in a revised cluster table entry of (5,3). By one convention, the cluster that was formed earliest (i.e. the cluster that has the lowest cluster ID) is the parent cluster with which the later-formed cluster is merged. Other conventions may also be used in other aspects. In other embodiments, the cluster table entries may include additional statistical information about the clusters such as the estimated number of read sequences in the cluster and the number of mers that the sequences of the cluster have in common.

In addition to the cluster table entries, a microread table containing the read sequence and the cluster to which the read sequence is assigned is generated to further document the clusters. Referring back to FIG. 23, a microread table entry with the format (sequence ID, cluster ID) is appended to a microread table at step 4308 for every sequence included in a cluster.

Figure 44:
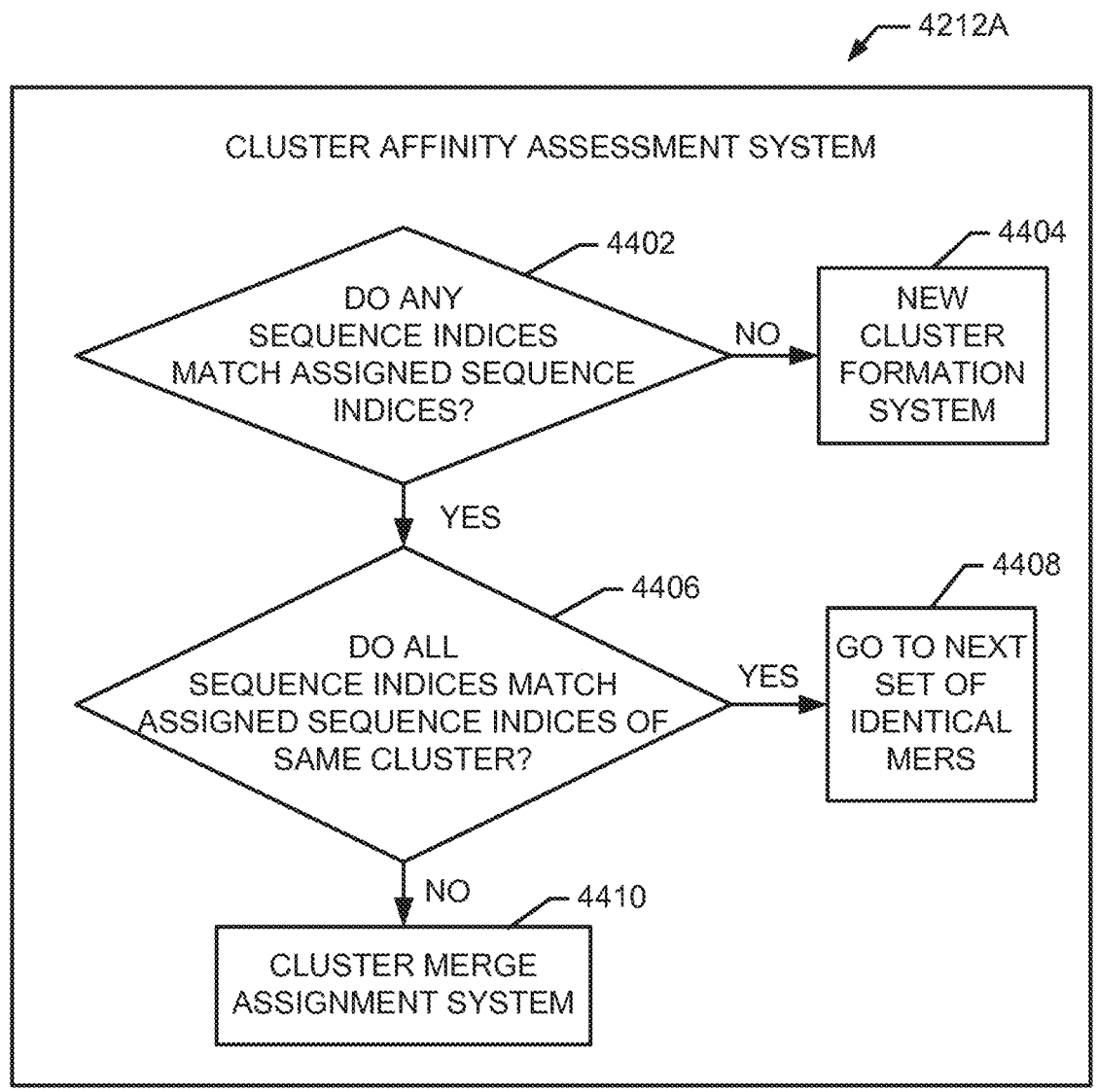
FIG. 44 is a block diagram of a cluster affinity assessment system in accordance with an embodiment of the present invention.

An exemplary cluster affinity assessment system 4212A is illustrated in FIG. 44. At step 4402, the sequence indices of all mers in the matching mer group are compared to sequence indices in the microread table that are already assigned to existing clusters. If none of the sequence indices of the mer group match any of the microread table entries, then none of the sequences in the mer group have been assigned to an existing cluster, indicating that the mer group may form a new cluster. In this case, the entire mer group is processed by the new cluster formation system 4210A. If any of the sequence indices of the mer group have been previously assigned to an existing cluster at step 4406, then it is determined whether all of the sequence indices match sequence indices that are previously assigned to the same cluster at step 4406. If all sequences have been previously assigned to the same cluster, then the mer group offers no additional cluster grouping information, and the next mer group is read and processed at step 4408. If some of the sequence indices in the mer group were previously assigned to one cluster and other sequence indices in the mer group were previously assigned to a second cluster, the mer group is further processed by a cluster merge assignment system 4410.

Figure 45:
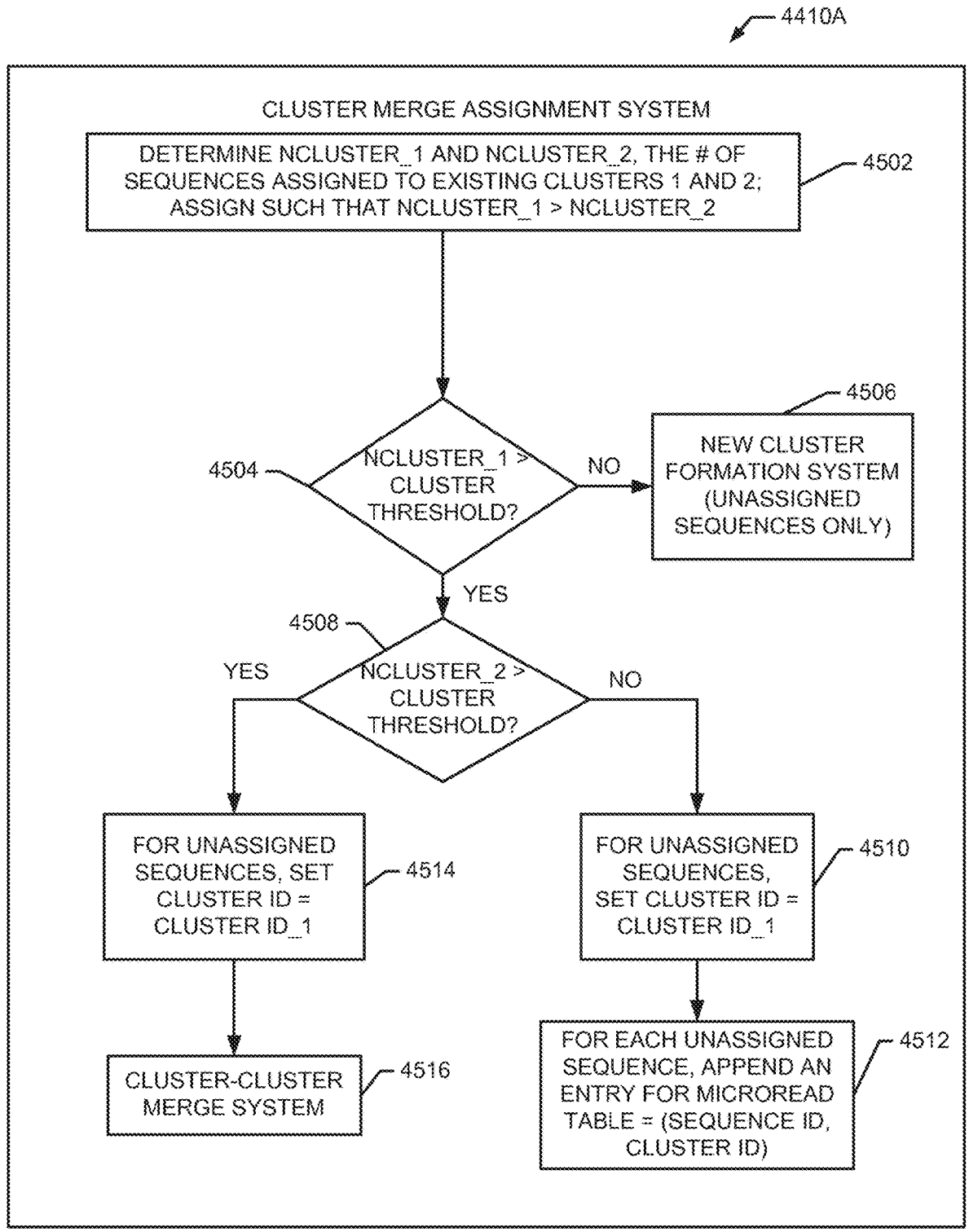
FIG. 45 is a block diagram of a cluster merge assignment system in accordance with an embodiment of the present invention.

FIG. 45 illustrates an exemplary cluster merge assignment system 4410A. This system further assesses the mer group to determine whether sufficient evidence exists to form a new cluster with the previously unassigned read sequences, to add the previously unassigned sequences to an existing cluster, or to merge two existing clusters into a single cluster. The numbers of sequences that were previously assigned to a first existing cluster (NCLUSTER_1) and to a second existing cluster (NCLUSTER_2) are determined at step 4502. For purposes of illustration, only two existing clusters are illustrated in FIG. 45. In other aspects, however, the cluster merge assignment system 4410A may assess the number of sequences assigned to three or more existing clusters.

Because the existing clusters may not be arranged in order of cluster size, some ambiguity exists in comparing the degree of overlap of the mer group processed by the cluster merge assignment system 4410A with the first and second existing clusters. To simplify the analysis process, in one aspect NCLUSTER_1 and NCLUSTER_2 are assigned such that NCLUSTER_1>NCLUSTER_2. Using this convention, the mer group processed by the cluster merge assignment system 4410A has more sequences in common with the first cluster than with the second cluster.

At step 4504, NCLUSTER_1 is compared to a cluster threshold. The cluster threshold is a minimum number of sequences in a mer group under consideration that must be previously assigned to an existing cluster to support adding any unassigned sequences in the mer group to that existing cluster. In one aspect, the cluster threshold may be less than about one half the coverage. In another aspect, the cluster threshold may range from about about 2 to about 4. In yet another aspect, the cluster threshold may be about 2. If NCLUSTER_1 is less than the cluster threshold, than none of the previous clusters possess sufficient sequence overlap to support any merging of sequences, and the unassigned sequences in the mer set are processed by the new cluster formation system 4506 to form a new cluster if there are sufficient numbers of unassigned sequences in the mer group.

If NCLUSTER_1 is greater than the cluster threshold at step 4504, NCLUSTER_2 is compared to the cluster threshold at step 4508. If NCLUSTER_2 is less than the cluster threshold, then the unassigned sequences in the mer group are added to cluster 1. The cluster ID of all unassigned sequences is set to CLUSTER ID_1 (the index of cluster 1) at step 4510, and a microread table entry containing (SEQUENCE ID, CLUSTER ID) is created in the microread table for each unassigned sequence in the mer group at step 4512. Because no new cluster is formed, no new entries to the cluster table are created.

If NCLUSTER_2 is greater than the cluster threshold, then both the first and the second clusters have sufficient numbers of assigned sequences in the mer set to support merging the unassigned sequences, and therefore the merging of the first and second clusters is supported. The unassigned sequences are assigned the CLUSTER ID_1 corresponding to the first cluster at step 4514, and the first and second clusters are merged by the cluster-cluster merge system 4516.

Figure 46:
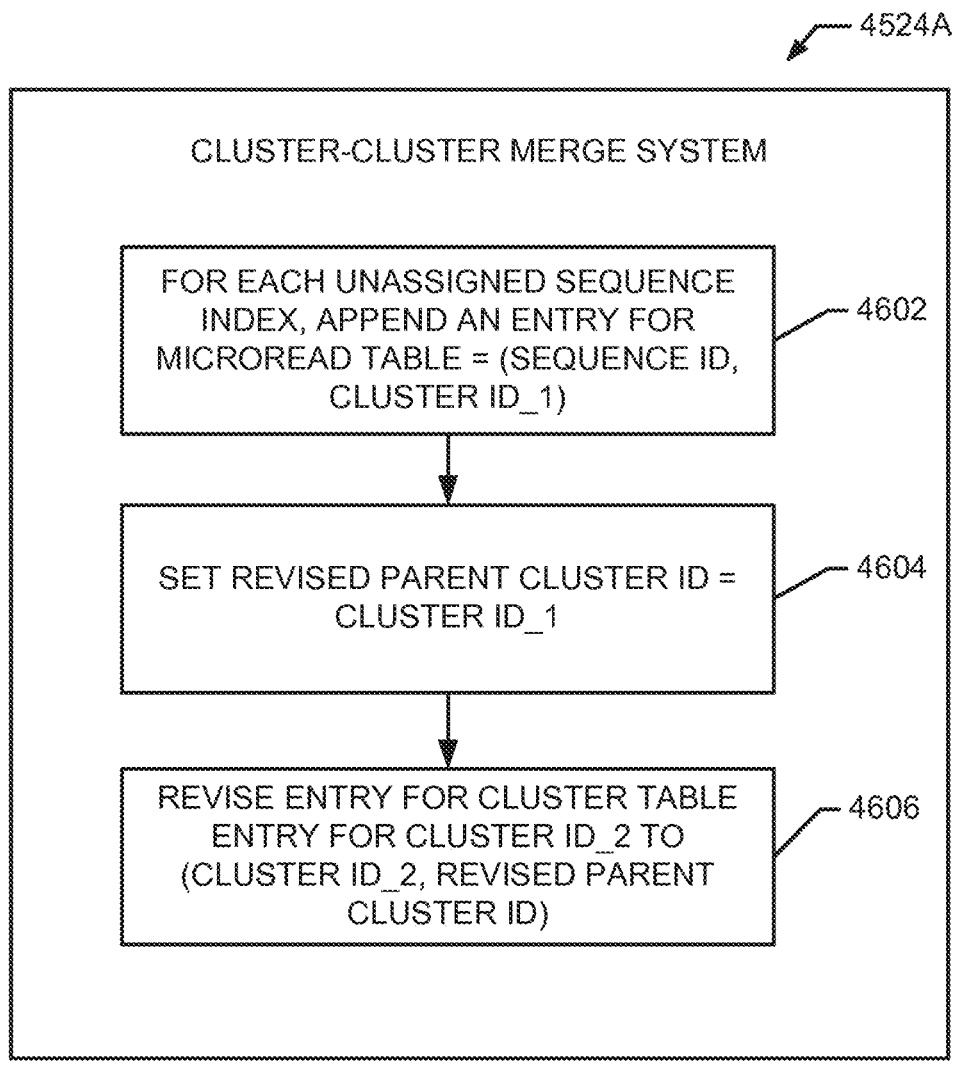
FIG. 46 is a block diagram of a cluster-cluster merge system in accordance with an embodiment of the present invention.

An exemplary cluster-cluster merge system 4524A is illustrated in FIG. 46. A microread table entry (SEQUENCE ID, CLUSTER ID) is appended to the microread table at step 4602 for each unassigned sequence in the mer set. The revised parent cluster ID is set to the cluster ID of the first cluster, CLUSTER ID_1, at step 4604. The cluster table entry corresponding to the second cluster is revised to replace the parent cluster ID with the cluster ID of the first cluster to indicate that the second cluster is now merged with the first cluster.

Once all mer groups from the sorted mer table 210E have been processed in the manner described above, the cluster table will be analyzed to determine whether each of the clusters is a candidate for contig creation. In this context, a contig is a set of overlapping DNA fragments used in a sequence assembly process to assemble the DNA sequence of a larger DNA strand that may include a gene, a chromosome, or a genome.

If a cluster chain satisfies the criteria to qualify as a potentially useful contig, the read sequences that constitute the cluster chain will be gathered together and submitted to a DNA Assembler device. In one aspect, a cluster chain is qualified as a contig if the cluster chain includes at least about 100 read sequences. In another aspect, a cluster chain is qualified as a contig if the cluster includes between about 100 and about 1,000,000 read sequences. In yet another aspect, the qualification of a cluster chain as a contig is determined based on an estimated contig length to be created by the cluster chain, efined as (number of read sequences in a cluster chain*average length of a read sequence)/(coverage). In this aspect, if the estimated contig length is greater than about 2000 bases, the cluster chain is qualified for inclusion as a contig. Alternatively, in this aspect, if the estimated contiglength is from about 2000 bases to about 1,000,000 bases, the cluster chain is qualified for inclusion as a contig.

Quantitative Sequence Assembly System

Figure 26:
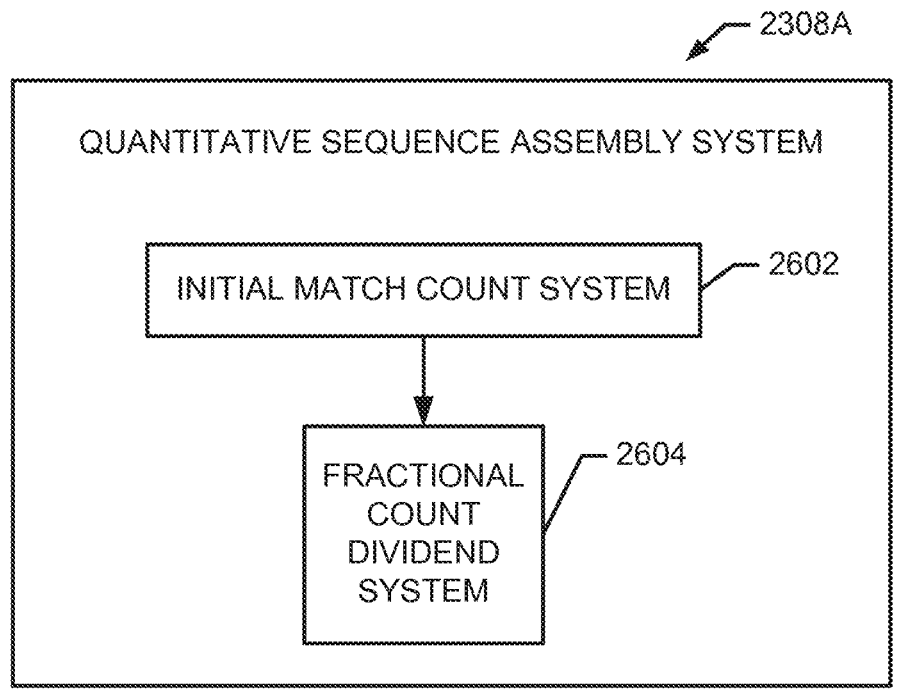
FIG. 26 is a block diagram of a quantitative sequence assembly post processing system in accordance with an embodiment of the present invention.

FIG. 26 is an illustration of an exemplary quantitative sequence assembly system 2308A. The quantitative sequence assembly system 2308A processes the entries of the condensed hit table to determine a score for each sequence of the second sequence set based on the number of hits a first sequence set had with each sequence of a second sequence set.

The quantitative sequence assembly system 2308A includes an initial match count system 2602. The initial match count system 2602 sorts the condensed hit table by sequence index 1, and then sorts each group of entries having the same sequence 1 by sequence 2.

For each group of condensed hits for a particular sequence from sequence set index 1, the initial match count system 2602 eliminates all condensed hit table entries in the group that have scores less than a minimum threshold score and retains only the entry or entries having the maximum score of the group by eliminating all hit table entries having less than the maximum score within the group. If a single condensed hit table entry remains after the elimination process described above, a match counter assigned to the particular sequence from sequence set 2 is increased in value. If two or more entries remain after the elimination process described above, the condensed hit table entries are written to a repeat assignments table for subsequent analysis by the fractional count dividend system 2604.

The fractional count dividend system 2604 determines the contribution of the other entries of the condensed hit table that did not meet the criterion described above. The score of each sequence of the second sequence set is increased by an amount that is proportional to the frequency of matches between each of the sequences of the second sequence set and the first sequence set.

Figure 27:
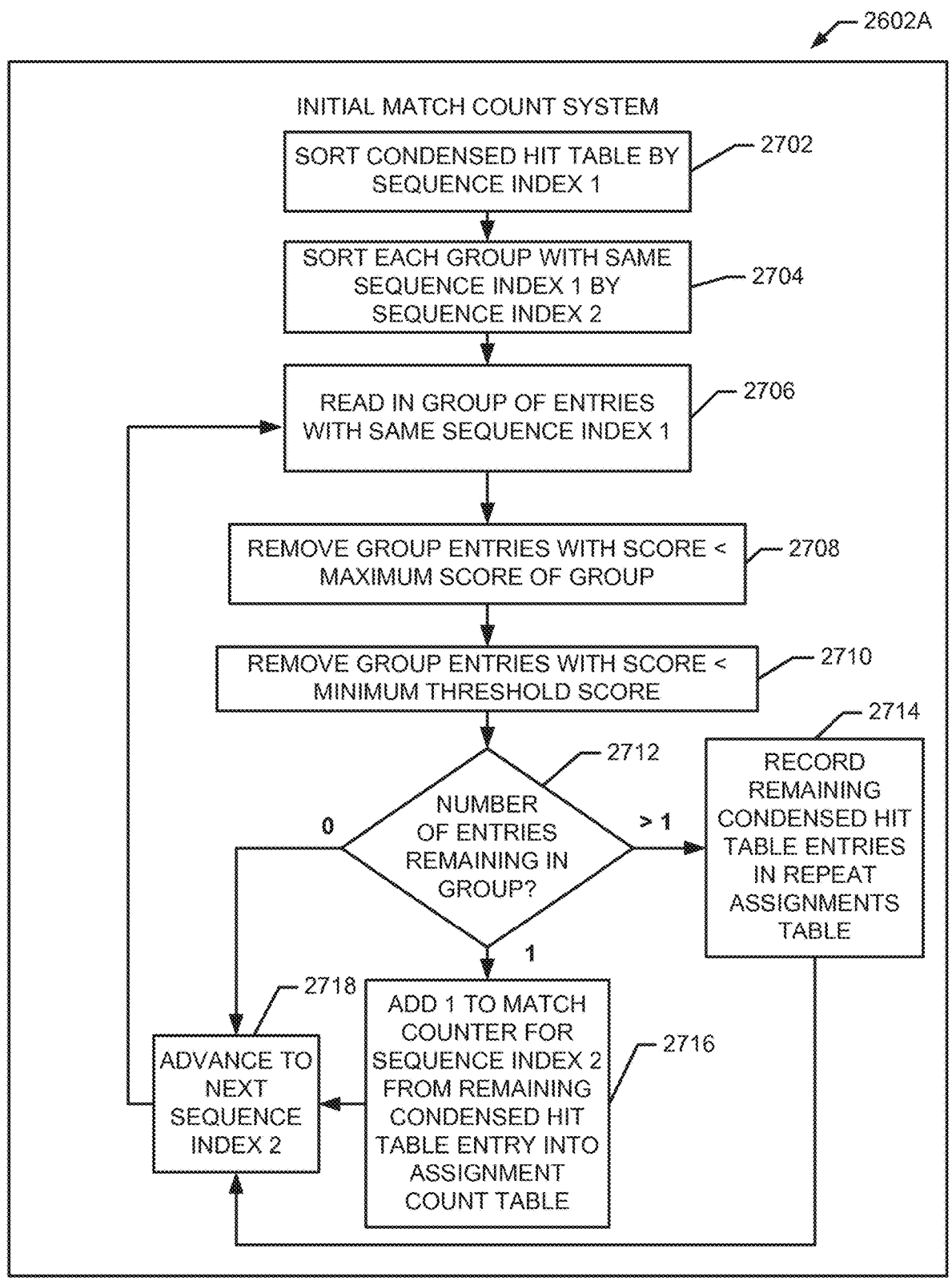
FIG. 27 is a block diagram of an initial match count system in accordance with an embodiment of the present invention.

FIG. 27 is an illustration of an exemplary initial match count system 2602A. The condensed hit table 238 is sorted by sequence index 1 at step 2702, and each group of hit table entries with the same sequence index 1 is sorted by sequence index 2 at step 2704. A group of entries that have the same sequence index 1 is read at step 2706. The maximum score among all of the entries in the group is determined, and those entries in the group that have scores less than the maximum score are removed from the group at step 2708. The remaining entries of the group with scores less than a minimum threshold score are removed from the group at step 2710. The minimum threshold score is a value specified by the user to exclude any matches specified by a condensed hit table that fall below a significant level. In one aspect, the minimum threshold score may range between a score of 1 and a score that corresponds to 100% of the read length. In another aspect, the minimum threshold score may be a score that corresponds to about 10% of the read length.

The number of entries remaining in the group is assessed at step 2712. If more than one entry remains in the group, then the remaining entries are written to a repeat assignments table at step 2714. If only one entry remains in the group, a score of 1 is added to a match counter assigned to the sequence index 2 indicated by the remaining entry at step 2716. The match counter is a number that tracks the frequency of matches between the sequences of sequence set 1 and each of the sequences of sequence set 2. One match counter is assigned to each sequence of sequence set 2, and the match counters are stored in an assignment count table. The initial match count system 2602A advances to the next sequence index 1 at step 2718 after step 2716 or if no entries remain in the group at step 2712.

In the course of processing the condensed hit table, the initial match count system generates two tables: an assignment count table and a repeat assignments table. The assignment count table contains a list of match counters, and each match counter specifies the number of times of the sequences from sequence set 1 produced mer matches with each of the sequences from sequence set 2. Each match counter in the assignment count table corresponds to one of the sequences from sequence set 2. The repeat assignments table stores the condensed hit table entries that specified matches in which a sequence from sequence set 1 matched two or more sequences from sequence set 2 with equal frequency.

Figure 28:
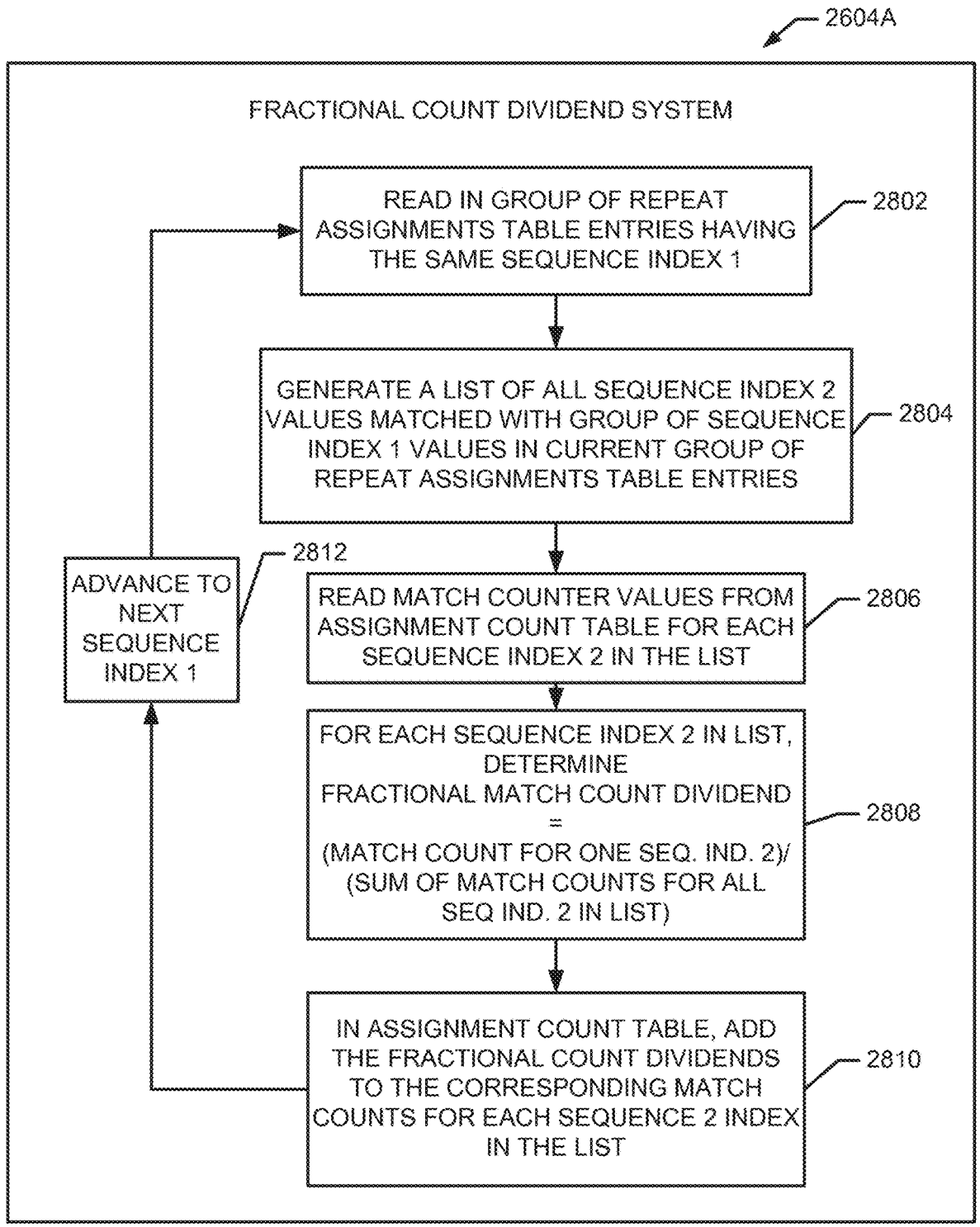
FIG. 28 is a block diagram of a scoring process of a fractional count dividend system in accordance with an embodiment of the present invention.

FIG. 28 is an illustration of an exemplary fractional count dividend system 2604A. The fractional count dividend system 2604A processes the entries of the repeat assignments table and adds a weighted average score to each match count based on the proportion of entries in the repeat assignments table that specify each sequence of sequence set 2. At step 2802, a group of repeat assignment table entries that all have the same sequence index 1 are read in. A match list containing all of the sequence indices from sequence set 2 that appear in one or more repeat assignment table entries in the current group is generated at step 2804. The match counter values assigned to each of the sequence index 2 entries in the match list is read from the assignment count table at step 2808. For each sequence index 2 in the match list, a fractional match count dividend is determined by dividing the match count for each sequence index 2 by the sum of the match counts for all of the sequence indices in the match list at step 2808. The fractional match count dividends are added to the corresponding match counts for each sequence index 2 in the match list at step 2810. The next group of repeat assignment table entries having the same sequence index 1 is started at step 2812.

The output file of the quantitative sequence assembly system is the assignment count table that contains an entry for each sequence index 2 of sequence set 2. Each assignment count table entry includes a sequence index 2 and the match count determined by the quantitative sequence assembly system 2308A for that sequence. The match count for each sequence index is used as a signal to quantify the coverage or expression of each sequence of sequence set 2. In one aspect, the match count for a given sequence is a raw signal for the coverage or expression of the sequence. In other aspects, the match count may be used to determine other normalized signal quantities that are well-known in the art.

In one aspect, the hit count may be used to express a signal as reads mapped per kilobyte of target sequence (RPK), as shown in equation 1 below:

$$RPK = \frac{\text{match\_count}}{(\text{target\_sequence\_length}/1{,}000)} \quad (1)$$

where target_sequence_length is the total number of nucleotides of all sequences in sequence set 2.

In one aspect, the hit count may be used to express a signal as reads mapped per million (RPM), as shown in equation 2 below:

$$RPM = \frac{\text{match\_count}}{(\text{n\_reads}/1{,}000{,}000)} \quad (2)$$

where n_reads is the total number of read sequences from sequence set 1 that were mapped onto sequence set 2.

In another aspect, the hit count may be used to express a signal as reads mapped per kilobyte of target sequence, per million total mapped reads (RPKM), as shown in equation 3 below:

$$RPKM = \frac{\text{match\_count}}{(\text{target\_sequence\_length}/1000)(\text{n\_reads}/1{,}000{,}000)} \quad (3)$$

Pairwise Genome Alignment System

Figure 29:
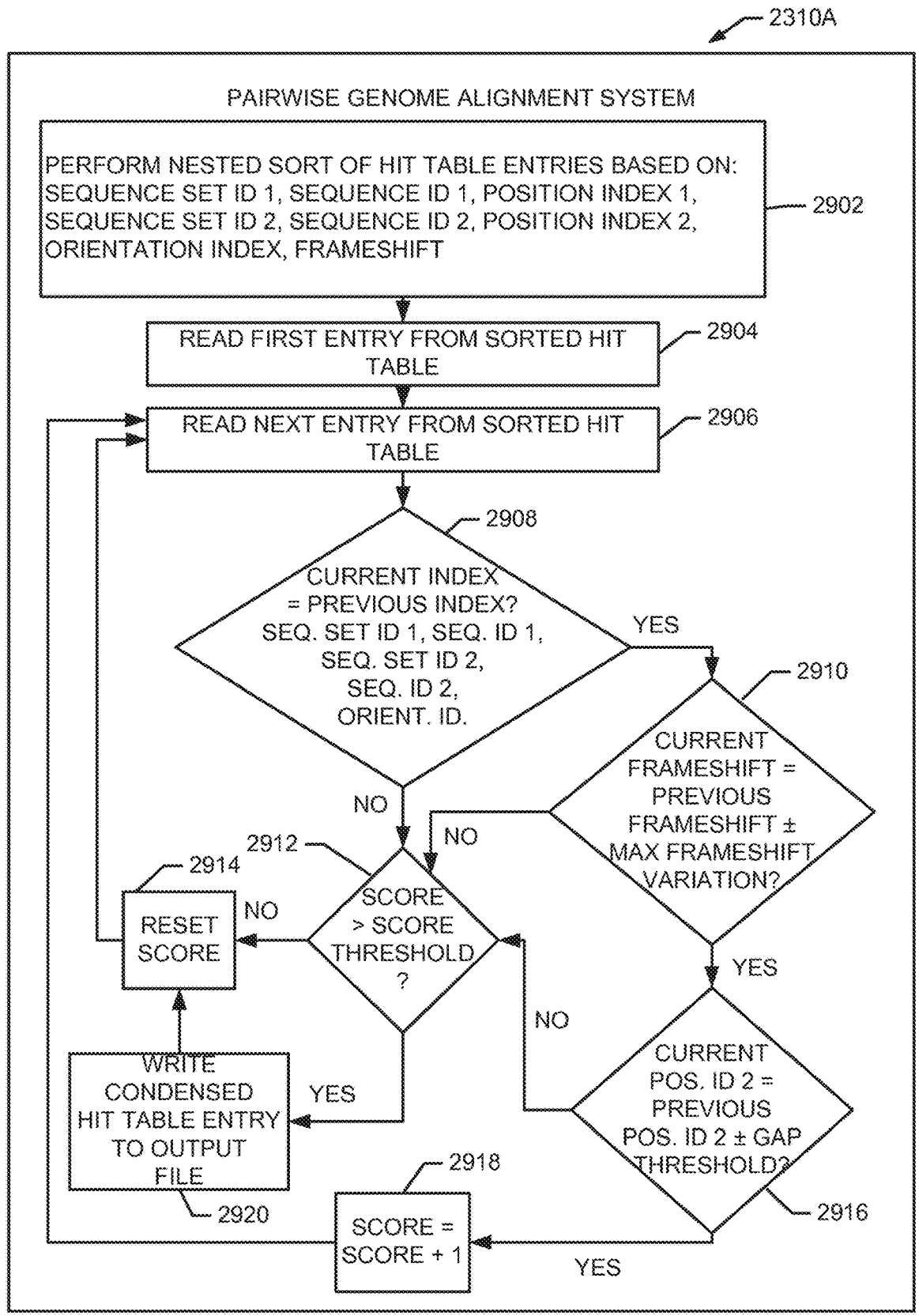
FIG. 29 is a block diagram of a pairwise genome alignment post processing system in accordance with an embodiment of the present invention.

FIG. 29 is an illustration of an exemplary pairwise genome alignment system 2310A. In one example, the layout generation system 104 is modified by using a different hit table condensing system 236. In another example, shown in FIG. 29, the hit table condensing system 236 is not included in the layout generation system 104A, and a condensed hit table 238 is not created. The post processing system 240 instead processes a sorted hit table. The pairwise genome alignment system 2310A reads in the sorted hit table 234 and performs a nested sort of the hit table entries at step 2902. The nested sort is performed based on sequence set index 1, sequence index 1, position index 1, sequence set index 2, sequence index 2, position index 2, orientation index, and frameshift. The first hit table entry from the resorted hit table entry is then read at step 2904. Another hit table entry is read at step 2906 and a subset of the current hit table entry's indices IS compared with the corresponding indices of the previous hit table entry at step 2908. The subset of indices from the sorted hit table entries include sequence set index 1, sequence index 1, sequence set index 2, sequence index 2, orientation index, and frameshift. If all of the subset of indices matches in step 2908, then the frameshift from the current hit table entry is compared to the previous frameshift at step 2910. If the subset of indices of the current and previous hit table entries does not match at step 2908, then the current score is compared to a score threshold at step 2912.

If the current frameshift falls within the maximum frameshift variation at step 2910, the current position index 2 is compared with the previous position index 2 at step 2916. If the current frameshift does not fall within the maximum frameshift variation at step 2910, the current score is compared to a score threshold at step 2912. For example, the maximum frameshift variation is the amount of allowable variation in the frameshifts of two consecutive hit table entries due to minor variations in the sequences being compared. In an embodiment, the maximum frameshift variation may range between 0 and about 10% of the length of the sequences being compared. In another embodiment, the maximum frameshift variation may range between 0 and about 1000 nucleotides.

If the current position index 2 falls within the gap threshold at step 2916, then the score, which specifies the number of duplicate hit table entries, is increased by one at step 2918, and the next sorted hit table entry is read at step 2906. If the current position index 2 falls outside the gap threshold at step 2916, then the current score is compared to a score threshold at step 2912.

The gap threshold is a maximum allowable separation distance between two consecutive hits within a sequence from sequence set 2 in one condensed hit table entry. In one embodiment, the gap threshold may vary from 0 to about 10% of the length of the sequence from sequence set 2. In another embodiment, the gap threshold may vary from 0 to about 1000 nucleotides.

The score threshold specifies a minimum number of matches that a sequence from sequence set 1 must have with a sequence from sequence set 2 to be included as a condensed hit table entry. In one embodiment, the score threshold may range between 0 and about 100,000 matches.

If the current score is greater than a score threshold at step 2912, then the current hit table entry and current score are used to generate a condensed hit table entry, which is written to the output file at step 2920. The condensed hit table entry includes all of the indices of the current hit table entry, plus the score, which specifies the number of duplicate entries for the hit table entry. After the condensed hit table entry is written to the output file, the score is reset to zero at step 2914. If the current score is less than the score threshold, then the score is reset to zero at step 2914, no condensed hit table entry is written to the output file for the current hit table entry, and the next hit table entry is read from the resorted hit table at step 2906.

The output file generated by the pairwise genome alignment system 2310A is a condensed hit table with a small amount of tolerance introduced to the assessment of matching frameshift and a minimum score requirement for the inclusion of all condensed hit table entries. The condensed hit table specifies the regions of homology between the genome contained in the first sequence set and the genome contained in the second sequence set.

LUT-Based Layout Generation System

Various aspects of the layout generation system 104 described previously utilize the comparison of lists of mers and associated information that are resident on nonvolatile media such as a computer hard disk to match the nucleotide sequences of one or more sequence sets. To reduce processing time, the lists of mers may be sorted in order to organize the mers such that small subsets of the mer lists may be systematically compared and matched using relatively modest processor capacity.

In another aspect, a list of mers may be compared to the entries of a lookup table (LUT), which may be stored on volatile memory such as processor memory. The storage of mers in a LUT may be especially advantageous for storing comparing mers generated using a comparing sequence set for repeated use in a templated sequence assembly system, quantitative sequence assembly system, or pairwise genome alignment system. The use of a LUT allows nearly constant time access to information about any comparing mer stored in the LUT, without need to access or manipulate any of the comparing sequence sets or comparing mer tables. In one aspect, the LUT is substantially similar to the LUTs described in U.S. Pat. No. 6,223,128, which is hereby incorporated by reference in its entirety.

Figure 30:
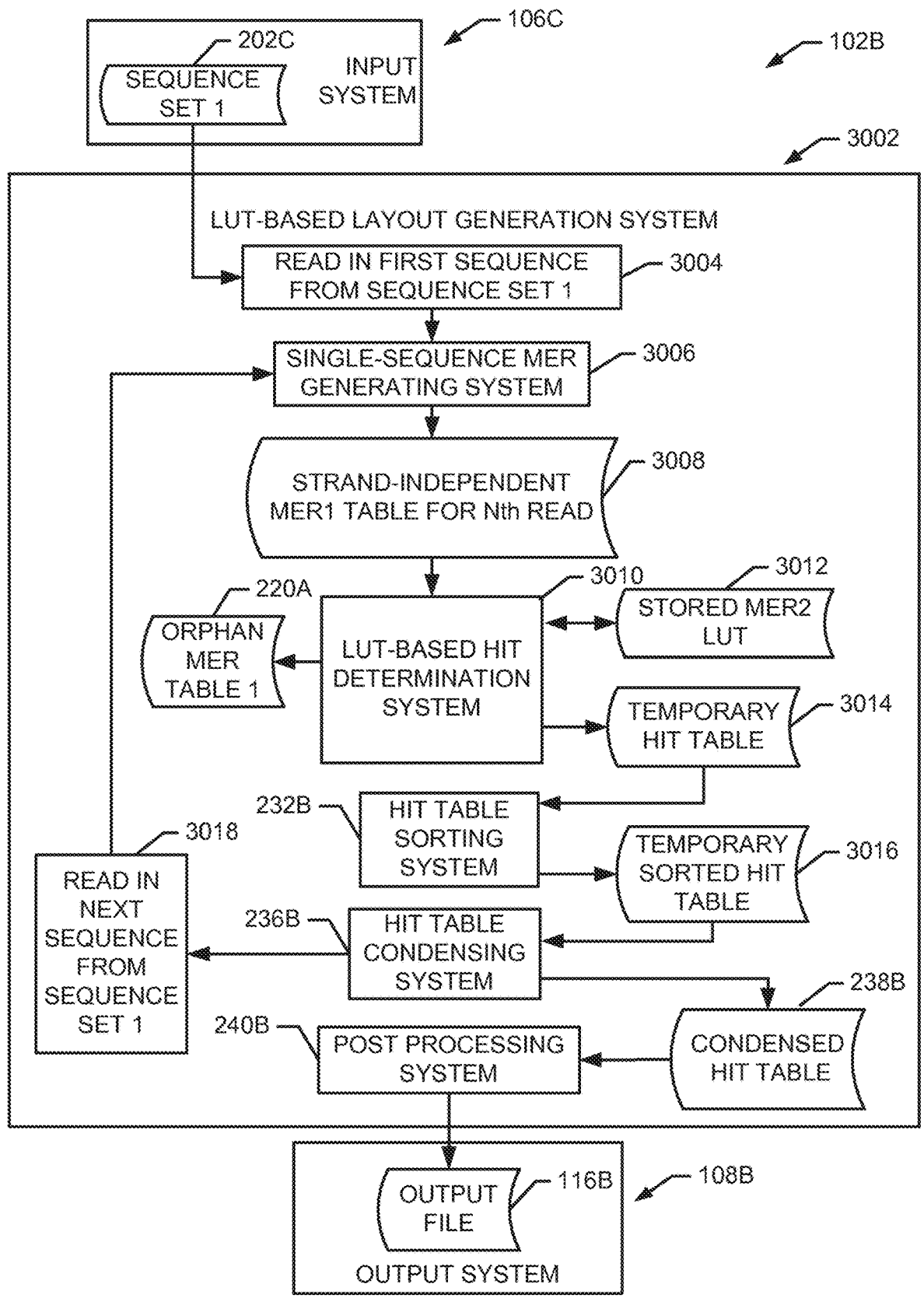
FIG. 30 is a block diagram of a lookup table-based layout generation system in accordance with an embodiment of the present invention.

FIG. 30 is a block diagram of an exemplary LUT-based layout generation system 102B for automatically assembling a nucleotide sequence, such as a genome, using a lookup table (LUT) that is stored in volatile processor memory to provide the comparing mers that are matched against the read mers during the operation of the system. The layout assembly system 102B includes an input system 106C that stores at least one sequence set 1 202C (read sequence set) in nonvolatile memory. The layout assembly system 102B also includes a LUT-based layout generation system 3002 that generates a plurality of mer1s from each sequence in the sequence set 1 202C, matches the mer1s (read mers) by locating matching mer2s (comparing mers) in a lookup table (LUT) stored in volatile processor memory, and processing the resulting hits in a manner that is substantially similar to the methods described in FIG. 2.

A particular advantage of the inclusion of a LUT to provide comparing mer sequences and associated location data is that the LUT-based layout generation system is capable of processing a subset of the total mer1s generated from the sequence set 1 202C. In this particular aspect, the LUT-based layout generation system 3002 may process the sequences from the sequence set 1 202C one sequence at a time. Because the time taken to access matching comparing mer2s is essentially independent of the order in which the mer1s are presented for matching, there is no need to assemble or sort the mer1s generated from the sequence set 1 202C to minimize processing time.

The LUT-based layout generation system 102B reads a single sequence from the sequence set 1 202C at step 3004 into a single-sequence mer generating system 3002 that is substantially similar to the mer generating and sorting system 208 previously described in FIG. 2 and FIG. 4. The single-sequence mer generating system 3002, however, processes each sequence of the sequence set 202C individually and records the resulting mers and associated data, such as the sequence index 308, position index 624, strand index 626, and sequence set index 323 (see FIG. 6), in a strand-independent mer1 table 3004 that contains only the mer1s generated from the single sequence 1.

The LUT-based layout generation system 3002 further includes a LUT-based hit determination system 3006 that matches each mer1 in the strand-independent mer1 table 3004 to the corresponding mer2s provided by the stored mer2 LUT 3012. Any matches between the mer1s and the mer2s are recorded as one or more entries in a temporary hit table 3014, which is essentially the same as the hit table 218 described previously in FIG. 2 and FIG. 18, except that the temporary hit table contains only entries associated with the mer1s generated from a single sequence 1 at any given time. Any mer1s that do not match any mer2s in the stored mer2 LUT 2012 are written to an orphan mer table 220A that is essentially the same as the orphan mer table 1 220 previously described in FIG. 2. Once the mer1s from the entries of the strand-independent mer1 table 3004 have been processed by the LUT-based hit determination system 3006, the entries of the table 3008 are deleted. Each unmatched mer1 entry is recorded in an orphan mer table 1 220A.

The temporary hit table 3014 is processed using the methods previously described and illustrated in FIG. 2. A hit table sorting system 232B, previously described in FIG. 19, sorts the entries of the temporary hit table 3014 to create groups of entries with the same sequence index 2, and subgroups of entries having the samesequence index 1 within each sequence index 2 group. The rearranged hit table entries are stored in a temporary sorted hit table 3016, previously described in FIG. 20. The entries of the temporary sorted hit table 3016 are processed by a hit table condensing system 236B, described previously in FIG. 21, to combine repeated hit table entries into a single entry with a repeat count to record the number of occurrences of a match between a particular mer1 and a particular mer2.

Once all entries of the temporary hit table 3014 have been sorted, the entries may be deleted. Similarly, once all entries of the temporary sorted hit table 3016 have been condensed, the entries may be deleted. Because all intermediate table entries are deleted once they have been processed, the LUT-based layout generation system 3002 incurs relatively less computational overhead such as nonvolatile storage space and volatile processor memory capacity compared to the disk-based assembly method. Once all of the sequences of the sequence set 1 202C have been processed into mer1s, matched and recorded into the condensed hit table 238B, a post processing system 240B further processes the data using methods substantially similar to those describes previously in FIGS. 23-29, resulting in an output file 116B.

Other aspects of the invention may process two or more sequences from the sequence set 1 202C at a time. In yet another aspect, all sequences from the sequence set 1 202C may be processed at the same time by the LUT-based layout generation system 3002. In still another aspect, the entries of the temporary tables used to store intermediate data during the processing of the sequence set 1 202C data may be deleted after the processing of a single sequence, after the processing of at least two or more sequences, or after the processing of all sequences from the sequence set 1 202C by the LUT-based layout generation system 3002. Non-limiting examples of temporary tables that may be deleted after the completion of processing include the strand-independent mer1 table 3004, the sequence set 1 202C, the temporary hit table 3014, the temporary sorted hit table 3016, and combinations thereof. A more detailed description of the systems and methods used by the LUT-based hit determination system 3006 is provided below.

Stored Mer2 LUT

In one aspect, the stored mer2 LUT 3012 may be arranged in a hash table format in which a hash key is used to index the hash table entries. The hash key may be encoded in the form of a prefix that includes the first $k_h$ bases of each mer sequence in the LUT where $k_h$ is typically less than the total number of bases in a mer nucleotide sequence. In one aspect, $k_h$ may range from about 8 to about 12 bases. The hash key may be encoded using a 2-bit representation of each base in the prefix combined into a single integer value.

During the creation of the hash table, a hash table chain or bucket is created for each possible hash key, and zero or more actual mers are stored in the hash table chain. All bases of the mer nucleotide sequences are stored along with associated data within the chain. Non-limiting examples of associated data includes a count of the number of occurrences of each mer in a sequence set, a sequence identifier for each mer occurrence, a position of the mer within a sequence for each mer occurrence, and a strand direction (i.e. forward-directed or reverse-directed) for each mer occurrence. Initially, the hash table chain may be a linear list of the mers kept in sorted order by their suffixes. However, to preserve the constant-time lookups of the hash table and efficiency of building the hash table for very large chains, large lists may be replaced by a nested tree of recursive mer prefix hashes as the number of table entries grows.

Typical uses of the stored mer2 LUT 3012 are to store a count of the number of occurrences of each mer present in a set of sequences or to store the count with additional positional information, such as the sequence identifier, position, and strand of each occurrence of the mers.

When the positional information for each mer2 is stored in the entries of the stored mer2 LUT 3012, sequence mapping may be performed directly from the LUT 3012. Any mer1 may be mapped to the genome by directly looking up the mer1 sequences in the stored mer2 LUT 3012/e. The combinations of a mer1 sequence and the possible matched positions on sequence set 2 (comparing sequence set) form the hits for that mer1. This information is essentially the same as the information contained in the entries of a hit table 218 sorted by sequence index 1 (see FIG. 20) and is typically resident on a nonvolatile storage device such as a hard disk. Using the in-memory lookup table has the advantage that each read's set of hits can be immediately processed and discarded leaving only the result information for each mer1, avoiding the costly storage of vast numbers of per-mer hit records.

In rare cases where K, the number of nucleotides in the mer nucleotide sequence is relatively small, a more direct approach to hash table structure may be used. Instead of using a mer prefix as a hash, the entire mer may be used as the initial lookup. This hash table structure represents a special case conceptually in which $K_h$=K. In this case, a simple array of these hashes may be used in the hash table structure, allowing significantly lower search times to access the mer2 data.

In one aspect, the mer length used for the entries of the LUT may range from about 5 to about 33 bases. In an exemplary aspect, the mer length used for each entry of the LUT may be at least about 15 or 17 nucleotides for quantitative sequencing assembly applications. In another exemplary aspect, the mer length used for each entry of the LUT may be less than about 13 bases for positional applications such as templated assembly and templated genome alignment.

Single-Sequence Mer Generating System

Figure 31:
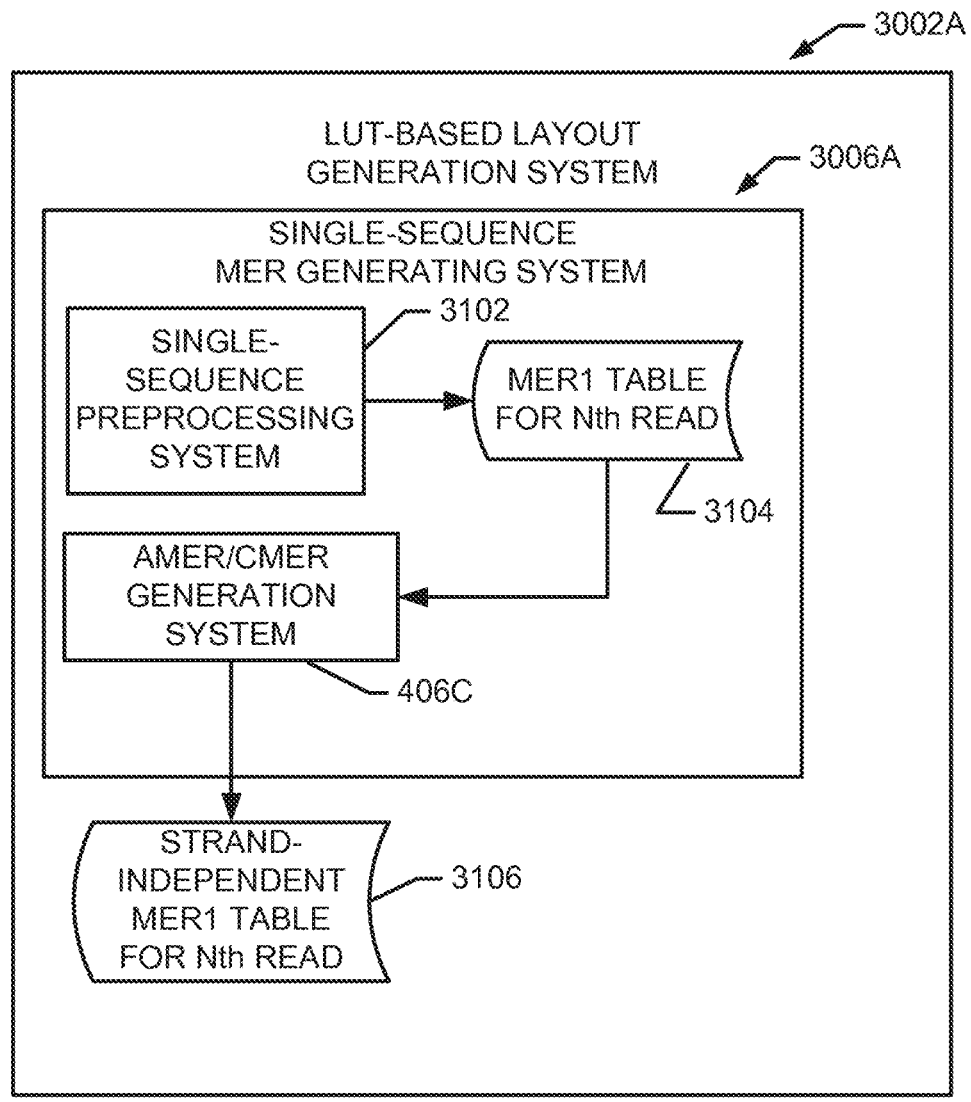
FIG. 31 is a block diagram of a single-sequence mer generating system in accordance with an embodiment of the present invention.

In an aspect, the single-sequence mer generating system 3006 generates a set of mer1s from a single sequence from a sequence table 1 202, assigns positional information to document the position of each mer within the sequence, removes the effect of sequence strand direction, and records the mer nucleotide sequence and positional information in a strand-independent mer1 table 3106. FIG. 31 is a block diagram of the single-sequence mer generating system 3006A. The single-sequence mer generating system 3006A includes a single-sequence preprocessing system 3102 that generates the mer1 set for a single sequence and stores each mer1 and its associated positional information as an entry in a mer1 table 3104. Also included in the single-sequence preprocessing system 3102 is an amer/cmer generation system 406C that provides a standardized means of comparison of mers by removing the effect of the sequence strand direction from the mer1 table entries. The resulting mer table entries are stored in the strand-independent mer1 table 3106 for subsequent processing by the LUT-based hit determination system 3010.

Figure 32:
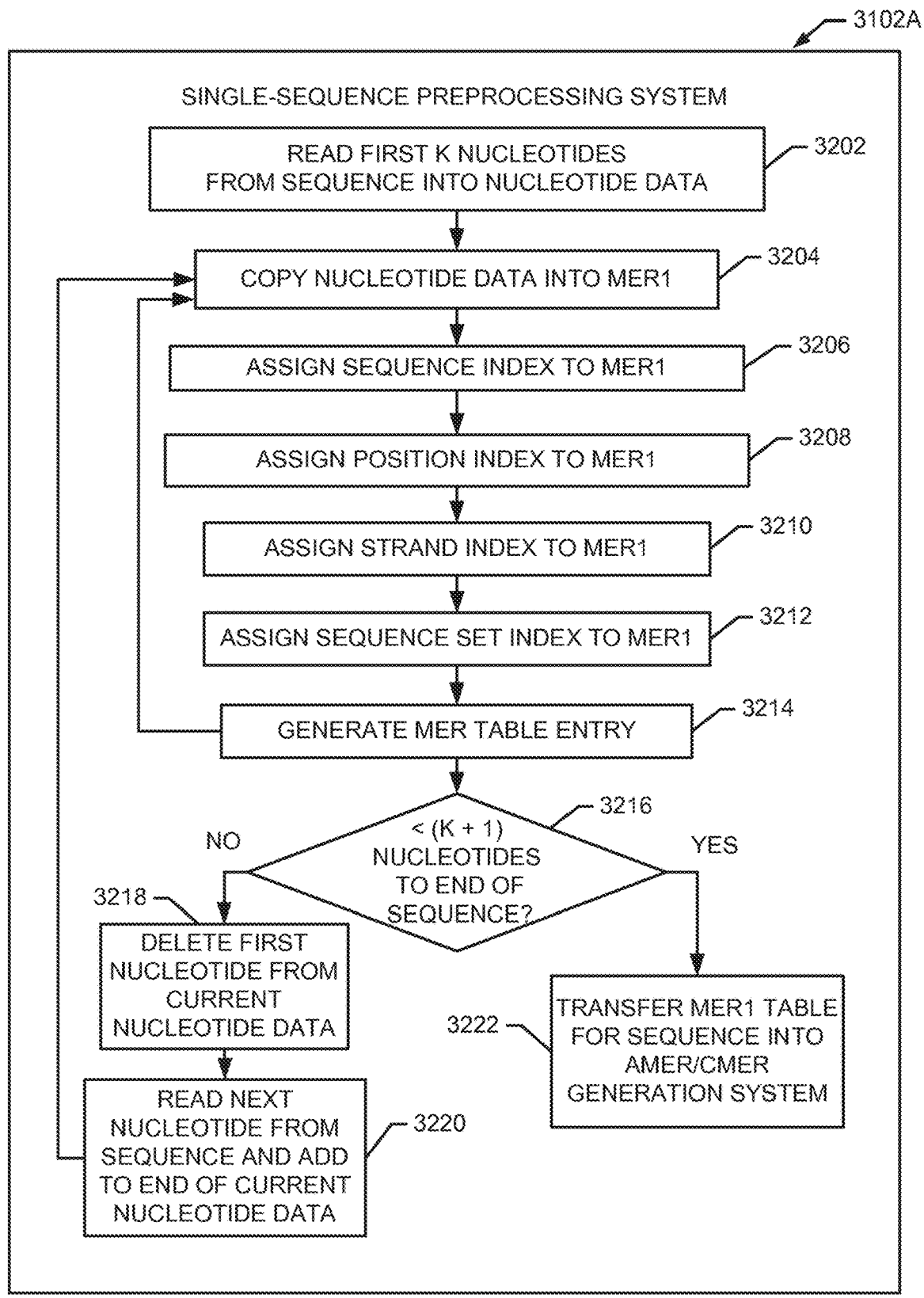
FIG. 32 is a block diagram of a single-sequence preprocessing system in accordance with an embodiment of the present invention.

The single-sequence preprocessing system 3102A, illustrated in FIG. 32, is substantially similar to the sequence preprocessing system 402 described previously in FIG. 4 and FIG. 5A. The first k nucleotides of the sequence are read in step 3202 and copied into mer1, the first element of the mer table entry, at step 3204. A sequence index documenting the particular sequence from which the mer was generated is assigned to the mer1 at step 3206. A position index documenting the location of the mer1 relative to the first nucleotide of the sequence is assigned to the mer1 at step 3208. A strand index documenting the direction of the nucleotide strand of the sequence (forward-directed or reverse-directed) is assigned to the mer1 at step 3210. The sequence set index documenting the sequence table containing the sequence from which the mer1 was generated is assigned to the mer1 at step 3212, and the mer1 and all assigned information are combined to generate a mer table entry at step 3214.

The sequence is checked to determine whether a sufficient number of nucleotides remain in the sequence to generate another mer1 at step 3216. If another mer1 can be generated from the sequence, the first nucleotide is deleted from the current nucleotide data register at step 3218, the next nucleotide in the sequence is read and added to the end of the nucleotide data register at step 3220, and the process of copying the nucleotide data into another mer1 and generating another mer table entry is repeated. If no other mer1s may be generated from the sequence at step 3216, the mer1 table entries are transferred to the amer/cmer generation system 406C at step 3222. The amer/cmer generation system 406C removes the effects of strand direction using the methods described in FIG. 8 and FIG. 9. The resulting strand-independent mer1 table is passed to the LUT-based hit determination system 3010 as shown in FIG. 30.

LUT-Based Hit Determination System

Figure 33:
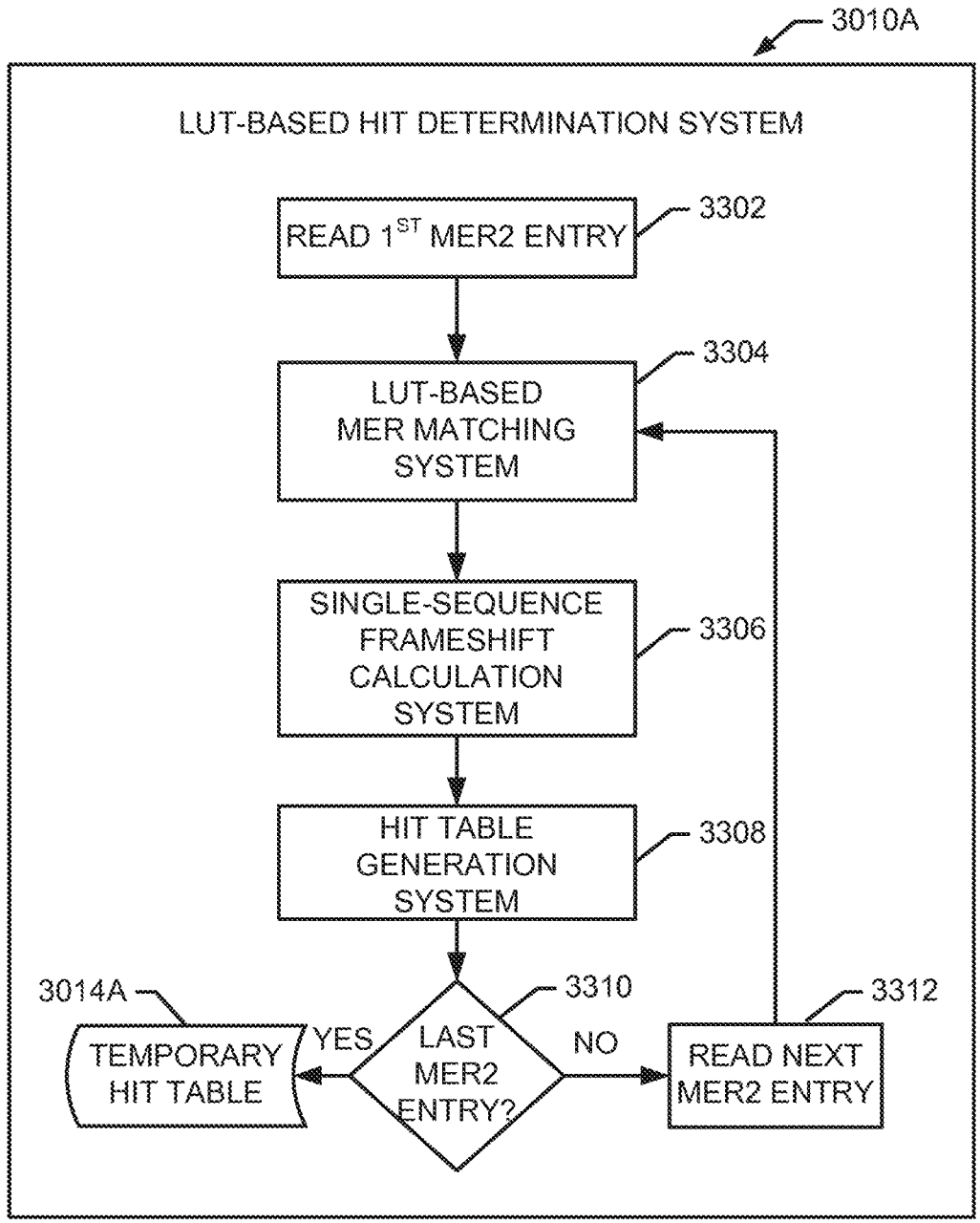
FIG. 33 is a block diagram of a lookup table-based hit determination system in accordance with an embodiment of the present invention.

The LUT-based hit determination system 3010A, illustrated in FIG. 33, compares each entry of the strand-independent mer1 table 3008 to the mer2s stored in the stored mer2 LUT 3012 and records the match as a hit table entry. The first mer1 is read from the strand-independent mer1 table 3008 at step 3302 and processed by the LUT-based mer matching system 3304, which looks up matching mer2s in the stored mer2 LUT 3012. The mer1 and any matching mer2s are then processed by the single-sequence frameshift calculation system 3306, which determines the position of the sequence used to generate the mer1 relative to the comparing sequence used to generate the mer2s for each matched pair. The hit table generation system 3308 then assembles the information describing the mer1-mer2 match including but not limited to a sequence set index 2 that identifies the sequence in the sequence set 2 204 from which the mer2s were generated, a sequence index 1 that identifies the sequence in the sequence set 1 202 from which the mer1 was generated, a position index 2 describing the location of the mer2 on its sequence, a position index 1 describing the location of the mer1 on its sequence, a strand index 2 and a strand index 1 specifying the strand directions of the sequence from sequence set 2 204 and sequence set 1 202 respectively, an orientation index identifying whether the mer1 and mer2 were generated from sequences with the same or different strand directions, and a frameshift that describes the placement of the read sequence relative to the comparing sequence that aligns the read mer1 with the comparing mer2.

If the mer1 read at step 3302 was determined to be the last mer entry from the strand-independent mer1 table 3008 at step 3310, the temporary hit table is processed by the hit table sorting system, as shown in FIG. 30. Otherwise, the next mer2 entry is read at step 3312 and processed by the LUT-based mer matching system as before.

Figure 34:
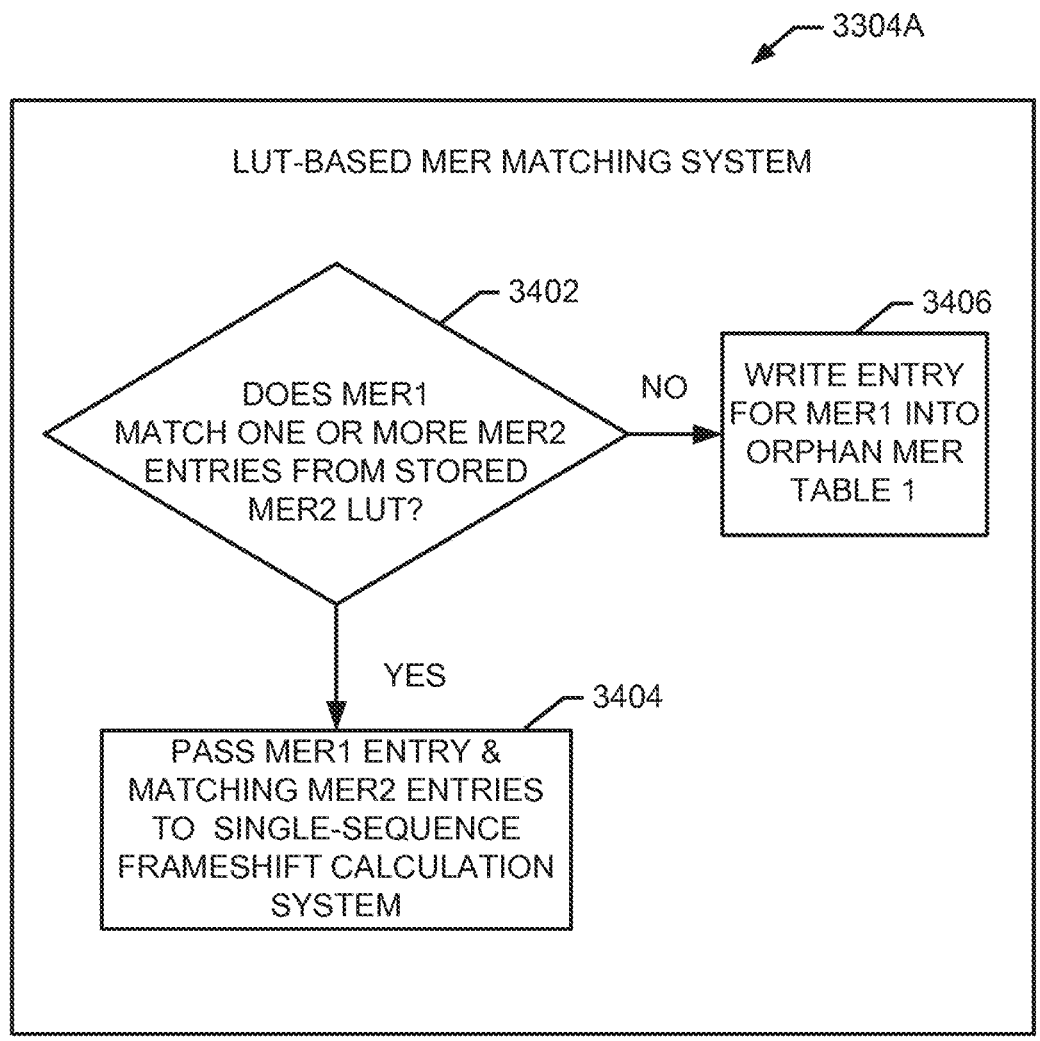
FIG. 34 is a block diagram of a lookup table-based mer matching system in accordance with an embodiment of the present invention.

An exemplary LUT-based mer matching system 3304A is illustrated in FIG. 34. A mer1 is used to query the stored mer2 LUT 3012 for any entries matching the nucleotide sequence of the mer1 in step 3402. If no matching mer2s are found, the entry from the strand-independent mer1 table 3008 is written into an orphan mer table 220A at step 3406. If one or more matching mer2s are found in the stored mer2 LUT 3012, then the mer1 table entry and any matching mer2 table entries are processed by the single-sequence frameshift calculation system 3306.

Figure 35:
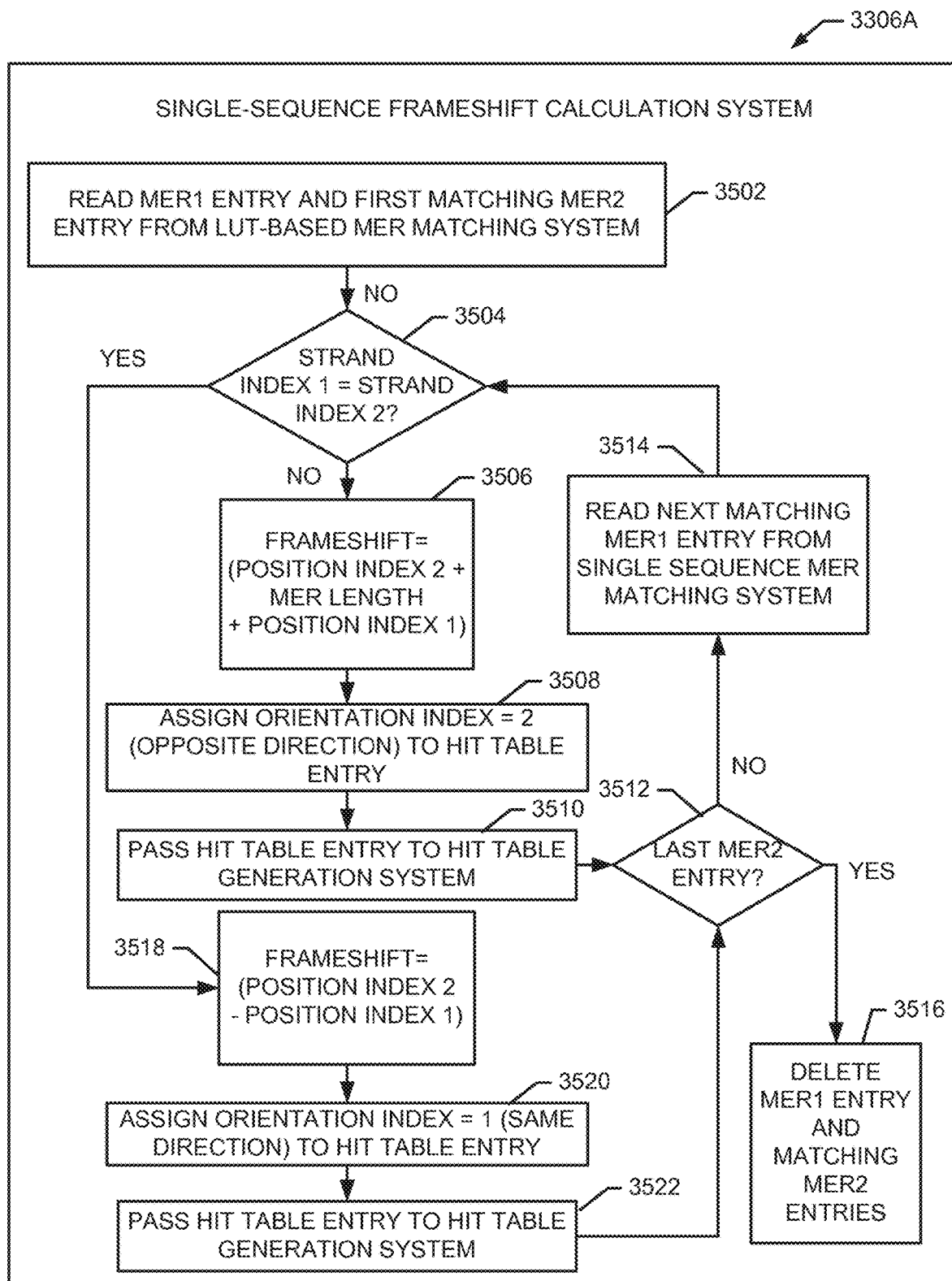
FIG. 35 is a block diagram of a single-sequence frameshift calculation system in accordance with an embodiment of the present invention.

The single-sequence frameshift calculation system 3306, illustrated in FIG. 35, is essentially the same as the frameshift calculation system 1304A described previously in FIG. 16, with modifications in order to process the matches from a single read sequence at a time, rather than the matches from all read sequences, as described previously. The mer1 table entry and any matching mer2 table entries are read at step 3502. The strand indices of each matching pair are compared at step 3504 to determine whether the matching mer2 strand has the same forward or reverse direction as the mer1 strand. If the mer1 and mer2 strands have different strand directions, this alignment is compensated for when calculating the frameshift at step 3506. An orientation index of 2 is assigned to the hit at step 3508 to specify that the mer1 and mer2 in the match were generated from sequences having opposite strand directions, and then the frameshift is calculated at step 3510. If the mer1 strand and the mer2 strand in the match have the same strand direction (i.e. both strands forward-directed or reverse directed) the frameshift is calculated at step 3518, an orientation index of 1 is assigned to the hit at step 3520, and the hit table entry is passed to the hit table generation system 3308 at step 3522. If it is determined that the mer2 entry was the last matching mer2 entry for the current mer1 at step 3512, the mer1 entry and matching mer2 entries are deleted at step 3516. If other matching mer2 entries remain to be processed, the next matching mer1 entry corresponding to the current mer1 and the next matching mer2 is read from the LUT-based mer matching system 3304A.

Hybrid Layout Generation System Overview

Figure 36:
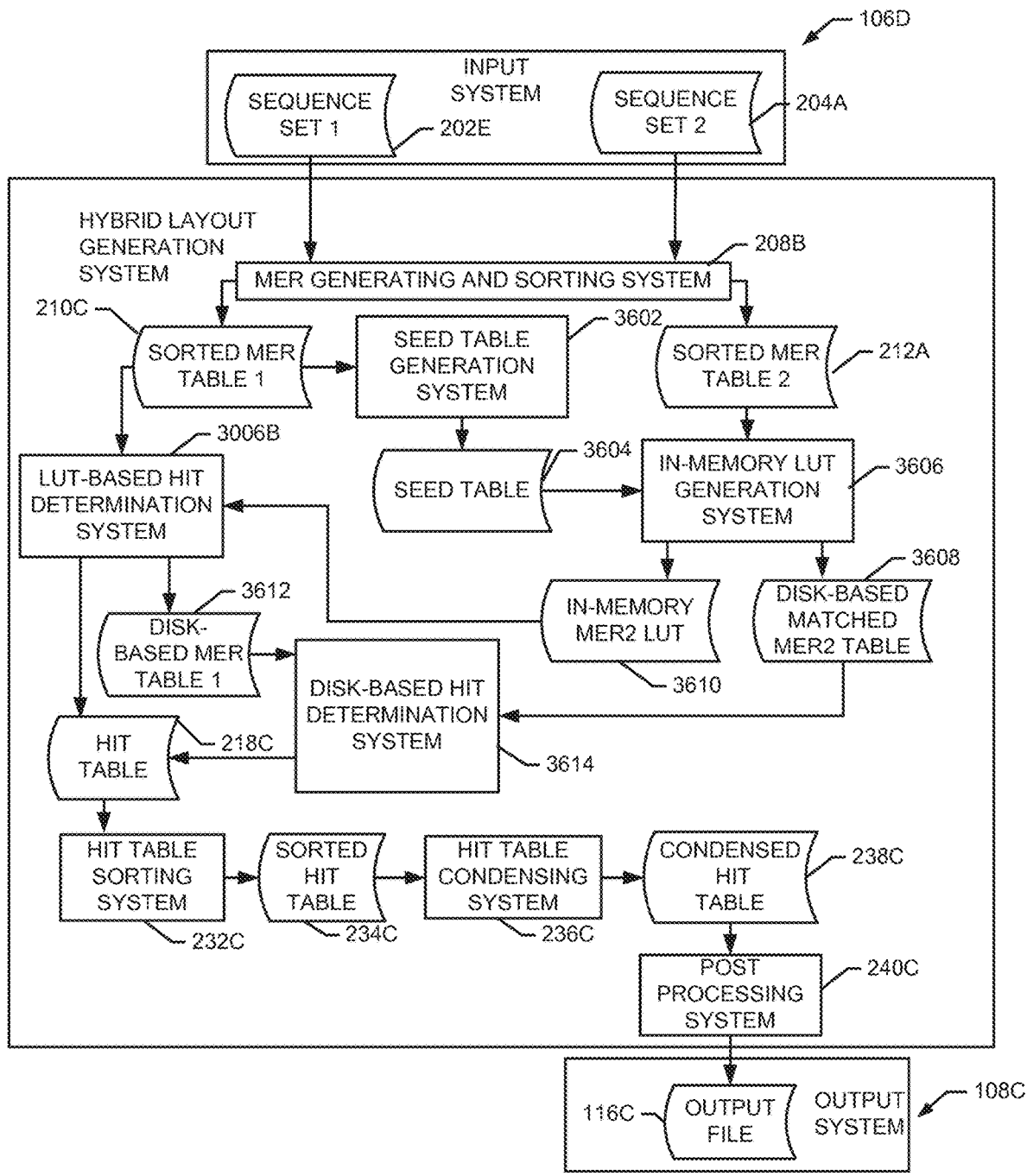
FIG. 36 is a block diagram of a hybrid layout generation system in accordance with an embodiment of the present invention.

A hybrid layout generation system 3600, described in detail in FIG. 36, combines the reduced processing times achieved using a LUT-based approach with the reduced volatile memory requirements of the disk-based approach to sequence layout generation.

The hybrid layout generation system 3600 makes use of a mer2 table that is stored in volatile memory, in a similar manner to the LUT-based layout generation system 3002. However, rather than include all mers generated from the sequence set 2 204, the in-memory mer2 LUT 3610 includes only a subset of the entire set of mer2s based on a variety of selection criteria explained in detail below.

The mer2s to be included in the in-memory mer2 LUT 3610 are a subset of the entire mer2 set that is predicted to be most frequently matched by the mer1s generated from the read sequence set 1. Because the mer2 entries in the in-memory mer2 LUT 3610 are the most likely to be frequently accessed during the mer-matching processes, the volatile memory resources of the system are allocated in a manner designed to reduce the electromechanical load on the non-volatile memory devices, such as computer disks, by reducing the number of matches to be performed using disk-based approaches. But because the disk-based approach is used to determine the hits between less frequently matched mer1s and mer2s, the volatile memory demand is reduced relative to a memory-intensive exclusively LUT-based approach. The remaining mer2 entries not selected for inclusion in the in-memory mer2 LUT 3610 are stored in a disk-based mer2 table 3608 in non-volatile memory.

During the processing of mer1 data by the hybrid layout generation system 3600, each mer1 may be quickly checked against the in-memory mer2 LUT 3610. If the matching mer2 is not found in the LUT, the mer1 table entry may be placed in a disk-based mer1 table 3612 and matched with any corresponding mer table entries from a disk-based mer2 table 3608 using the disk-based hit determination system 3614. A detailed description of the hybrid layout system 3600 is given below.

Hybrid Layout Generation System

A block diagram of an exemplary hybrid layout system 3600 is shown in FIG. 36. The hybrid layout system 3600 reads in sequences from a sequence set 1 202E (read sequence) and sequences from a sequence set 2 204A (comparing sequence) and processes them on a mer generating and sorting system 208B, yielding a sorted mer table 1 210C and a sorted mer table 2 212A. Although the sequence sets are processed to construct sorted mer tables in this exemplary aspect, in other aspects the mer tables need not be sorted. In yet other aspects, a subset of either the sequence set 1 202E or the sequence set 2 204A, or a subset of both sequences may be processed at a time, in a manner similar to that described for the LUT-based layout generation system 3002.

The mer generating and sorting system 208B is essentially identical to the mer generating and sorting system 208 previously described in FIG. 2 and FIG. 4. The sequence set 1 202E and sequence set 2 204A is used to generate the mers. The mers are further processed to remove the effect of strand direction and to sort the mers into sorted mer table entries that are organized into groups having the same mer nucleotide sequence.

In this aspect, the sorted mer table 1 210C is used to populate a seed table 3604 using a seed table generation system 3602. The seed table includes a list of seed table entries containing only a mer nucleotide sequence, and a mer count index specifying the number of times the mer nucleotide occurs within the sequence set 1 202E. The seed table is used by the in-memory LUT generation system 3606 to select the mer2 entries from the sorted mer table 2 212A for inclusion in the in-memory mer2 LUT 3610. In this aspect, the seed table contains all mer1 (read) nucleotide sequences generated from the sequences within the sequence set 1 202E. As a result, the in-memory LUT 3610 may contain only those mer2 (comparing) nucleotide sequences that have matching mer1 sequences. The remaining sorted mer table 2 entries may be either transferred to a disk-based mer2 table 3608 or deleted. In this aspect, all mer2 entries that have matching mer1 entries are included in the in-memory mer2 LUT, without regard for the number of matches for each mer2. In other aspects, some of which are described below, a subset of the mer2 table entries are selected based on other criteria that predict the number of matches with mer1 table entries based on an analysis of the sorted mer table 1 210C, sorted mer table 2 212A, or a combination of both sorted mer tables.

The in-memory mer2 LUT 3610 is interrogated by the LUT-based hit determination system 3006B to identify mer2 table entries that match mer1 table entries from the sorted mer table 1 210C and generate entries for a hit table 218C. The LUT-based hit determination system 3006B is essentially identical to the LUT-based hit determination system described previously in FIGS. 30, 33 and 34. Any mer1 entries that fail to yield a matched mer2 entry in the LUT-based hit determination system 3006B are transferred into a disk-based mer1 table 3612 and matched against the mer2 entries from the disk-based mer2 table 3608 in the disk-based hit determination system 3614. The disk-based hit determination system 3614 is essentially identical to the hit determination system 216 described previously in FIGS. 13, 14, 16, and 17. Any mer1-mer2 matches identified by the disk-based hit determination system 3614 are used to generate hit table entries, which are appended to the hit table 218C.

The resulting hit table 218C is then processed using previously described systems and techniques. In brief, a hit table sorting system 232C arranges the hit table entries such that entries are grouped by mer2 sequence, and by mer1 within each identical mer2 group, in addition to other positional and strand orientation groupings described previously in FIG. 19. The resulting sorted hit table 234C is processed by the hit table condensing system to eliminate identical hit table entries with a single hit table entry with a count index to indicate the number of repeated hit table entries, as previously described in FIG. 21. The condensed hit table 238C is further processed by a post processing system 240C that generates an output file 116C that differs in format depending on the selected analysis, including but not limited to templated assembly, de novo assembly, quantitative sequence assembly, and pairwise genome alignment.

Exemplary in-Memory LUT Generation Systems

The subset of table entries from the sorted mer table 2 212A to be included in the in-memory mer2 LUT table may be selected in order to optimize the tradeoff between the faster processing speed versus the increased demand for volatile memory inherent in the various aspects of the LUT-based method. The advantages of in-memory data processing may be best realized for repeated operations on a relatively limited amount of data. Thus, the selection of mer2 table entries that possess the highest number of matches with the mer1 table entries within sorted mer table 1 would result in more highly repeated operations (i.e. locating the mer2 LUT entries that match each mer1 entry) for a more limited amount of data. The identification of mer2 table entries that are likely to be frequently matched to corresponding mer1 table entries may be achieved using one of at least several methods described below.

Figure 37:
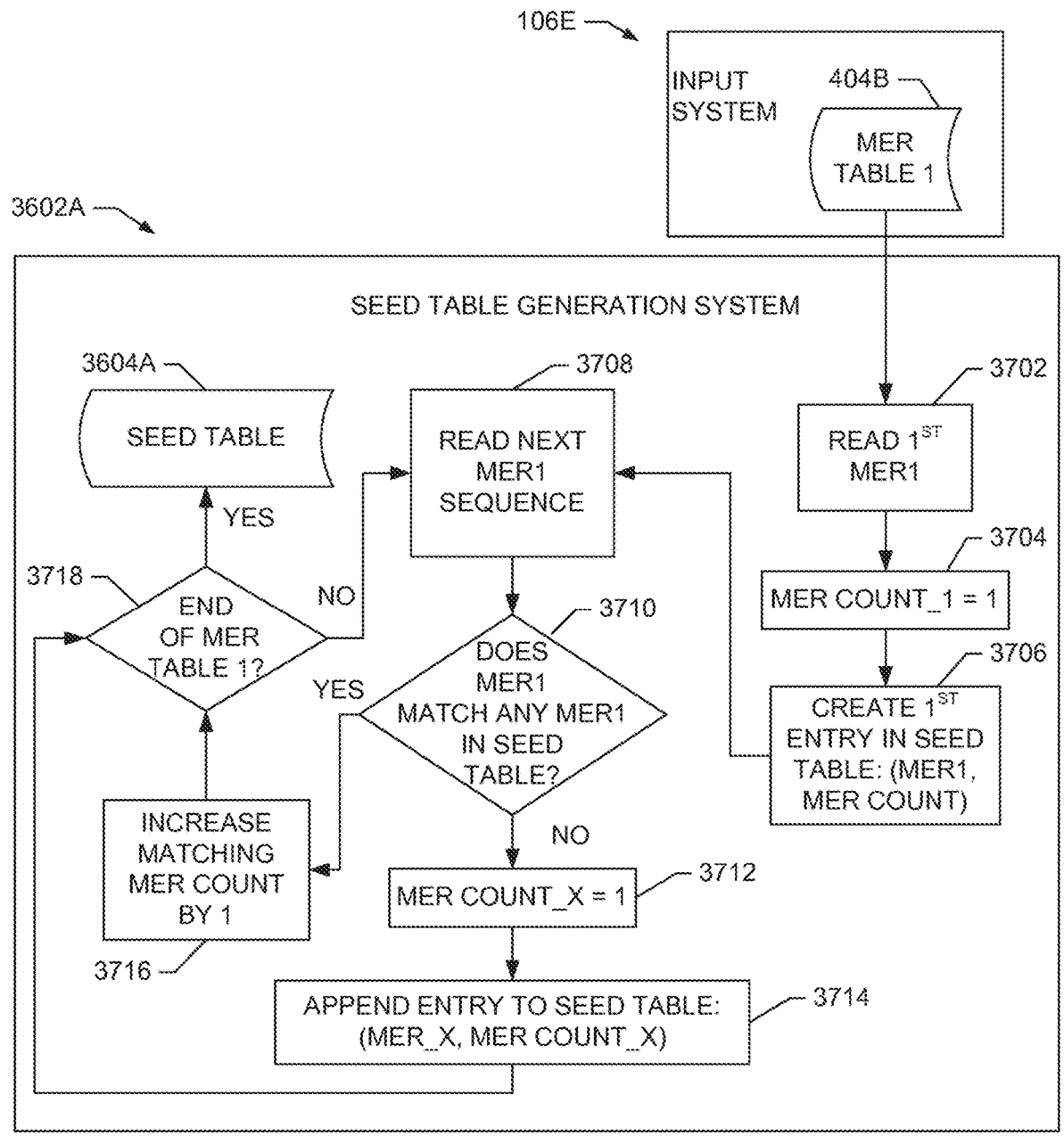
FIG. 37 is a block diagram of a seed table generation system in accordance with an embodiment of the present invention.

In one aspect, all mers from the sorted mer table 2 212A are included in the in-memory mer2 LUT 3610. In another aspect, the entries of the sorted mer table 1 210C are analyzed to determine the nucleotide sequences and frequency of occurrence of all mer1 entries in the sorted mer table 1 210C. An illustration of one aspect using this method is illustrated in FIG. 37. An exemplary seed table generation system 3602A reads the first mer nucleotide sequence of a mer table 1 404B at step 3702. At step 3704, a mercount for this mer is initially set to a value of 1. The mercount is an index indicating the number of times a given mer nucleotide sequence occurs among the entries of the mer table 1 404B. An entry in a seed table 3604 is created at step 3706 that includes the mer1 sequence and the mer count associated with the mer1.

The next mer1 sequence from the mer table 1 404B is read at step 3708 and compared to the mer1 nucleotide sequences in the seed table entries at step 3710. If the next mer1 nucleotide sequence matches a mer1 nucleotide sequence within the entries of the seed table 3604A, then the mercount of the matching seed table entry is increased by one at step 3716. If the next mer1 nucleotide sequence does not match any mer1 sequence within the seed table 3604A, then a new mercount index is set to an initial value of 1 at step 3712, and an entry to the seed table 3604 is appended to the other entries at step 3714.

At step 3718, if the end of the mer table 1 entries is not detected, the next mer1 sequence is read from the mer table 1 404B. Otherwise, the seed table 3604 is used by the in-memory LUT generation system 3606A to create the in-memory mer2 LUT used by the LUT-based hit determination system 3006B.

Figure 38:
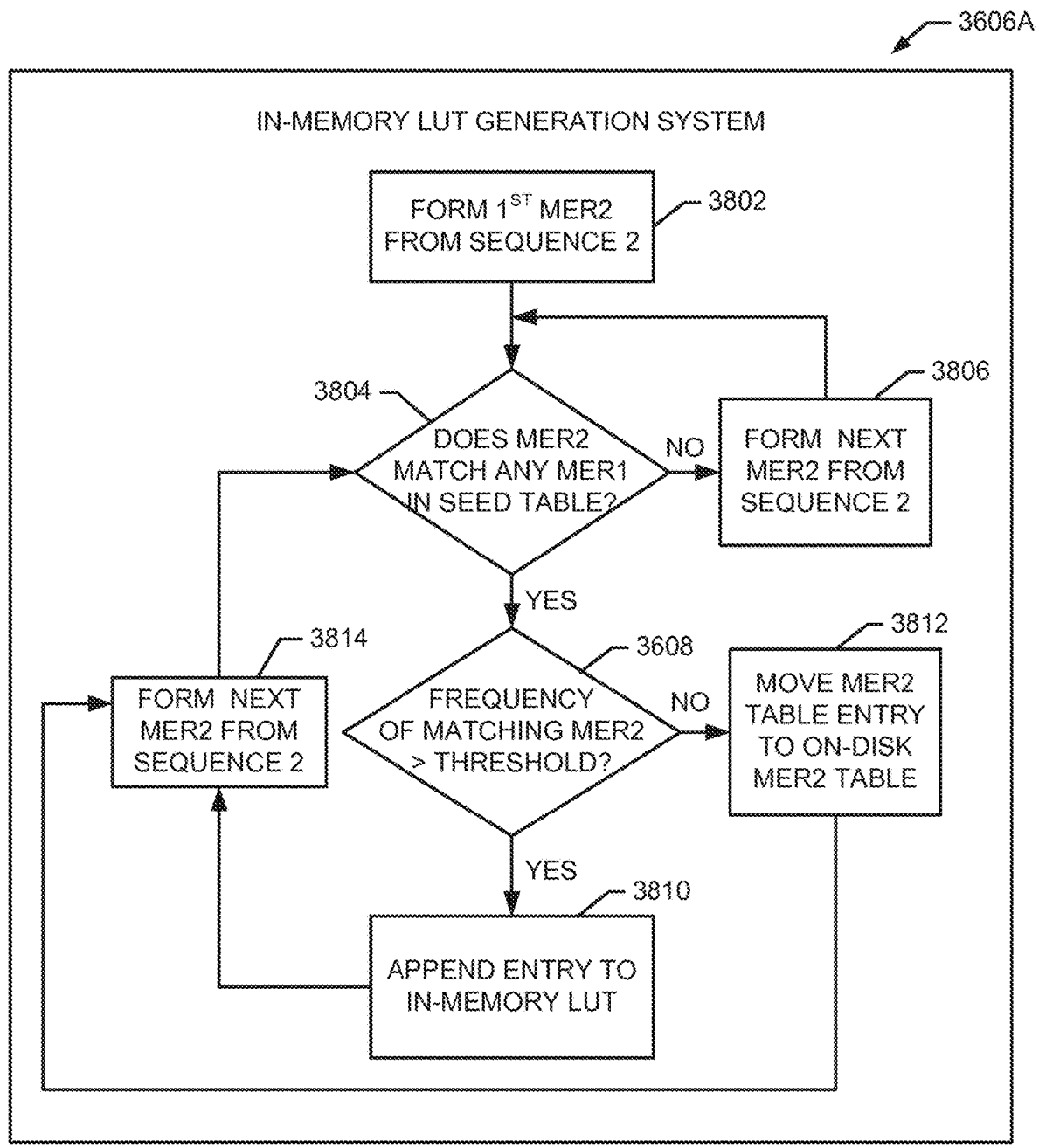
FIG. 38 is a block diagram of an in-memory lookup table generation system in accordance with an embodiment of the present invention.

An exemplary in-memory LUT generation system 3606A is illustrated in FIG. 38. In this aspect, the mer2 nucleotide sequences are assessed one at a time as they are generated by the mer generating and sorting system 208B. In other aspects, the in-memory LUT generation system may assess mer2 nucleotide sequences read from other data sources, including an unsorted mer table 404 and a sorted mer table 2 212. Referring back to FIG. 38, the first mer2 nucleotide sequence is formed from the sequence set 2 204A at step 3802, and compared to the mer1 nucleotide sequences in the seed table entries at step 3804.

If the mer2 does not match a mer1 in the seed table 3604, then the next mer2 is formed from the sequence set 2 204A at step 3806 and is similarly assessed at step 3804. If the mer2 does match a mer1 from the seed table 3604, then the mercount associated with the mer1 from the seed table 3604 is compared with a LUT inclusion threshold at step 3808.

The LUT inclusion threshold is a value corresponding to the minimum number of repeated occurrences of a mer1 nucleotide sequence that a mer2 nucleotide sequence must match in order to be included in the in-memory mer2 LUT 3610. As discussed previously, mer2 sequences that have a high number of predicted matches with the mer1 sequences take the best advantage of the fast processing speed of the LUT-based methods. However, if too many mer2 sequences are included in the in-memory mer2 LUT 3610, the volatile memory may become nearly full, leaving little excess capacity for processing data in the LUT-based hit determination system 3006B. In an aspect, the LUT inclusion threshold is set to a value selected so that no more than about 50% of the available volatile memory capacity of the system is used for storage of the in-memory mer2 LUT 3610.

At step 3808, if the frequency of occurrence of the mer1 sequence that is matched to the mer2 sequence under consideration is greater than the LUT inclusion threshold, an entry for this mer2 is appended to the in-memory mer2 LUT 3610 at step 3810, and the next mer2 is formed from the sequence set 2 204A at step 3814. If the frequency of occurrences of the matching mer1 sequence falls below the LUT inclusion threshold at step 3808, the mer2 is used to create a table entry on the disk-based mer2 table 3608.

Figure 39:
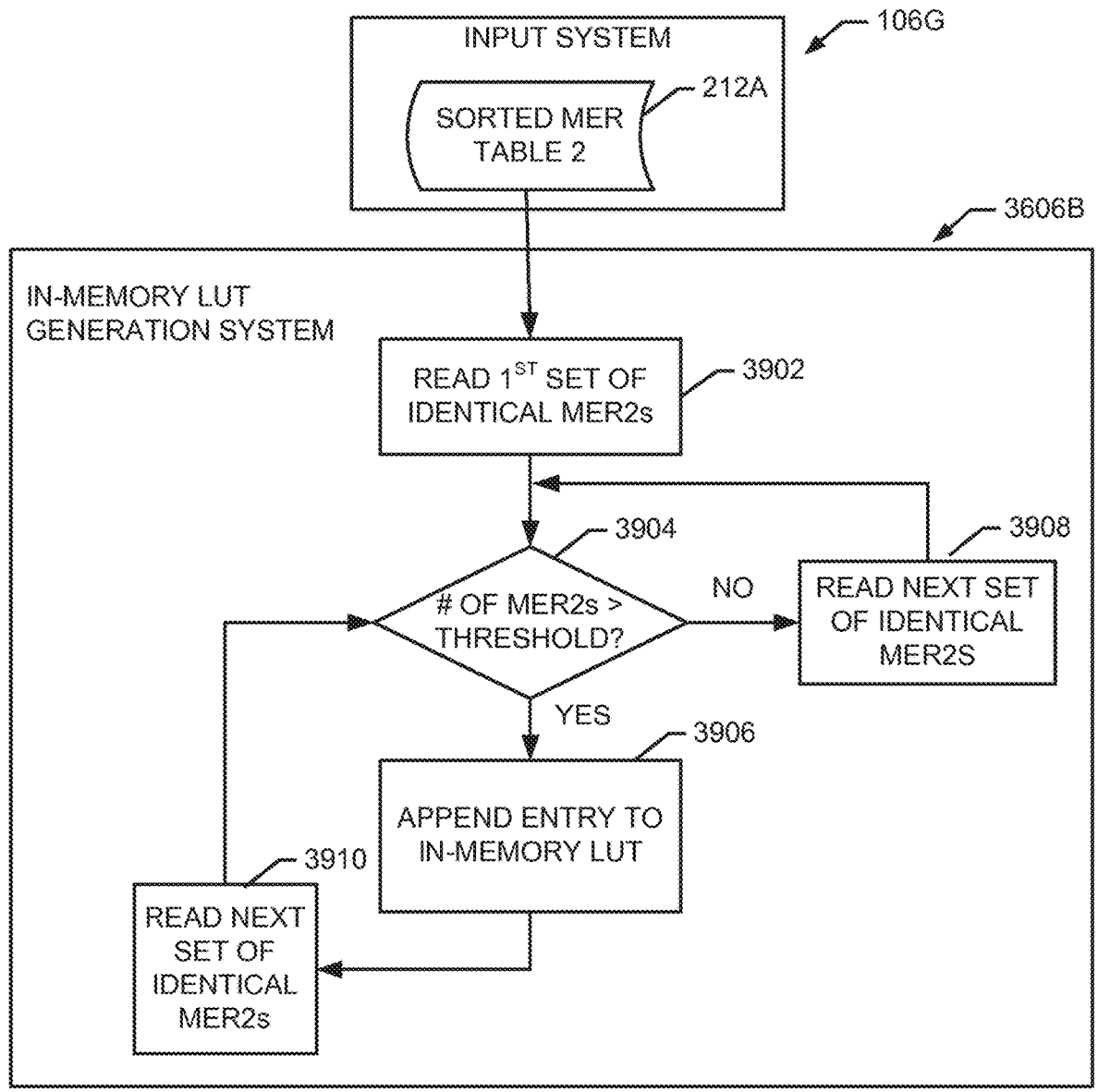
FIG. 39 is a block diagram of an in-memory lookup table generation system in accordance with another embodiment of the present invention.

In another aspect, the mer2 nucleotide sequences may be analyzed to estimate the most frequently matched mer sequences, in order to determine a criterion for including a particular mer2 sequence in the in-memory mer2 LUT 3610. In this aspect, it is assumed that a mer2 sequence that has a high frequency of occurrence would predict a relatively higher number of matches with mer1 sequences compared to less frequently occurring mer2 sequences. An exemplary in-memory LUT generation system 3606B that makes use of an analysis of the mer2 nucleotide sequences is illustrated in FIG. 39. A sorted mer table 2 212A is read to identify a first set of identical mer2 sequences at step 3902. The number of identical mer2 sequences, which is a quantity analogous to the mercount of the seed table 3604, is compared to a LUT inclusion threshold at step 3904. Similar to the previously described exemplary in-memory LUT generation system 3606A, the LUT inclusion threshold is selected such that no more than about 50% of the available volatile memory capacity of the system is used for storage of the in-memory mer2 LUT 3610. If the number of identical mer2 sequences in the group is greater than the LUT inclusion threshold, then an entry including the mer2 sequences in the group are appended to the in-memory mer2 LUT 3610 at step 3906, and the next group of identical mer2 sequences is read from the sorted mer table 2 212A at step 3912. Otherwise, the next set of identical mer2 sequences is read from the sorted mer table 2 212A at step 3908.

The number of mer1$s$ having identical nucleotide sequences or the number of mer2$s$ having identical nucleotide sequences were used as criteria for the inclusion of a particular mer2 sequence in the in-memory mer2 LUT 3610 produced by the two exemplary in-memory LUT generation systems 3606A and 3606B, respectively. In a third aspect, the number of both the mer1$s$ and the mer2$s$ having an identical mer nucleotide sequence may be used as a criterion for including the mer sequence in the in-memory mer2 LUT 3610. In particular the product of the number of mer1$s$ (N) and the number of mer2$s$ (M) having identical nucleotide sequences is used as a criterion for inclusion in the in-memory mer2 LUT 3610. The product N×M is the actual number of hits that result from the matches of the mer1$s$ and mer2$s$ having that particular nucleotide sequence.

Figure 40:
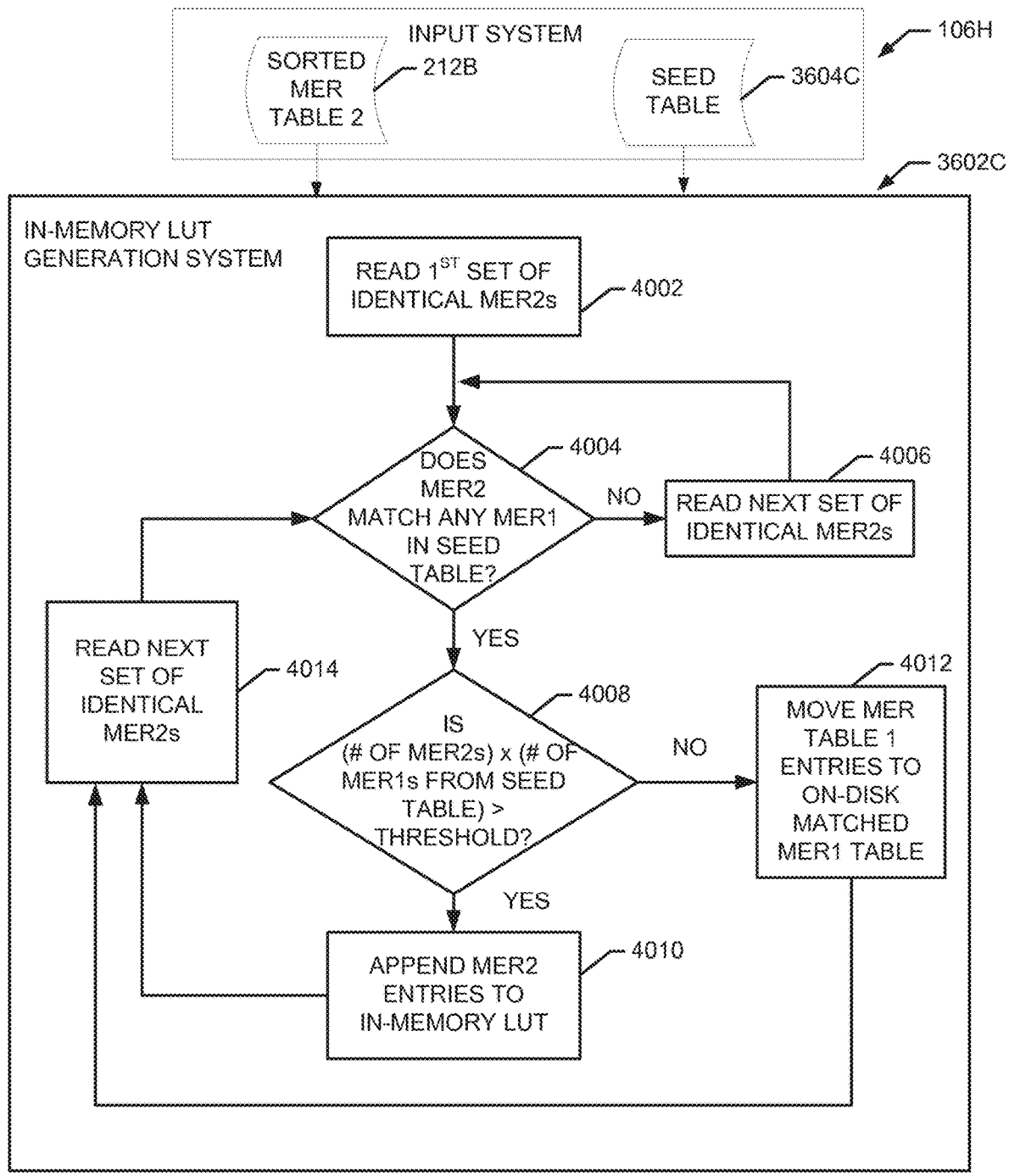
FIG. 40 is a block diagram of an in-memory lookup table generation system in accordance with yet another embodiment of the present invention.

An exemplary in-memory LUT generation system 3602C is illustrated in FIG. 40. In this aspect, a seed table 3604 and a sorted mer table 2 212B are accessed from the input system 106H and processed to select mer1 nucleotide sequences and to generate an in-memory mer2 LUT 3610. A first set of mer2 table entries having identical mer sequences are read from the sorted mer table 2 212B at step 4002. The seed table 3604C is searched to determine whether the table includes a mer1 entry having the same nucleotide sequence as the set of identical mer2$s$ at step 4004. If no matching mer1 entry is located in the seed table 3604C, then the next set of identical mer2$s$ are read at step 4002 and assessed in a similar manner at step 4004. If however, there is a matching mer1 entry in the seed table 3604C, then the number of identical mer2$s$ in the set is multiplied by the mercount (i.e. the number of occurrences of the mer1 sequence in the mers generated from the read sequences) at step 4008. Also at step 4008, the resulting product is compared to a LUT inclusion threshold, and entries of the sorted mer table 210C having the current mer1 sequence are transferred to the disk-based mer1 table 3612 for processing by the disk-based hit determination system 3614. If the resulting product is determined to be greater than the LUT inclusion threshold at step 4008, however, the set of identical mer2 table entries are appended to the in-memory mer2 LUT 3610 at step 4010, and the next set of identical mer2 table entries are read at step 4014.

In the various aspects of in-memory LUT generation systems 3602A, 3602B, and 3602C, the frequency of occurrence of repeated mer1 sequences, repeated mer2 sequences, or the product of the two frequencies of occurrence were used to estimate the amount of volatile memory to be allocated to the storage of the in-memory mer2 LUT 3610. The particular choice of in-memory LUT generation system 3602 may depend on at least several factors including the availability of mer1 and mer2 sequence data for analysis, the depth of coverage or overall length of the sequenced reads or comparing sequence, and the characteristics of the processor 112 or CRM 114 included in the layout generation system 104, such as the amount of available volatile memory capacity. In another aspect, the frequency of occurrence of mer1*s* and mer2*s* having the same mer nucleotide sequence may be used to monitor the volatile memory usage of an automated hybrid layout generation system 3600.

Automated Hybrid Layout Generation System

In one aspect, a hybrid layout generation system may be implemented in an automated manner that may be executed without need for user intervention or adjustment. In order to provide sufficient information to allocate mer matching activity between the LUT-based hit determination system 3006B and the disk-based hit determination system 3614, a combination of the three in-memory LUT generation systems 3602A, 3602B and 3602C may be utilized. Initially a seed table 3604 may be generated using a method similar to that illustrated in FIG. 37. A provisional initial LUT table inclusion threshold may be specified based on heuristics. In an aspect, the initial LUT table inclusion is set to a value that maintains volatile memory usage below a desired limit, such as about 30% of available volatile memory capacity.

An initial in-memory mer2 LUT 3610 may be generated using a method similar to that described for the in-memory LUT generation system 3606A illustrated in FIG. 38. As more mer2 entries are added to the in-memory mer2 LUT 3610, the use of volatile memory is monitored. If the use of volatile memory for storage of the in-memory mer2 LUT 3610 grows beyond a threshold storage limit, such as about 50% of the available volatile memory capacity, no further mer2 entries are added to the in-memory mer2 LUT 3610, and the remaining mer2 entries are transferred to the disk-based mer2 table 3608, along with those mer2 entries that were excluded from the in-memory mer2 LUT 3610 based on the initial LUT inclusion threshold.

The remaining mer2 entries in the disk-based mer2 table 3608 may then be scanned iteratively to add additional mer2 entries to the in-memory mer2 LUT using the methods described in any one of the in-memory LUT generation systems 3602A, 3602B, and 3602C or any combination thereof. Within each of the in-memory LUT generation systems 3602A, 3602B, and 3602C, the LUT inclusion threshold value is iteratively decreased in order to allow more mer2 entries to be transferred into the in-memory mer2 LUT 3610. As before, the usage of volatile memory is monitored through the process of adding additional mer2 sequences to the in-memory mer2 LUT 3610 and the process may be halted or the LUT inclusion thresholds may be iteratively increased if the volatile memory used to store the in-memory mer2 LUT 3610 exceeds a threshold storage limit such as 50% of the available volatile storage capacity.

As the volatile memory allocated to the storage of the in-memory mer2 LUT 3610 nears the allocated memory storage limit, the entries of the seed table 3604 having the lowest mercounts may be incrementally discarded. The elimination of low mercount entries in the seed table results in the inclusion of only the mer2 sequences matching the most frequently occurring mer1*s* in the remainder of the in-memory mer2 LUT 3610. If all mer2 sequences above a LUT inclusion threshold have been included in the in-memory mer2 LUT 3610, the seed table 3604 may be discarded altogether, and the selection of subsequent mer2*s* for inclusion in the in-memory mer2 LUT 3610 may be performed using a method similar to that described in the in-memory LUT generation system 3606B, in which the frequency of the mer2 selection is based on the frequency of each mer2 in the comparing sequence. Using this process, the final in-memory mer2 LUT 3610 can grow as large as desired without interference from the seed table.

In one aspect, mer2 entries may be placed in both the disk-based mer2 table 3608 and the in-memory mer2 LUT 3610. Since the mer1 nucleotide sequences are matched against the in-memory mer2 LUT 3610 first during analysis, mer2 sequences which are included in both locations may still be excluded from the disk-based mer2 table 3608, and the corresponding hits may be generated directly using the LUT-based hit determination system 3006B.

In another aspect, the methods of the automated hybrid layout generation system may still be utilized even if the seed table was generated only partially. Because all mer2 table entries not included in the in-memory mer2 LUT 3610 are written to the disk-based mer2 table 3608, no mer2 sequences are excluded from consideration due to having no seed count. In this aspect, the in-memory LUT generation system 3602B that makes use of the frequency of occurrence of mer2 gains higher importance. The entire sorted mer table 2 212A must be placed on disk for use in the LUT-based hit determination system 3006B and for mer2 generation. The hit generation processes remain unchanged in this aspect even if the seed table was only partially generated.

Database Search Application

In another embodiment, the basic layout generation system of FIG. 2 can be used to search databases for homologous matches. If the sequence set 1 (202) is the set of query sequences (e.g., gene sequences from an organism) and the sequence set 2 (204) is a set of nucleotide sequences from a database repository, such as NCBI's non-redundant (nr) database, and the desired result is to identify the best matching entry or entries for each sequence in sequence set 1 (202) with sequence set 2 (204), then the system as outlined in FIG. 2 can be used with only minimal modification to produce the desired output. In such a database search application of the layout assembly system, the input sequences do not include a sequence set N (206). The adaptation of the basic layout generation system for use as a database search application lies within the processing of the condensed hit table (238) by the post processing system (240). Specifically, each entry from sequence set 1 (202) is allowed to match multiple sequences from sequence set 2 (204) as well as multiple locations within a given sequence in sequence set 2 (204). Every matching position meeting defined parameter thresholds entered into the post processing system (240) is preserved and recorded.

In yet another embodiment of database searching, if the sequence set 1 (202) is the set of sequence reads from an environmental sample, and the sequence set 2 (204) is a set of nucleotide sequences from a database repository, such as NCBI's non-redundant (nr) database, and the desired result is to identify the best matching entry or entries for each sequence read in sequence set 1 (202) with sequence set 2 (204) without respect to positional parameters, then processing of the condensed hit table (238) by the post processing system (240) only considers reads individually and does not consider the placement, or lack thereof, of a paired read when determining the placement(s) of the initial read. Every matching position meeting defined parameters entered into the post processing system (240) is preserved and recorded.

EXAMPLES

The following examples illustrate various aspects of the invention.

Example 1: Impact of Mer Thinning on the Templated Assembly of Genomes

To assess the impact of reducing the number of read mers using various degrees of mer thinning, the following experiments were conducted. The Illumina 36-base sequenced read set and a ~200 base 454 sequenced read set generated from isolates of the *Escherichia coli* K-12 strain, MG1655, were processed along with the MG1655 comparing sequence set using a disk-based layout generation system similar to the system illustrated in FIG. 2. In addition a 75-base Illumina data set from a W strain of *E. coli* was also tested using the MG1655 comparing sequence set.

The layout generation system was run using mer lengths of 32, 25, and 21 bases. In addition, mer minimization was performed on the read mers by skipping every $2^{nd}$, $4^{th}$, $8^{th}$, and $16^{th}$ mer generated by the system. For each data set, the layout generation system was run with no mer thinning as a control case.

The impact of mer thinning of the read mers on the performance of the layout generation system was assessed by calculating the percentage of the total read sequences that were included in the layout file produced by the layout generation system. This measure of performance assessed how many reads were excluded from the layout file due to various levels of thinning. In addition, the overall processing time was measured for different levels of read mer thinning.

In general, at least two matching mers from a given read sequence were required to include that read sequence in the layout file. Reads matching in more than one location on the comparing sequence were added to each location. A summary of the effect of mer thinning on layout generation system performance is summarized in Table 1 below:

TABLE 1

Effect of Mer Thinning on Layout Generation System Performance

| Data Set | Mer Length (nucleotides) | $N^{th}$ mer selected in thinning | Reads included in layout (% total) | Processing Time (sec) |
|---|---|---|---|---|
| Illumina | 32 | 0 | 15.65% | 21 |
| 4316000 | 32 | 2 | 18.13% | — |
| read sequences | 32 | 4 | 0.00% | — |
| 36 base pairs | 32 | 8 | 0.00% | 10 |
| per sequence | 25 | 0 | 89.87% | — |
| | 25 | 2 | 88.55% | — |
| | 25 | 4 | 85.04% | — |
| | 25 | 8 | 16.26% | — |
| Illumina | 32 | 0 | 15.65% | 21 |
| 27110730 | 32 | 0 | 69.06% | 1471 |
| read sequences | 32 | 2 | 66.64% | 651 |
| 72 base pairs | 32 | 4 | 63.08% | 369 |
| per sequence | 32 | 8 | 56.93% | 259 |
| | 25 | 0 | 77.92% | 1659 |
| | 25 | 2 | 76.19% | 849 |
| | 25 | 4 | 73.39% | 394 |
| | 25 | 8 | 67.76% | 287 |
| | 25 | 16 | 47.46% | 198 |
| | 21 | 0 | 81.38% | 2299 |
| | 21 | 2 | 80.34% | 1443 |
| | 21 | 4 | 80.34% | 592 |
| | 21 | 8 | 0.00% | 267 |
| | 21 | 16 | | — |
| 454 | 32 | 0 | 99.86% | 143 |
| 484551 read | 32 | 2 | 99.84% | 68 |
| sequences | 32 | 4 | 99.81% | 36 |
| Approx. | 32 | 8 | 99.75% | 21 |
| 200 base pairs | 32 | 16 | | — |
| per sequence | 32 | 0 | 99.86% | 143 |
| | 25 | 0 | 0.00% | — |
| | 25 | 2 | 99.91% | 79 |
| | 25 | 4 | 99.89% | 43 |
| | 25 | 8 | 99.85% | 24 |
| | 25 | 16 | 99.70% | — |
| | 21 | 0 | 99.94% | 152 |
| | 21 | 2 | 99.93% | — |
| | 21 | 4 | 99.92% | 44 |
| | 21 | 8 | 99.87% | 36 |
| | 21 | 16 | 99.75% | 19 |

For the layouts assembled using the 36-base Illumina reads, using mers with a length of 32 nucleotides resulted in the inclusion of a relatively low percentage of reads in the layout file even before thinning the mers. Because there must be at least two 32-mers that match exactly out of only three mers per read, only about 15% of the read sequences were included in the layout file with no mer thinning. When every fourth or eighth mers were used in the process, only one mer remained per read, rendering the mers from all read sequences insufficient for inclusion in the layout file. When the mer size was lowered to 25 nucleotides, nearly 90% of the reads were included in the layout file prior to mer thinning There were minor reductions when the read mers were thinned by using every fourth or eighth mer. A significant drop in the number of read sequences included in the layout file occurred when only every eighth mer was considered as there were only two mers used per read, both of which must match the comparing mer exactly for inclusion in the layout file.

When the 72 base Illumina data set was processed, the majority of reads were present in the assembly with shorter mer sizes, resulting in more qualifying reads. Overall, fewer read sequences were included in the layout files compared to the 36 base Illumina data set, largely because the Illumina 75 base data set was prepared from an *E. coli* strain that was more distantly related to the strain used to prepare the comparing sequences. Significantly, only a minor reduction in the number of reads in the layout was experienced when the data was thinned to every fourth mer. Moreover, there was a nearly linear reduction in the processing time as the data was increasingly thinned. When a fourth of the mer data was used, the layout file was processed in about a fourth of the time.

The much longer 200 base sequences of the 454 data set were even more tolerant of thinning Nearly all of the read sequences were included in the layout file regardless of the mer size or the level of mer skipping. The processing time showed a near linear improvement with respect to the amount of mer data included, in a manner similar to the 72 base Illumina data set.

To assess the sensitivity of the effects of mer thinning on the genome of a different species, a similar analysis was performed on the ~7.4× deep James Watson data set available from 454 using the NCBI Build 36 human reference sequence as a comparing sequence.

| Data Set | Mer Length (nucleotides) | $N^{th}$ mer selected in thinning | Reads included in layout (% total) | Processing Time (sec) |
|---|---|---|---|---|
| Watson 454 | 32 | 0 | — | — |
| database | 32 | 2 | 176.66% | 19,467 |
| Approx. 200 | 32 | 4 | 138.22% | 7,977 |
| base pair read | 32 | 8 | 110.80% | 3,395 |
| sequences | 32 | 12 | 102.22% | 3,264 |
|  | 32 | 16 | 97.74% | 2,809 |
|  | 25 | 0 | 276.42% | 32,079 |
|  | 25 | 2 | 206.42% | 14,616 |
|  | 25 | 4 | 146.70% | 6,780 |
|  | 25 | 8 | 110.75% | 5,127 |
|  | 25 | 12 | 101.50% | 4,745 |
|  | 25 | 16 | 97.87% | 3,397 |
|  | 21 | 0 | 350.95% | 24,591 |
|  | 21 | 2 | 228.94% | 11,663 |
|  | 21 | 4 | 149.14% | 6,823 |
|  | 21 | 8 | 110.86% | 3,748 |
|  | 21 | 12 | 101.59% | 3,106 |

For the Watson human genome data set, the percentage of reads included in the layout file appeared to be improved by mer thinning. When all or most of the read mers were used, the percentage of read sequences in the layout was greater than 100%, indicating that a significant number of read sequences had been placed in more than one location, presumably due to the numerous repeated elements in the human genome. When the read mers were thinned by using every sixteenth mer, the percentage of reads included in the layout was close to 100%. The processing time again showed a linear reduction with respect to the amount of thinning down to approximately an eighth of the data, in a manner similar to the *E. coli* results.

Example 2: Use of the Layout Assembly System as a Database Search Application In one embodiment, the layout assembly system is used as a database searching tool to rapidly determine directly from sequence reads which sequences (e.g., genes) from among a set of particular sequences of interest are present in an uncharacterized sample. As a demonstration, 17.3 million Illumina sequence reads (each 100 bases long) derived from a pathogenic shiga-toxin containing *E. coli* (STEC) strain were used as sequence set 1 (202) and 2,312 gene sequences of either known or suspected virulence factors were used as sequence set 2 (204). Processing by the layout assembly system in database search mode allowed the number of STEC sequence reads matching each entry in sequence set 2, the percent of each sequence set 2 entry containing at least one matching sequence read from sequence set 1 (the percent covered) and the number of sequence reads from sequence set 1 with a matching base at each position of the sequence set 2 entry (the depth of coverage) to be determined. The greater the percent covered and depth of coverage, the greater the evidence that the strain represented by sequence set 1 contains that particular virulence factor gene of sequence set 2. For example, 157 virulence factor genes from sequence set 2 had at least 80% of their sequence length covered to a depth of at least 50, while 106 genes had 100% of their length covered to a depth of at least 50. Among the latter, the two type 2 shiga toxin encoding genes were identified whereas the type 1 shiga toxin encoding genes had only background levels of matching reads. This use of the layout assembly system bypasses the need for lengthy genome assembly processes and in this case directly identified the presence of key genes in minutes in sequence set 2 through database matching. This example is especially important to clinical applications as type 1 and type 2 shiga-toxin containing pathogenic microbial strains have substantially different toxicity and therefore, disease pathology.

To compare how the layout assembly system performs relative to the BLAST sequence database search system, a series of benchmarking tests were conducted. First, a local version of BLAST was implemented on a standard Macintosh desktop computer (specifications as described above) using the BLAST tool kit available from NCBI. A version of the layout assembly system with the output system (108A of FIG. 2) configured to mimic BLAST output reporting was installed on the same computer. Next, the entire non-redundant (nr) sequence database from NCBI was downloaded to the computer as sequence set 2 (204) and the sorted mer table (212) of the database entries constructed. A set of up to 4,295 gene sequences (average length of about 1 kb) from *E. coli* MG1655 were used as the query sequences (BLAST) or sequence set 1 (202 of the layout assembly system) searches against the nr database. By varying the size of the query sequence/sequence set 1 between 1 and 4,295 gene sequences the relative performance of the layout assembly system as a database search tool can be directly compared with BLAST.

Figure 47:
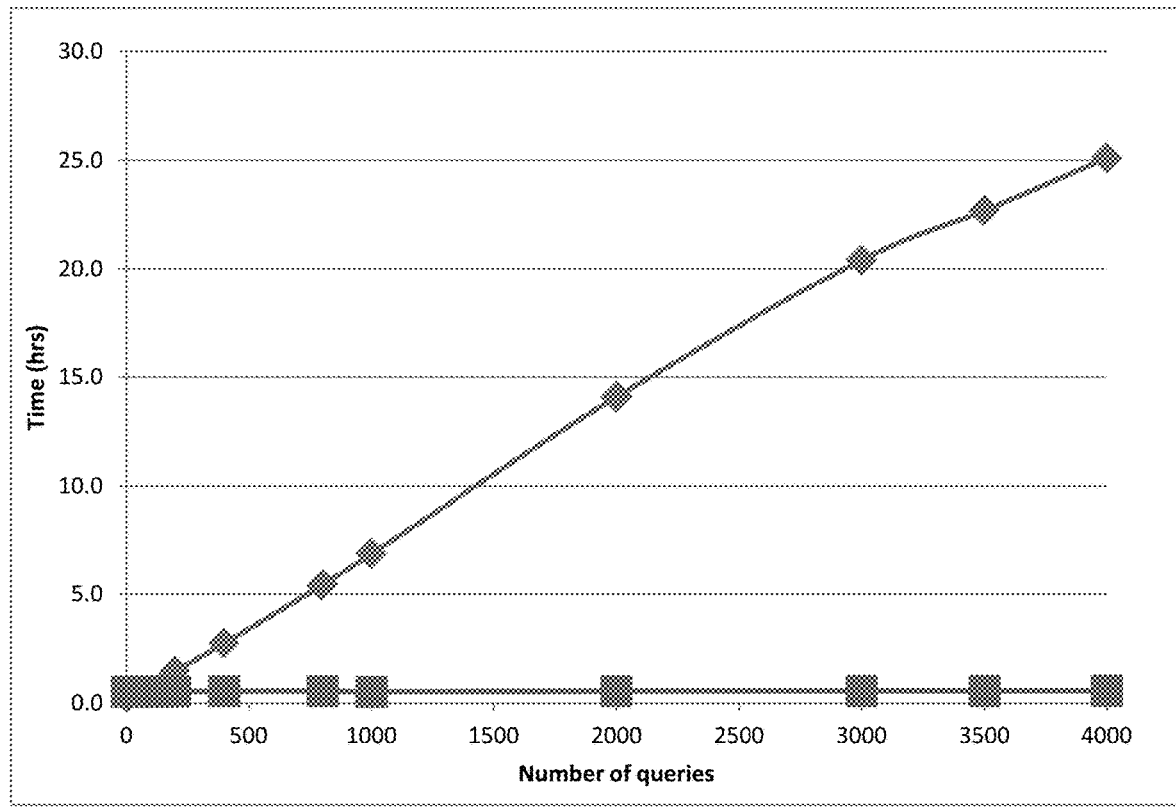
FIG. 47 depicts the relative efficiencies of BLAST and the layout assembly system as a database search tool as a function of the number of queries.

As shown in FIG. 47, the BLAST results (diamonds) exhibit a near linear increase in processing time as the number of queries grew, with an average timer per query of about 23 seconds across all tests. Because BLAST performs each query serially, this linearity is expected. In contrast, the layout assembly system (squares) is essentially independent of the number of queries taking 31 minutes to execute a single query and 34 minutes to execute 4,295 queries. This is because the layout assembly system executes all queries at once, so that traversal of the nr database mer table predominates the compute time for every query size. The breakeven point (i.e. the number of queries where the processing time is the same) for both methods is 72 in these experiments. Thus, for sequence database searches involving large numbers of queries, more than 72 in this configuration, the layout assembly system provides faster and more efficient search of large sequence databases.

The layout assembly system with the output system (108A of FIG. 2) configured to mimic BLAST output reporting produces alignment reports such as FIG. 48. The alignments present all the same information as a standard BLAST report, but under certain conditions have the advantage of speed and computational efficiency described in the proceeding paragraphs. Thus, the present invention provides a useful alternative to BLAST when query size or limited computational power restricts the functionality of BLAST.

Those skilled in the art will appreciate that variations from the specific embodiments disclosed above are contemplated by the invention. The invention should not be restricted to the above embodiments, but should be measured by the following claims.

What is claimed is:

1. A layout assembly system for identifying nucleotide sequence matches between a read sequence set and a comparing sequence set, comprising:

i) a non-transitory memory storing:

a) the read sequence set comprising a plurality of read entries, wherein each respective read entry in the plurality of read entries comprises (i) a corresponding read oligonucleotide sequence in a plurality of read oligonucleotide sequences and (ii) a corresponding read sequence index assigned to identify the corresponding read oligonucleotide sequence; and b) the comparing sequence set comprising a plurality of comparing entries, wherein each respective comparing entry in the plurality of comparing entries comprises (i) a corresponding comparing oligonucleotide sequence and (ii) a corresponding comparing sequence index assigned to identify the corresponding comparing oligonucleotide sequence, and wherein the comparing oligonucleotide sequences in the comparing sequence set collectively define a known completely predetermined comparing oligonucleotide sequence in a database of known sequences;

ii) at least one processor; and iii) at least one program stored in the non-transitory memory and executable by the at least one processor, the at least one program comprising instructions to:

divide each respective read oligonucleotide sequence in the read sequence set into one or more read mers thereby collectively forming a plurality of read mers;

assign each respective read mer in the plurality of read mers the read sequence index corresponding to a read oligonucleotide sequence from which the respective read mer was divided;

assign a read position index to each respective read mer in the plurality of read mers identifying a number of nucleotides from a location within the read oligonucleotide sequence from which the read mer was divided;

generate a read mer table comprising a plurality of read mer table entries that is stored in said non-transitory memory, each read mer table entry in the plurality of read mer table entries comprising (i) a corresponding read mer in the plurality of read mers, (ii) the read sequence index and the read position index for the corresponding read mer, wherein the plurality of read mer table entries in the read mer table are sorted by ascending or descending order of read mer sequence;

divide each respective comparing oligonucleotide sequence in the comparing sequence set into one or more comparing mers thereby collectively forming a plurality of comparing mers;

assign to each respective comparing mer in the plurality of comparing mers the comparing oligonucleotide sequence index corresponding to the comparing sequence from which the respective comparing mer was divided;

assign a comparing position index to each respective comparing mer in the plurality of comparing mers identifying a number of nucleotides from a location within the comparing oligonucleotide sequence from which the comparing mer was divided;

generate a comparing mer table comprising a plurality of comparing mer table entries, each comparing mer table entry in the plurality of comparing mer table entries comprising (i) a corresponding comparing mer in the plurality of comparing mers and (ii) the comparing sequence index and the comparing position index for the corresponding comparing mer, wherein the plurality of comparing mer table entries are sorted by ascending or descending order of comparing mer sequence;

determine, for each respective read mer in the read mer table, each match between the respective read mer and a comparing mer in the comparing mer table by comparing the sequence of the respective read mer to the sequence of a comparing mer in the comparing mer table that has not been previously been compared to a read mer in the read mer table, thereby identifying each match between comparing mers and read mers in the read mer table and the comparing mer table; and order respective read oligonucleotide sequences in the plurality of read oligonucleotide sequences with respect to each other by sorting the combination of (i) the matches between comparing mers and read mers in the comparing mer table and the read mer table, and (ii) at least one of the group consisting of sequence index, orientation index, frameshift and position index of comparing mers in the corresponding comparing oligonucleotide sequences, to form an ordered plurality of read oligonucleotide sequences that collectively identify the nucleotide sequence matches in the comparing sequence set.

2. The layout assembly system of claim 1, wherein each read mer in the plurality of read mers comprises a contiguous subset of nucleotides from one of the read oligonucleotide sequences or a subset of non-contiguous nucleotides from one of the read oligonucleotide sequences wherein the subset of non-contiguous nucleotides is selected from a read oligonucleotide sequence in the plurality of read oligonucleotide sequences by selecting every other nucleotide from all or a portion of the read oligonucleotide sequence.

3. The layout assembly system of claim 1, wherein
each comparing mer in the plurality of comparing mers is a subset of contiguous nucleotides from a comparing oligonucleotide sequence in the comparing sequence set, and
each read mer in the plurality of read mers and each comparing mer in the plurality of comparing mers is equivalent in a mer length, and wherein the mer length ranges from 2 nucleotides to about 100 nucleotides.

4. The layout assembly system of claim 1, wherein the at least one program further comprises instructions to retain every Nth read mer table entry and delete all other read mer table entries in the plurality of read mer table entries, wherein N is an integer with a value of less than the number of nucleotides in a shortest first sequence of nucleotides in the read mer table.

5. The layout assembly system of claim 1, wherein the known completely predetermined comparing oligonucleotide sequence comprises sequence reads derived from a biological sample.

6. The layout assembly system of claim 5, wherein the biological sample is a single bacterial or viral strain.

7. The layout assembly system of claim 5, wherein the biological sample is a pathogen.

8. The layout assembly system of claim 1, wherein the comparing sequence set comprises one thousand comparing entries and the read sequence set comprises fifty read entries.

9. The layout assembly system of claim 1, wherein the comparing sequence set comprises five thousand comparing entries and the read sequence set comprises one read entries.

10. A non-transitory computer readable storage medium for identifying nucleotide sequence matches between a read sequence set and a comparing sequence set, wherein the comparing oligonucleotide sequences in the comparing sequence set collectively define a known completely predetermined comparing oligonucleotide sequence in a database of known sequences, wherein the non-transitory computer readable storage medium stores instructions, which when executed by a first device, cause the first device to:

divide each respective read oligonucleotide sequence in a read sequence set into one or more read mers thereby collectively forming a plurality of read mers, wherein the read sequence set comprises a plurality of read entries, wherein each respective read entry in the plurality of read entries comprises (i) a corresponding read oligonucleotide sequence in a plurality of read oligonucleotide sequences and (ii) a corresponding read sequence index assigned to identify the corresponding read oligonucleotide sequence;

assign each respective read mer in the plurality of read mers the read sequence index corresponding to a read oligonucleotide sequence from which the respective read mer was divided;

assign a read position index to each respective read mer in the plurality of read mers identifying a number of nucleotides from a location within the read oligonucleotide sequence from which the read mer was divided;

generate a read mer table comprising a plurality of read mer table entries that is stored in said non-transitory memory, each read mer table entry in the plurality of read mer table entries comprising (i) a corresponding read mer in the plurality of read mers, (ii) the read sequence index and the read position index for the corresponding read mer, wherein the plurality of read mer table entries in the read mer table are sorted by ascending or descending order of read mer sequence;

divide each respective comparing oligonucleotide sequence in the comparing sequence set into one or more comparing mers thereby collectively forming a plurality of comparing mers, wherein the comparing sequence set comprises a plurality of comparing entries, wherein each respective comparing entry in the plurality of comparing entries comprises (i) a corresponding comparing oligonucleotide sequence and (ii) a corresponding comparing sequence index assigned to identify the corresponding comparing oligonucleotide sequence, and wherein the comparing oligonucleotide sequences in the comparing sequence set collectively form a known completely predetermined comparing oligonucleotide sequence;

assign to each respective comparing mer in the plurality of comparing mers the comparing oligonucleotide sequence index corresponding to the comparing sequence from which the respective comparing mer was divided;

assign a comparing position index to each respective comparing mer in the plurality of comparing mers identifying a number of nucleotides from a location within the comparing oligonucleotide sequence from which the comparing mer was divided;

generate a comparing mer table comprising a plurality of comparing mer table entries, each comparing mer table entry in the plurality of comparing mer table entries comprising (i) a corresponding comparing mer in the plurality of comparing mers and (ii) the comparing sequence index and the comparing position index for the corresponding comparing mer, wherein the plurality of comparing mer table entries are sorted by ascending or descending order of comparing mer sequence;

determine, for each respective read mer in the read mer table, each match between the respective read mer and a comparing mer in the comparing mer table by comparing the sequence of the respective read mer to the sequence of a comparing mer in the comparing mer table that has not been previously been compared to a read mer in the read mer table, thereby identifying each match between comparing mers and read mers in the read mer table and the comparing mer table; and order respective read oligonucleotide sequences in the plurality of read oligonucleotide sequences with respect to each other by sorting the combination of (i) the matches between comparing mers and read mers in the comparing mer table and the read mer table, and (ii) at least one of the group consisting of sequence index, orientation index, frameshift and position index of comparing mers in the corresponding comparing oligonucleotide sequences, to form an ordered plurality of read oligonucleotide sequences that collectively identify the nucleotide sequence matches in the comparing sequence set.

11. A computer system for identifying nucleotide sequence matches between a read sequence set and a comparing sequence set, wherein the comparing oligonucleotide sequences in the comparing sequence set collectively define a known completely predetermined comparing oligonucleotide sequence in a database of known sequences, comprising:

one or more processors;
a non-transitory computer readable medium; and
one or more programs stored in the non-transitory computer readable medium, the one or more programs, which when executed by the one or more processors, cause the computer system to:

divide each respective read oligonucleotide sequence in a read sequence set into one or more read mers thereby collectively forming a plurality of read mers, wherein the read sequence set comprises a plurality of read entries, wherein each respective read entry in the plurality of read entries comprises (i) a corresponding read oligonucleotide sequence in a plurality of read oligonucleotide sequences and (ii) a corresponding read sequence index assigned to identify the corresponding read oligonucleotide sequence;

assign each respective read mer in the plurality of read mers the read sequence index corresponding to a read oligonucleotide sequence from which the respective read mer was divided;

assign a read position index to each respective read mer in the plurality of read mers identifying a number of nucleotides from a location within the read oligonucleotide sequence from which the read mer was divided;

generate a read mer table comprising a plurality of read mer table entries that is stored in said non-transitory memory, each read mer table entry in the plurality of read mer table entries comprising (i) a corresponding read mer in the plurality of read mers, (ii) the read sequence index and the read position index for the corresponding read mer, wherein the plurality of read mer table entries in the read mer table are sorted by ascending or descending order of read mer sequence;

divide each respective comparing oligonucleotide sequence in the comparing sequence set into one or more comparing mers thereby collectively forming a plurality of comparing mers, wherein the comparing sequence set comprises a plurality of comparing entries, wherein each respective comparing entry in the plurality of comparing entries comprises (i) a corresponding comparing oligonucleotide sequence and (ii) a corresponding comparing sequence index assigned to identify the corresponding comparing oligonucleotide sequence, and wherein the comparing oligonucleotide sequences in the comparing sequence set collectively form a known completely predetermined comparing oligonucleotide sequence;

assign to each respective comparing mer in the plurality of comparing mers the comparing oligonucleotide sequence index corresponding to the comparing sequence from which the respective comparing mer was divided;

assign a comparing position index to each respective comparing mer in the plurality of comparing mers identifying a number of nucleotides from a location within the comparing oligonucleotide sequence from which the comparing mer was divided;

generate a comparing mer table comprising a plurality of comparing mer table entries, each comparing mer table entry in the plurality of comparing mer table entries comprising (i) a corresponding comparing mer in the plurality of comparing mers and (ii) the comparing sequence index and the comparing position index for the corresponding comparing mer, wherein the plurality of comparing mer table entries are sorted by ascending or descending order of comparing mer sequence;

determine, for each respective read mer in the read mer table, each match between the respective read mer and a comparing mer in the comparing mer table by comparing the sequence of the respective read mer to the sequence of a comparing mer in the comparing mer table that has not been previously been compared to a read mer in the read mer table, thereby identifying each match between comparing mers and read mers in the read mer table and the comparing mer table; and order respective read oligonucleotide sequences in the plurality of read oligonucleotide sequences with respect to each other by sorting the combination of (i) the matches between comparing mers and read mers in the comparing mer table and the read mer table, and (ii) at least one of the group consisting of sequence index, orientation index, frameshift and position index of comparing mers in the corresponding comparing oligonucleotide sequences, to form an ordered plurality of read oligonucleotide sequences that collectively identify the nucleotide sequence matches in the comparing sequence set.

12. The computer system of claim 11, wherein the known complete predetermined comparing oligonucleotide sequence is an existing sequence database.

13. The computer system of claim 11, wherein the known completely predetermined comparing oligonucleotide sequence comprises sequence reads derived from a biological sample.

14. The computer system of claim 13, wherein the biological sample is a single bacterial or viral strain.

15. The computer system of claim 14, wherein the biological sample is a pathogen.

16. The computer system of claim 11, wherein the comparing sequence set comprises one thousand comparing entries and the read sequence set comprises fifty read entries.

* * * * *

SEQUENCE LISTING

<160> NUMBER OF SEQ ID NOS: 5

<210> SEQ ID NO 1
<211> LENGTH: 11
<212> TYPE: DNA
<213> ORGANISM: Artificial Sequence
<220> FEATURE:
<223> OTHER INFORMATION: COMPLETELY ARTIFICIAL

<400> SEQUENCE: 1
gtggcccata t                                                              11

<210> SEQ ID NO 2
<211> LENGTH: 14
<212> TYPE: DNA
<213> ORGANISM: Artificial Sequence
<220> FEATURE:
<223> OTHER INFORMATION: COMPLETELY ARTIFICIAL

<400> SEQUENCE: 2
ggaaaagggg ggcg                                                           14

<210> SEQ ID NO 3
<211> LENGTH: 29
<212> TYPE: DNA
<213> ORGANISM: Artificial Sequence
<220> FEATURE:
<223> OTHER INFORMATION: COMPLETELY ARTIFICIAL

<400> SEQUENCE: 3
aaaaacctat aaccctgggg cgttcgtat                                           29

<210> SEQ ID NO 4
<211> LENGTH: 735
<212> TYPE: DNA
<213> ORGANISM: Artificial Sequence
<220> FEATURE:
<223> OTHER INFORMATION: COMPLETELY ARTIFICIAL

<400> SEQUENCE: 4
atgtccaaac tcgatctaaa cgccctgaac gaactgccga aggtagatcg cattctggcg         60
ctggcggaaa ctaacgccga actggaaaaa ctggacgctg aaggcccgcg tagcctgggc        120
gctggataat ctgcccggtg aatatgtact ttcttccagc tttggcattc aggcggcggt        180
gagcctgcat ctggtgaatc aattcgcccg gatattccgg tgatcctcac cgatacgggt       240
tacttgttcc cggaaaccta ccgctttatt gacgagttaa cggacaaact caagctcaac       300
ctgaaagtgt accgtgctac cgaaagcgca gcctggcagg aagcacgcta cggaaaactg       360
tgggagcagg gcgttgaagg cattgaaaag tacaatgaca tcaacaaagt cgaaccgatg       420
aaccgggctc tgaaagaact gaatgcgcaa acctggtttg ctggcctgcg ccgtgaacaa       480
tccggcagtc gtgccaattt accggtgctg gcaattcagc gtggcctatt taaagtgctg       540
ccgattatcg actgggataa ccgaactatt tatcagtacc tgcaaaaaca tggcctgaaa       600
tatcacccat tatgggatga aggatattta tcggtgggcg atacccatac aacccgtaaa       660
tgggaacccg gcatggcgga agaagaaacg cgtttctttg gcttaaaaag ggaatgtggg       720
ttacacgaag ggtaa                                                         735

<210> SEQ ID NO 5
<211> LENGTH: 735
<212> TYPE: DNA
<213> ORGANISM: Artificial Sequence -continued

```
<220> FEATURE:
<223> OTHER INFORMATION: COMPLETELY ARTIFICIAL

<400> SEQUENCE: 5
atgtccaaac tcgatctaaa cgccctgaac gaactgccga aggtagatcg cattctggcg        60
ctggcggaaa ctaacgccga actggaaaaa ctggacgctg aaggccgcgt agcctgggcg       120
ctggataatc tgcccggtga atatgtactt tcttccagct ttggcattca ggcggcggtg       180
agcctgcatc tggtgaatca aattcgcccg gatattccgg tgatcctcac cgatacgggt       240
tacttgttcc cggaaaccta ccgctttatt gacgagttaa cggacaaact caagctcaac       300
ctgaaagtgt accgtgctac cgaaagcgca gcctggcagg aagcacgcta ccgaaaactg       360
tgggagcagg gcgttgaagg cattgaaaag tacaatgaca tcaacaaagt cgaaccgatg       420
aaccgggctc tgaaagaact gaatgcgcaa acctggtttg ctggcctgcg ccgtgaacaa       480
tccggcagtc gtgccaattt accggtgctg gcaattcagc gtggcgtatt taaagtgctg       540
ccgattatcg actgggataa ccgaactatt tatcagtacc tgcaaaaaca tggcctgaaa       600
tatcacccat tatcggatga aggatattta tcggtgggcg atacccatac aacccgtaaa       660
tgggaacccg gcatggcgga agaagaaacg cgtttctttg gcttaaaaag ggaatgtggg       720
ttacacgaag ggtaa                                                       735
```